United States Patent [19]

Chakravarty et al.

[11] Patent Number: 5,804,578
[45] Date of Patent: Sep. 8, 1998

[54] PIPERIDINES, PYRROLIDINES AND HEXAHYDRO-1H-AZEPINES PROMOTE RELEASE OF GROWTH HORMONE

[75] Inventors: Prasun K. Chakravarty, Edison; Meng H. Chen, Westfield; Ravi Nargund, East Brunswick; Arthur A. Patchett; James R. Tata, both of Westfield; Mu Tsu Wu, Clark; Lihu Yang, Edison, all of N.J.

[73] Assignee: Merck & Co., Inc., Rahway, N.J.

[21] Appl. No.: 828,606

[22] Filed: Mar. 31, 1997

Related U.S. Application Data

[60] Provisional application No. 60/014,797, Apr. 3, 1996.

[51] Int. Cl.$^6$ .................. A01N 43/54; C07D 413/00; C07D 215/00; C07D 453/02
[52] U.S. Cl. .................. 514/227.8; 514/231.5; 514/269; 514/278; 514/314; 514/326; 544/60; 544/111; 544/333; 544/335; 546/16; 546/17; 546/135; 546/256
[58] Field of Search .................. 546/16, 17, 256, 546/135; 514/278, 326, 227.8, 231.5, 269, 314; 544/60, 111, 333, 335

[56] References Cited

U.S. PATENT DOCUMENTS

| | | | |
|---|---|---|---|
| 5,492,916 | 2/1996 | Morriello et al. | 514/318 |
| 5,492,920 | 2/1996 | Chen et al. | 514/323 |
| 5,494,919 | 2/1996 | Morriello et al. | 514/323 |
| 5,536,716 | 7/1996 | Chen et al. | 514/215 |
| 5,543,423 | 8/1996 | Zelle et al. | 514/332 |
| 5,559,128 | 9/1996 | Chakravarty et al. | 514/323 |
| 5,578,593 | 11/1996 | Chen et al. | 514/212 |

FOREIGN PATENT DOCUMENTS

| | | |
|---|---|---|
| WO 96/02530 | 2/1996 | WIPO. |
| WO 96/13265 | 5/1996 | WIPO. |
| WO 96/35713 | 11/1996 | WIPO. |
| WO 96/38471 | 12/1996 | WIPO. |

*Primary Examiner*—Mukund J. Shah
*Assistant Examiner*—Tamthom T. Ngo
*Attorney, Agent, or Firm*—J. Eric Thies; David L. Rose

[57] ABSTRACT

The present invention is directed to certain piperidines, pyrrolidines, and hexahydro-1H-azepines of the general structural formula:

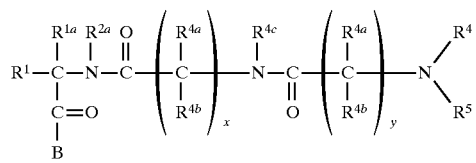

wherein B is selected from:

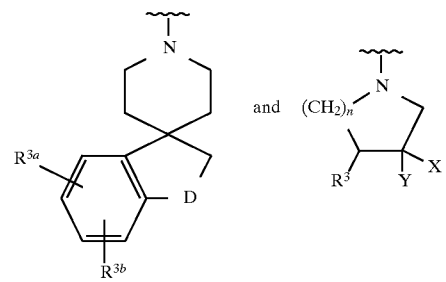

and $R^1$, $R^{1a}$, $R^{2a}$, $R^{3a}$, $R^{3b}$, $R^4$, $R^{4a}$, $R^{4b}$, $R^{4c}$, $R^5$, D, X, Y, n, x and y are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing such compounds as the active ingredient thereof are also disclosed.

20 Claims, No Drawings

PIPERIDINES, PYRROLIDINES AND HEXAHYDRO-1H-AZEPINES PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenyl-alanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues are disclosed in e.g., U.S. Pat. Nos. 5,206,235, 5,283,241, 5,284,841, 5,310,737, 5,317,017, 5,374,721, 5,430,144, 5,434,261, 5,438,136, 5,494,919, 5,494,920, and 5,492,916. Other growth hormone secretagogues are disclosed e.g., in PCT Patent Publications WO 94/13696, WO 94/19367, WO 95/03289, WO 95/03290, WO 95/09633, WO 95/11029, WO 95/12598, WO 95/13069, WO 95/14666, WO 95/16675, WO 95/16692, WO 95/17422, WO 95/17423, WO 95/34311, and WO 96/02530. The instant compounds are low molecular weight peptide analogs for promoting the release of growth hormone which have good stability in a variety of physiological environments and which may be administered parenterally, nasally or by the oral route.

SUMMARY OF THE INVENTION

The instant invention is directed to certain piperidines, pyrrolidines, and hexahydro-1H-azepines which have the ability to stimulate the release of natural or endogenous growth hormone. The compounds thus have the ability to be used to treat conditions which require the stimulation of growth hormone production or secretion such as in humans with a deficiency of natural growth hormone or in animals used for food or wool production where the stimulation of growth hormone will result in a larger, more productive animal. Thus, it is an object of the instant invention to describe the piperidine compounds. It is a further object of this invention to describe procedures for the preparation of such compounds. A still further object is to describe the use of such compounds to increase the secretion of growth hormone in humans and animals. A still further object of this invention is to describe compositions containing the piperidine compounds for the use of treating humans and animals so as to increase the level of growth hormone secretions. Further objects will become apparent from a reading of the following description.

DESCRIPTION OF THE INVENTION

The novel piperidines, pyrrolidines, and hexahydro-1H-azepines of the instant invention are described by structural Formula I:

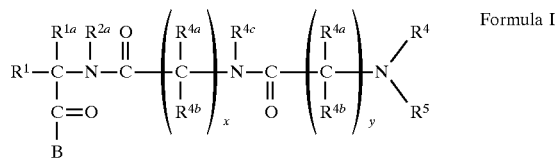

Formula I wherein:
R$^1$ is selected from the group consisting of:
  C$_1$–C$_{10}$ alkyl, -aryl-, aryl (C$_1$–C$_6$ alkyl)-, heteroaryl-, heteroaryl(C$_1$–C$_6$ alkyl)-, (C$_3$–C$_7$ cycloalkyl)-(C$_1$–C$_6$ alkyl)-, (C$_1$–C$_5$ alkyl)-K-(C$_1$–C$_5$ alkyl)-, aryl—(C$_{0-C5}$ alkyl)-K-(C$_1$–C$_5$ alkyl)-, heteroaryl—(C$_0$–C$_5$ alkyl)-K-(C$_1$–C$_5$ alkyl)-, and (C$_3$–C$_7$ cycloalkyl)-(C$_0$–C$_5$ alkyl)-K-(C$_1$–C$_5$ alkyl)-,
wherein K is —O—, —S(O)$_m$—, —N(R$^2$)C(O)—, —C(O)N(R$^2$)—, —OC(O)—, —C(O)O—, —CR$^2$=CR$^2$— or —C≡C—,
wherein R$^2$ and the alkyl groups may be further substituted with 1 to 9 halo, —S(O)$_m$R$^{2a}$, 1 to 3 of —OR$^{2a}$, or —C(O)OR$^{2a}$, and wherein aryl is phenyl or naphthyl, and heteroaryl is selected from indolyl, thiophenyl, benzofuranyl, benzothipheneyl, aza-indolyl, pyridinyl, quinolinyl, and benzimidazolyl, wherein aryl and heteroaryl are unsubstituted or substituted with phenyl, phenoxy, halophenyl, 1 to 3 of —C$_1$–C$_6$ alkyl, 1 to 3 of halo, 1 to 2 of —OR$^2$, methylenedioxy, —S(O)$_m$R$^2$, 1 to 2 of —CF$_3$, —OCF$_3$, nitro, —N(R$^2$)(R$^2$), —N(R$^2$)C(O)(R$^2$), —C(O)OR$^2$, —C(O)N(R$^2$)(R$^2$), —SO$_2$N(R$^2$)(R$^2$), —N(R$^2$)SO$_2$-aryl, or —N(R$^2$)SO$_2$R$^2$;

R$^{1a}$ is hydrogen or C$_1$–C$_4$ alkyl;

R$^2$ is selected from the group consisting of:
hydrogen, —C$_1$–C$_6$ alkyl, —C$_3$–C$_7$ cycloalkyl, and —CH$_2$-phenyl,
wherein the alkyl or the cyloalkyl is unsubstituted or substituted with hydroxyl, C$_1$–C$_3$ alkoxy, thioalkyl, C(O)OR$^{2a}$, and where, if two —C$_1$–C$_6$ alkyl groups are present on one atom, they may be joined to form a C$_3$–C$_8$ cyclic ring being selected from the group consisting of pyrrolidine, piperidine, piperazine, morpholine, thiomorpholine, optionally substituted by hydroxyl;

$R^{2a}$ is hydrogen or $C_1$–$C_6$ alkyl;

B is selected from:

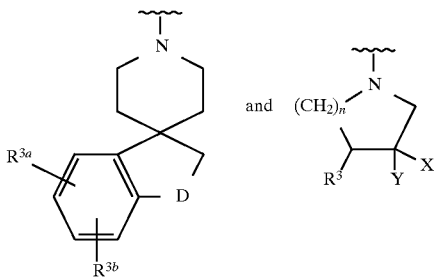

$R^3$ is selected from: hydrogen, —$(CH_2)_r$phenyl, —$(CH_2)_r$thienyl, —$(CH_2)_r$benzimidazolyl, —$(CH_2)_r$quinolinyl, —$(CH_2)_r$naphthyl, —$(CH_2)_r$indolyl, —$C_1$–$C_{10}$ alkyl, —$C_3$–$C_7$ cycloalkyl, where the phenyl, naphthyl, indolyl, thienyl, benzimidazolyl, quinolinyl, and $C_3$–$C_7$ cycloalkyl rings may be substituted by 1 to 3 substituents selected from the group consisting of: $C_1$–$C_6$ alkyl, halogen, —$OR^2$, —$NHSO_2CF_3$, —$(CH_2)_rOR^6$, —$(CH_2)_rN(R^2)(R^6)$, —$(CH_2)_r(R^6)$, —$(CH_2)_rC(O)OR^2$, —$(CH_2)_rC(O)OR^6$, —$(CH_2)_rOC(O)R^2$, —$(CH_2)_rOC(O)R^6$, —$(CH_2)_rC(O)R^2$, —$(CH_2)_rC(O)R^6$, —$(CH_2)_rC(O)N(R^2)(R^2)$, —$(CH_2)_rC(O)N(R^2)(R^6)$, —$(CH_2)_rN(R^2)C(O)(R^2)$, —$(CH_2)_rN(R^2)C(O)R^6$—$(CH^2)_rN(R^6)C(O)R^2$, —$(CH_2)_rN(R^6)C(O)R^6$, —$(CH_2)_rN(R^2)C(O)OR^2$, —$(CH_2)_rN(R^2)C(O)OR^6$, —$(CH_2)_rN(R^6)C(O)OR^2$, —$(CH_2)_rN(R^6)C(O)OR^6$, —$(CH_2)_rN(R^2)C(O)N(R^2)(R^6)$, —$(CH_2)_rN(R^2)C(O)N(R^2)(R^2)$, —$(CH_2)_rN(R^6)C(O)N(R^2)(R^6)$, —$(CH_2)_rN(R^2)SO_2R^2$, —$(CH_2)_rN(R^6)SO_2R^2$, —$(CH_2)_rN(R^6)SO_2R^6$, —$(CH_2)_rOC(O)N(R^2)(R^6)$, —$(CH_2)_rOC(O)N(R^2)(R^2)$, —$(CH_2)_rSO_2N(R^2)(R^6)$, —$(CH_2)_rOC(O)N(R^2)(R^2)$, —$(CH_2)_rSO_2N(R^2)(R^6)$, —$(CH_2)_rSO_2N(R^2)(R^2)$, —$(CH_2)_rN(R^2)SO_2N(R^2)(R^6)$, —$(CH_2)_rN(R^6)SO_2N(R^2)(R^6)$, —$(CH_2)_rS(O)_mR^6$, and —$(CH_2)_rS(O)_mR^2$;

$R^{3a}$ and $R^{3b}$ are independently selected from: hydrogen, phenyl, phenoxy, halophenyl, —$C_1$–$C_6$ alkyl, halogen, —$OR^2$, methylenedioxy, —$S(O)_mR^2$, —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, and —$N(R^2)SO^2R^2$;

$R^4$ and $R^5$ are independently selected from hydrogen, $C_1$–$C_6$ alkyl, and substituted $C_1$–$C_6$ alkyl where the substituents are selected from halo, hydroxy, phenyl, and $C_1$–$C_6$ alkoxycarbonyl;

or $R^5$ and $R^4$ may be taken together to form —$(CH_2)_d$—$L_a(CH_2)_e$— where $L_a$ is —$C(R^2)_2$—, —O—, —$S(O)_m$— or —$N(R^2)$—, d and e are independently 1 to 3 and $R^2$ is as defined above;

$R^{4a}$ and $R^{4b}$ are independently selected from: hydrogen, $C_1$–$C_6$ alkyl, trifluoromethyl, phenyl, or substituted $C_1$–$C_6$ alkyl where the substituents are selected from: imidazolyl, naphthyl, phenyl, indolyl, p-hydroxyphenyl, —$OR^2$, —$S(O)_mR^2$, —$C(O)OR^2$, $C_3$–$C_7$ cycloalkyl, —$N(R^2)(R^2)$, —$C(O)N(R^2)(R^2)$; or $R^{4a}$ and $R^{4b}$ may independently be joined to one or both of $R^4$ or $R^{4c}$ to form an alkylene bridge between the terminal nitrogen and the alkyl portion of the $R^{4a}$ or $R^{4b}$ and the $R^4$ or $R^{4c}$ group, wherein the bridges contain 1 to 8 carbons atoms; or $R^{4a}$ and $R^{4b}$ may be joined to one another to form $C_3$–$C_7$ cycloalkyl;

$R^{4c}$ is selected from hydrogen, $C_1$–$C_6$ alkyl, and substituted $C_1$–$C_6$ alkyl where the substituents are selected from 1 to 5 halo, 1 to 3 hydroxy, phenyl, napthyl, imidazolyl, indolyl, and $C_1$–$C_6$ alkoxycarbonyl;

$R^6$ is selected from: hydrogen, $C_1$–$C_6$ alkyl, and $(CH_2)_v$aryl, wherein the $(CH_2)_v$ and alkyl groups may be optionally substituted by —$O(R^2)$, —$S(O)_mR^2$, —$C(O)OR^2$, —$C(O)N(R^2)(R^2)$, —$SO_2N(R^2)(R^2)$, or —$N(R^2)C(O)N(R^2)(R^2)$, wherein the aryl group is selected from: phenyl, pyridyl, 1H-tetrazolyl, triazolyl, oxadiazolyl, pyrazolyl, thiadiazoyl, and benzimidazol-2-yl, which is optionally substituted with $C_1$–$C_6$ alkyl, $C_3$–$C_6$ cycloalkyl, amino, or hydroxyl;

X is selected from the group consisting of: hydrogen, —C≡N, —$(CH_2)_qN(R^2)C(O)R^2$, —$(CH_2)_qN(R^2)C(O)(CH_2)_t$aryl, —$(CH_2)_qN(R^2)SO_2(CH_2)_t$aryl, —$(CH_2)_qN(R^2)SO_2R^2$, —$(CH_2)_qN(R^2)C(O)N(R^2)(CH_2)_t$aryl, —$(CH_2)_qN(R^2)C(O)N(R^2)(R^2)$, —$(CH_2)_qC(O)N(R^2)(R^2)$, —$(CH_2)_qC(O)N(R^2)(CH_2)_t$aryl, —$(CH_2)_qC(O)OR^2$, —$(CH_2)_qC(O)O(CH_2)_t$aryl, —$(CH_2)_qOR^2$, —$(CH_2)_qOC(O)R^2$, —$(CH_2)_qOC(O)(CH^2)_t$aryl, —$(CH_2)_qOC(O)N(R^2)(R^2)$, —$(CH_2)_qC(O) R^2$, —$(CH_2)_qC(O)(CH_2)_t$aryl, —$(CH_2)_qN(R^2)C(O)OR^2$, —$(CH_2)_qN(R^2)SO_2N(R^2)(R^2)$, —$(CH_2)_qS(O)_mR^2$, and —$(CH_2)_qS(O)_m(CH_2)_t$aryl, where $R^2$, $(CH_2)_q$ and $(CH_2)_t$ group may be optionally substituted with $C_1$–$C_4$ alkyl, hydroxyl, $C_1$–$C_4$ lower alkoxy, carboxyl, $N(R^2)(R^2)$, $CONH_2$, $S(O)_mCH_3$, carboxylate $C_1$–$C_4$ alkyl esters, or 1H-tetrazol-5-yl, and aryl is phenyl, naphthyl, pyridyl, thiazolyl, or 1H-tetrazol-5-yl groups which may be optionally substituted with halogen, —$OR^2$, —$CON(R^2)(R^2)$, —$C(O)OR^2$, $C_1$–$C_4$ alkyl, —$S(O)_mR^2$, or 1H-tetrazol-5-yl;

Y is selected from the group consisting of: hydrogen, $C_1$–$C_{10}$ alkyl, —$(CH_2)_t$aryl, —$(CH_2)_q(C_3$–$C_7$ cycloalkyl), —$(CH_2)_q$-K-$(C_1$–$C_6$ alkyl), —$(CH_2)_q$-K-$(CH_2)_t$aryl, —$(CH_2)_q$-K-$(CH_2)_t$($C_3$–$C_7$ cycloalkyl containing O, $NR^2$ S) and —$(CH_2)_q$-K-$(CH_2)_t$($C_3$–$C_7$ cycloalkyl), where K is O, $S(O)_m$, $C(O)NR^2$, CH=CH, C≡C, $N(R^2)C(O)$, $C(O)NR^2$, C(O)O, or OC(O), and where the alkyl, $R^2$, $(CH_2)_q$ and $(CH_2)_t$ groups are optionally substituted by $C_1$–$C_4$ alkyl, hydroxyl, $C_1$–$C_4$ lower alkoxy, carboxyl, —$CONH_2$ or a carboxylate $C_1$–$C_4$ alkyl ester, and aryl is phenyl, naphthyl, pyridyl, 1-H-tetrazol-5-yl, thiazolyl, imidazoly, indolyl, oxadiazoyl, pyrimidinyl, thiadiazolyl, pyrazolyl, oxazolyl, isoxazolyl, thiopheneyl, quinolinyl, pyrrazinyl, or isothiazolyl which is optionally substituted with halogen, —$OR^2$, —$C(O)OR^2$, $N(R^2)(R^2)$, —$C(O)N(R^2)(R^2)$, nitro, cyano, benzyl, $C_1$–$C_4$ alkyl, —$S(O)_mR^2$, or 1H-tetrazol-5-yl;

D is selected from: —$N(R^7)$——$S(O)_m$—, —C(O)— and —$C(H)(R^7)$—, wherein $R^7$ is selected from: —$R^2$, —$OR^2$, —$(CH_2)_q$aryl, —$C(O)R^2$, —$C(O)(CH_2)_q$aryl, —$SO_2R^2$, —$SO_2(CH_2)_q$aryl, —$C(O)N(R^2)(R^2)$, —$C(O)N(R^2)(CH_2)_q$aryl, —$C(O)OR^2$, 1-H-tetrazol-5-yl, —$SO_2N(R^2)$aryl, —$SO_2N(R^2)(R^2)$ and the $(CH_2)_q$ may be optionally substituted by $C_1$–$C_4$ alkyl, and the $R^2$ and aryl may be optionally further substituted with a substituent selected from: —$OR^{2a}$, —$O(CH_2)_q$ aryl, —$C(O)OR^{2a}$, —$C(O)(CH_2)_q$ aryl, —$C(O)N(R^{2a})(R^{2a})$, —$C(O)N(R^{2a})(CH_2)_1$ aryl, halogen, —$N(R^{2a})(R^{2a})$, —$C_1$–$C_4$ alkyl, 1,2,4- triazolyl, 1-H-tetrazol-5-yl, —C(O)NHSO$_2$R$^{2a}$, —S(O)$_m$R$^{2a}$, —C(O)NHSO$_2$(CH$_2$)$_q$aryl, —N(R$^2$)C(O)N(R$^{2a}$)(R$^{2a}$), —N(R$^{2a}$)C(O)N(R$^{2a}$)(CH$_2$)$_q$aryl, —N(R$^{2a}$)(R$^{2a}$), —N(R$^{2a}$)C(O)R$^{2a}$, —N(R$^{2a}$)C(O)(CH$_2$)$_q$ aryl, —OC(O)N(R$^{2a}$)(R$^{2a}$), —OC(O)N(R$^{2a}$)(CH$_2$)$_q$ aryl;

l is 0, 1 or 2;
m is 0, 1, or 2;
n is 0, 1, or 2;
q is 0, 1, 2, 3, or 4;
r is 0, 1, 2, or 3;
t is 0, 1, 2, or 3;
v is 0, 1, or 2;
x is 1;
y is 1;

and pharmaceutically acceptable salts and individual diastereomers thereof.

In the above structural formula and throughout the instant specification, the following terms have the indicated meanings:

When n is 1 a pyrrolidine ring is formed, when n is 2 a piperidine ring is formed, and when n is 3 the ring is designated a hexahydro-1-H-azepine.

The alkyl groups specified above are intended to include those alkyl groups of the designated length in either a straight or branched configuration and if two carbon atoms or more they may include a double or a triple bond. Exemplary of such alkyl groups are methyl, ethyl, propyl, isopropyl, butyl, sec-butyl, tertiary butyl, pentyl, isopentyl, hexyl, isohexyl, allyl, propargyl, and the like.

The alkoxy groups specified above are intended to include those alkoxy groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl, which may be optionally substituted by 1 to 3 of C$_1$–C$_6$ alkyl, 1 to 3 of halogen, 1 to 2 of OR$_2$, methylenedioxy, —S(O)$_m$R$^2$, 1 to 2 of —CF$_3$, —OCF$_3$, nitro, —N(R$_2$)C(O)(R$_2$), —C(O)OR$_2$, —C(O)N(R$_2$)(R$_2$), —1H-tetrazol-5-yl, —SO$_2$N(R$_2$)(R$_2$), —N(R$_2$)SO$_2$ phenyl, or —N(R$_2$)SO$_2$R$_2$, wherein R$_2$ is as defined herein.

Certain of the above defined terms may occur more than once in the above formula and upon such occurrence each term shall be defined independently of the other.

Preferred compounds of the instant invention include those of Formula Ia:

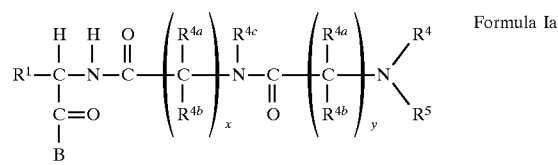

Formula Ia wherein:
R$^1$ is selected from the group consisting of:
C$_1$–C$_{10}$ alkyl, -aryl-, aryl (C$_1$–C$_6$ alkyl)-, heteroaryl-, heteroaryl(C$_1$–C$_6$ alkyl)-, (C$_3$–C$_7$ cycloalkyl)-(C$_1$–C$_6$ alkyl)-, (C$_1$–C$_5$ alkyl)-K-(C$_1$–C$_5$ alkyl)-, aryl-(C$_0$–C$_5$ alkyl)-K-(C$_1$–C$_5$ alkyl)-, heteroaryl-(C$_0$–C$_5$ alkyl)-K-(C$_1$–C$_5$ alkyl)-, and (C$_3$–C$_7$ cycloalkyl)-(C$_0$–C$_5$ alkyl)-K-(C$_1$–C$_5$ alkyl)-,
wherein K is —O—, —S(O)$_m$—, —N(R$^2$)C(O)—, —C(O)N(R$^2$)—, —OC(O)—, —C(O)O—, —CR$^2$=CR$^2$— or —C≡C—,
wherein R$^2$ and the alkyl groups may be further substituted with 1 to 9 halo, —S(O)$_m$R$^{2a}$, 1 to 3 of —OR$^{2a}$, or —C(O)OR$^{2a}$, and wherein aryl is phenyl or naphthyl, and heteroaryl is selected from indolyl, thiophenyl, benzofuranyl, benzothiopheneyl, aza-indolyl, pyrindinyl, quinolinyl, and benzimidazolyl, wherein aryl and heteroaryl are unsubstituted or substituted with phenyl, phenoxy, halophenyl, 1 to 3 of —C$_1$–C$_6$ alkyl, 1 to 3 of halo, 1 to 2 of —OR$^2$, methylenedioxy, —S(O)$_m$R$^2$, 1 to 2 of —CF$_3$, —OCF$_3$, nitro, —N(R$^2$)(R$^2$), —N(R$^2$)C(O)(R$^2$), —C(O)OR$^2$, —C(O)N(R$^2$)(R$^2$), —SO$_2$N(R$^2$)(R$^2$), —N(R$^2$)SO$_2$-aryl, or —N(R$^2$)SO$_2$R$^2$;

R$^2$ is selected from the group consisting of:
hydrogen, —C$_1$–C$_6$ alkyl, —C$_3$–C$_7$ cycloalkyl, and —CH$_2$-phenyl,
wherein the alkyl or the cyloalkyl is unsubstituted or substituted with hydroxyl, C$_1$–C$_3$ alkoxy, thioalkyl, —C(O)OR$^{2a}$, and wherein, if two —C$_1$–C$_6$ alkyl groups are present on one atom, the groups may be optionally joined to form a C$_3$–C$_8$ cyclic ring being selected from the group consisting of pyrrolidine, piperidine, piperazine, morpholine, thiomorpholine;

B is selected from:

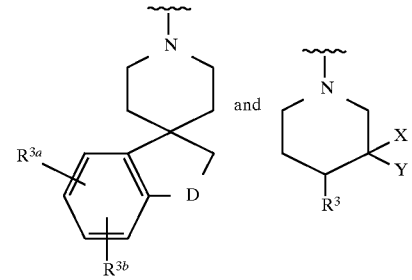

R$^3$ is selected from: hydrogen, phenyl, naphthyl, indolyl, benzimidazolyl, thienyl, quinolinyl, where the phenyl, naphthyl, benzimidazolyl, thienyl, quinolinyl, and indolyl may be substituted by 1 to 3 substituents selected from the group consisting of: C$_1$–C$_6$ alkyl, halogen, —OR$^2$, —(CH$_2$)$_r$OR$^6$, —(CH$_2$)$_r$N(R$^2$)(R$^6$), —(CH$_2$)$_r$(R$^6$), —(CH$_2$)$_r$C(O)OR$^2$, —(CH$_2$)$_r$C(O)OR$^6$, —(CH$_2$)$_r$C(O)R$^2$, —(CH$_2$)$_r$C(O)R$^6$, —(CH$_2$)$_r$C(O)N(R$^2$)(R$^2$), —$(CH_2)_rC(O)N(R^2)(R^6)$, —$(CH_2)_rN(R^2)C(O)(R^2)$, —$(CH_2)_rN(R^2)C(O)R^6$—$(CH_2)_rN(R^6)C(O)R^2$, —$(CH_2)_rN(R^6)C(O)R^6$, —$(CH_2)_rN(R^2)C(O)OR^2$, —$(CH_2)_rN(R^2)C(O)OR^6$, —$(CH_2)_rN(R^6)C(O)OR^2$, —$(CH_2)_rN(R^6)C(O)OR^6$, —$(CH_2)_rN(R^2)C(O)N(R^2)(R^6)$, —$(CH_2)_rN(R^2)C(O)N(R^2)(R^2)$, —$(CH_2)_rN(R^6)C(O)N(R^2)(R^6)$, —$(CH_2)_rN(R^2)SO_2R^2$, —$(CH_2)_rN(R^6)SO_2R^2$, —$(CH_2)_rN(R^6)SO_2R^6$, —$(CH_2)_rOC(O)N(R^2)(R^6)$, —$(CH_2)_rSO_2N(R^2)(R^6)$, —$(CH_2)_rSO_2N(R^2)(R^6)$, —$(CH_2)_rSO_2N(R^2)(R^2)$, —$(CH_2)_rS(O)_mR^6$, and —$(CH_2)_rS(O)_mR^2$;

$R^{3a}$ and $R^{3b}$ are independently selected from: hydrogen, phenyl, phenoxy, halophenyl, —$C_1$-$C_6$ alkyl, halogen, —$OR^2$, methylenedioxy, —$S(O)_mR^2$, —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, and —$N(R^2)SO^2R^2$;

$R^4$ and $R^5$ are independently selected from hydrogen, $C_1$-$C_6$ alkyl, and substituted $C_1$-$C_6$ alkyl where the substituents are selected from halo, hydroxy, phenyl, and $C_1$-$C_6$ alkoxycarbonyl;

or $R^5$ and $R^4$ may be taken together to form —$(CH_2)_d$—$L_a(CH_2)_e$— where $L_a$ is —$C(R^2)_2$—, —O—, —$S(O)_m$— or —$N(R^2)$—, d and e are independently 1 to 3 and $R^2$ is as defined above;

$R^{4a}$ and $R_{4b}$ are independently selected from: hydrogen, $C_1$-$C_6$ alkyl, trifluoromethyl, phenyl, or substituted $C_1$-$C_6$ alkyl where the substituents are selected from: imidazolyl, naphthyl, phenyl, indolyl, p-hydroxyphenyl, —$OR^2$, —$S(O)_mR^2$, —$C(O)OR^2$, $C_3$-$C_7$ cycloalkyl, —$N(R^2)(R^2)$, —$C(O)N(R^2)(R^2)$; or $R^{4a}$ and $R^{4b}$ may independently be joined to one or both of $R^4$ or $R^{4c}$ to form an alkylene bridge between the terminal nitrogen and the alkyl portion of the $R^{4a}$ or $R^{4b}$ and the $R^4$ or $R^{4c}$ group, wherein the bridges contain 1 to 5 carbons atoms; or $R^{4a}$ and $R^{4b}$ may be joined to one another to form $C_3$-$C_7$ cycloalkyl;

$R^{4c}$ is selected from hydrogen, $C_1$-$C_6$ alkyl, and substituted $C_1$-$C_6$ alkyl where the substituents are selected from 1 to 5 halo, 1 to 3 hydroxy, phenyl, $C_1$-$C_6$ alkoxycarbonyl;

$R^6$ is selected from: hydrogen, $C_1$-$C_6$ alkyl, and $(CH_2)_v$aryl, wherein the $(CH_2)_v$ and alkyl groups may be optionally substituted by —$O(R^2)$, —$S(O)_mR^2$, —$C(O)OR^2$, —$C(O)N(R^2)(R^2)$, —$SO_2N(R^2)(R^2)$, or —$N(R^2)C(O)N(R^2)(R^2)$, wherein the aryl group is selected from: phenyl, pyridyl, 1H-tetrazolyl, triazolyl, oxadiazolyl, pyrazolyl, thiadiazoyl, and benzimidazol-2-yl, which is optionally substituted with $C_1$-$C_6$ alkyl, $C_3$-$C_6$ cycloalkyl, amino, or hydroxyl;

X is selected from the group consisting of: hydrogen, —C≡N, —$(CH_2)_qN(R^2)C(O)R^2$, —$(CH_2)_qN(R^2)C(O)(CH_2)_t$aryl, —$(CH_2)_qN(R^2)SO_2(CH_2)_t$aryl, —$(CH_2)_qN(R^2)SO_2R^2$, —$(CH_2)_qN(R^2)C(O)N(R^2)(CH_2)_t$aryl, —$(CH_2)_qN(R^2)C(O)N(R^2)(R^2)$, —$(CH_2)_qC(O)N(R^2)(R^2)$, —$(CH_2)_qC(O)N(R^2)(CH_2)_t$aryl, —$(CH_2)_qC(O)OR^2$, —$(CH_2)_qC(O)O(CH_2)_t$aryl, —$(CH_2)_qOR^2$, —$(CH_2)_qOC(O)R^2$, —$(CH_2)_qOC(O)(CH^2)_t$aryl, —$(CH_2)_qOC(O)N(R^2)(R^2)$, —$(CH_2)_qC(O)R^2$, —$(CH_2)_qC(O)(CH_2)_t$aryl, —$(CH_2)_qN(R^2)C(O)OR^2$, —$(CH_2)_qN(R^2)SO_2N(R^2)(R^2)$, —$(CH_2)_qS(O)_mR^2$, and —$(CH_2)_qS(O)_m(CH_2)_t$aryl, where $R^2$, $(CH_2)_q$ and $(CH_2)_t$ group may be optionally substituted with $C_1$-$C_4$ alkyl, hydroxyl, $C_1$-$C_4$ lower alkoxy, carboxyl, $N(R^2)(R^2)$, $CONH_2$, $S(O)_mCH_3$, carboxylate $C_1$-$C_4$ alkyl esters, or 1H-tetrazol-5-yl, and aryl is phenyl, naphthyl, pyridyl, thiazolyl, or 1H-tetrazol-5-yl groups which may be optionally substituted with halogen, —$OR^2$, —$CON(R^2)(R^2)$, —$C(O)OR^2$, $C_1$-$C_4$ alkyl, —$S(O)_mR^2$, or 1H-tetrazol-5-yl;

Y is selected from the group consisting of:
hydrogen, $C_1$-$C_{10}$ alkyl, —$(CH_2)_t$aryl, —$(CH_2)_q(C_3$-$C_7$ cycloalkyl), —$(CH_2)_q$-K-$(C_1$-$C_6$ alkyl), —$(CH_2)_q$-K-$(CH_2)_t$aryl, —$(CH_2)_q$-K-$(CH_2)_t(C_3$-$C_7$ cycloalkyl containing O, $NR^2$ S) and —$(CH_2)_q$-K-$(CH_2)_t(C_3$-$C_7$ cycloalkyl), where K is O, $S(O)_m$, $C(O)NR^2$, CH=CH, C≡C, $N(R^2)C(O)$, $C(O)NR^2$, $C(O)O$, or $OC(O)$, and where the allyl, $R^2$, $(CH_2)_q$ and $(CH_2)_t$ groups are optionally substituted by $C_1$-$C_4$ alkyl, hydroxyl, $C_1$-$C_4$ lower alkoxy, carboxyl, —$CONH_2$ or a carboxylate $C_1$-$C_4$ alkyl ester, and aryl is phenyl, naphthyl, pyridyl, 1-H-tetrazol-5-yl, thiazolyl, imidazoly, indolyl, oxadiazoyl, pyrimidinyl, thiadiazolyl,pyrazolyl, oxazolyl, isoxazolyl, thiopheneyl, quinolinyl, pyrrazinyl, or isothiazolyl which is optionally substituted with halogen, —$OR^2$, —$C(O)OR^2$, $N(R^2)(R^2)$, —$C(O)N(R^2)(R^2)$, nitro, cyano, benzyl, $C_1$-$C_4$ alkyl, —$S(O)_mR^2$, or 1H-tetrazol-5-yl;

D is selected from: —$N(R^7)$—, —$S(O)_m$—, —$C(O)$— and —$C(H)(R^7)$—, wherein $R^7$ is selected from: —$R^2$, —$(CH_2)_q$aryl, —$C(O)R^2$, —$SO_2R^2$, —$C(O)N(R^2)(R^2)$, —$C(O)OR^2$, 1-H-tetrazol-5-yl, —$SO_2N(R^2)$aryl, —$SO_2N(R^2)(R^2)$ and the $(CH_2)_q$ may be optionally substituted by $C_1$-$C_4$ alkyl, and the $R^2$ and aryl may be optionally further substituted with a substituent selected from: —$OR^{2a}$, —$C(O)OR^{2a}$, —$C(O)N(R^{2a})(R^{2a})$, halogen, —$C_1$-$C_4$ alkyl, and the aryl is selected from of triazolyl, oxadiazolyl, thiadiazolyl, thiazolyl, imidazolyl, and 1-H-tetrazolyl;

l is 0, 1 or 2;
m is 0, 1, or 2;
q is 0, 1, 2, 3, or 4;
r is 0, 1, 2, or 3;
t is 0, 1, 2, or 3;
v is 0, 1, or 2;
x is 1;
y is 1;

and pharmaceutically acceptable salts and individual diastereomers thereof.

More preferred compounds of the instant invention include those of Formula Ib:

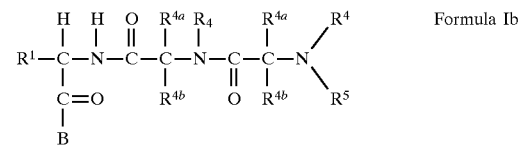

Formula Ib wherein:

$R^1$ is selected from the group consisting of:

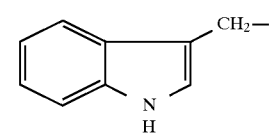

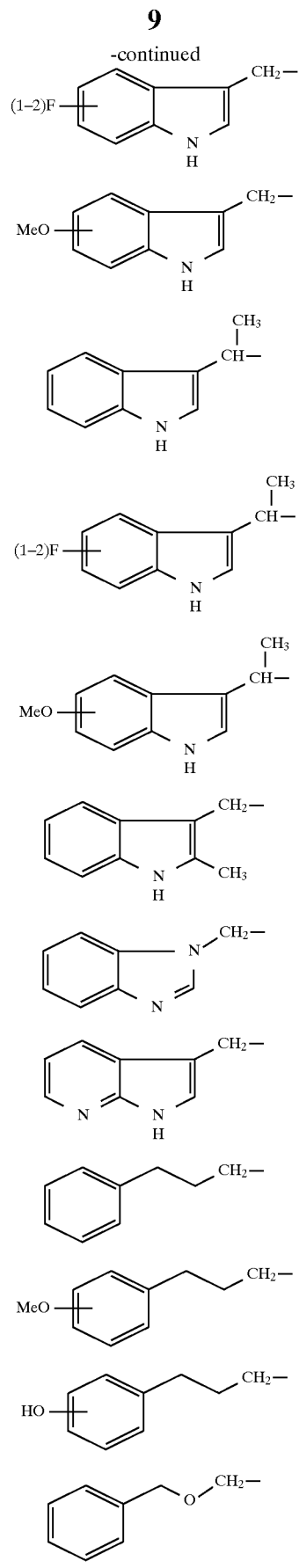

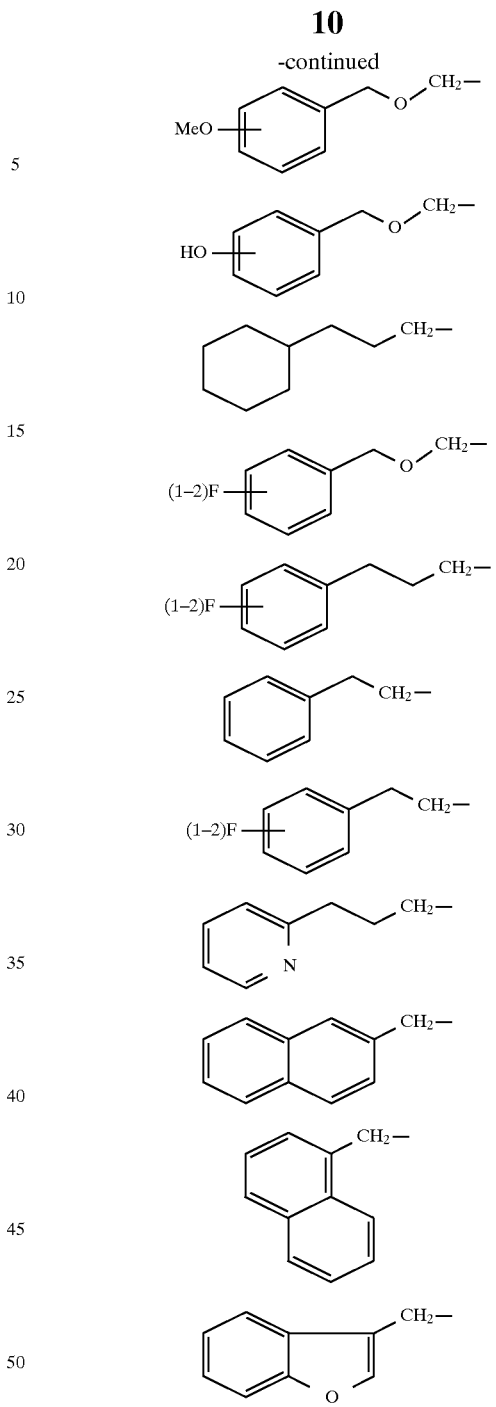

or their regioisomers where not specified;

R² is selected from the group consisting of:
hydrogen, —$C_1$–$C_6$ alkyl, —$C_3$–$C_7$ cycloalkyl, and —$CH_2$-phenyl, wherein the alkyl or the cyloalkyl is unsubstituted or substituted with hydroxyl, $C_1$–$C_3$ alkoxy, thioalkyl, —C(O)OR$^{2a}$, and wherein, if two —$C_1$—$C_6$ alkyl groups are present on one atom, the groups may be optionally joined to form a $C_3$–$C_8$ cyclic ring being selected from the group consisting of pyrrolidine, piperidine, piperazine, morpholine, thiomorpholine;

R$^{2a}$ is hydrogen, or $C_1$–$C_4$ alkyl;

B is selected from:

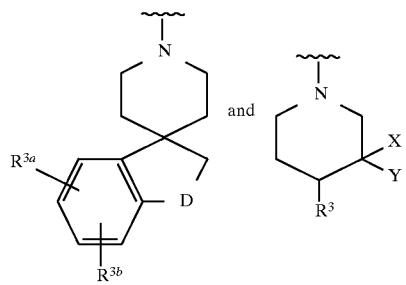

and

R³ is selected from: hydrogen or phenyl, wherein the phenyl is substituted in the ortho position by a substituent selected from the group consisting of: $C_1$–$C_6$ alkyl, halogen, —$OR^2$, —$(CH_2)_rOR^6$, —$(CH_2)_rN(R^2)(R^6)$, —$(CH_2)_r(R^6)$, —$(CH_2)_rC(O)OR^2$, —$(CH_2)_rC(O)OR^6$, —$(CH_2)_rC(O)R^2$, —$(CH_2)_rC(O)R^6$, —$(CH_2)_rC(O)N(R^2)(R^2)$, —$(CH_2)_rC(O)N(R^2)(R^6)$, —$(CH_2)_rSO_2N(R^2)(R^6)$, —$(CH_2)_rSO_2N(R^2)(R^2)$, —$(CH_2)_rS(O)_mR^6$, and —$(CH_2)_rS(O)_mR^2$;

$R^{3a}$ and $R^{3b}$ are independently selected from: hydrogen, —$C_1$–$C_6$ alkyl and halogen;

$R^4$ and $R^5$ are independently selected from hydrogen, $C_1$–$C_6$ alkyl, and substituted $C_1$–$C_6$ alkyl where the substituents are selected from halo, hydroxy, phenyl, and $C_1$–$C_6$ alkoxycarbonyl; or $R^5$ and $R^4$ may be taken together to form —$(CH_2)_d$—$L_a(CH_2)_e$— where $L_a$ is —$C(R^2)_2$—, —O—, —$S(O)_m$— or —$N(R^2)$—, d and e are independently 1 to 3 and $R^2$ is as defined above;

$R^{4a}$ and $R^{4b}$ are independently selected from: hydrogen, $C_1$–$C_6$ alkyl, or substituted $C_1$–$C_6$ alkyl where the substituents are selected from: imidazolyl, naphthyl, phenyl, indolyl, and p-hydroxyphenyl;

$R^{4c}$ is selected from hydrogen, $C_1$–$C_6$ alkyl, and substituted $C_1$–$C_6$ alkyl where the substituents are selected from 1 to 5 halo, 1 to 3 hydroxy, phenyl, $C_1$–$C_6$ alkoxycarbonyl;

$R^6$ is selected from: hydrogen, $C_1$–$C_6$ alkyl, and $(CH_2)_v$aryl, wherein the $(CH_2)_v$ and alkyl groups may be optionally substituted by —$O(R^2)$, —$S(O)_mR^2$, —$C(O)OR^2$, —$C(O)N(R^2)(R^2)$, —$SO_2N(R^2)(R^2)$, or —$N(R^2)C(O)N(R^2)(R^2)$, wherein the aryl group is selected from: phenyl, pyridyl, 1H-tetrazolyl, triazolyl, oxadiazolyl, pyrazolyl, thiadiazoyl, and benzimidazol-2-yl, which is optionally substituted with $C_1$–$C_6$ alkyl, $C_3$–$C_6$ cycloalkyl, amino, or hydroxyl;

X is selected from the group consisting of: hydrogen,

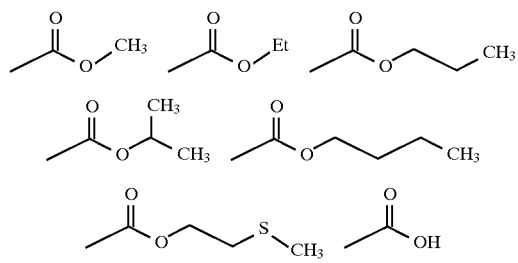

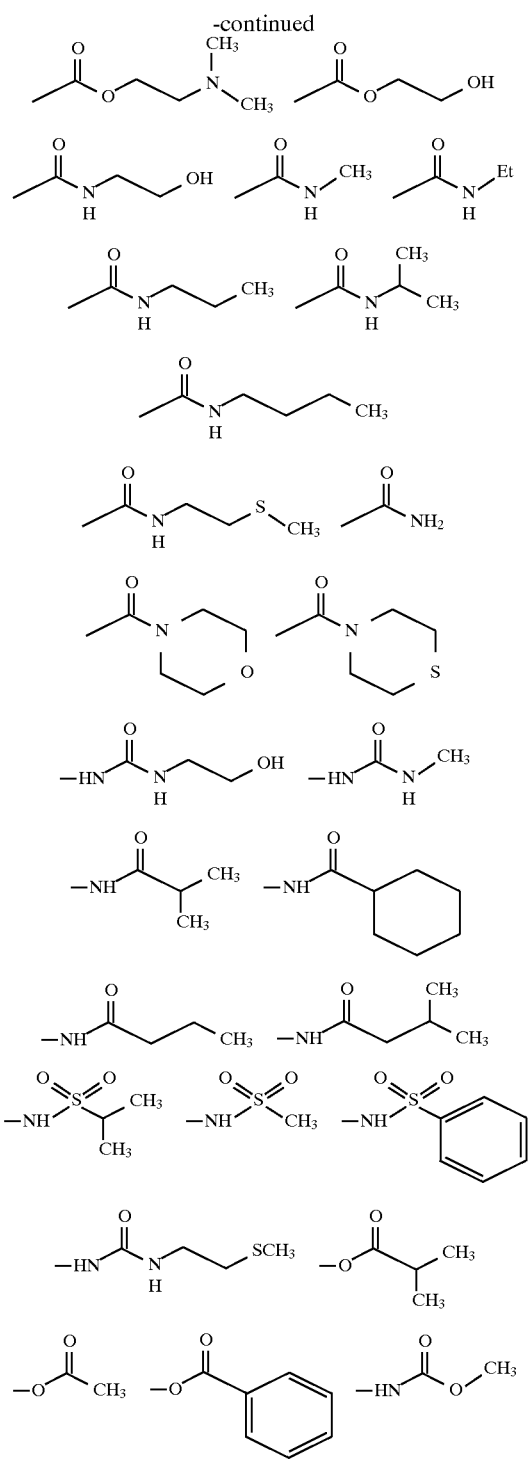

and further selected from the following group of heterocycles

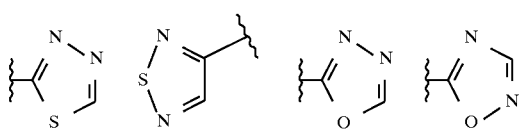

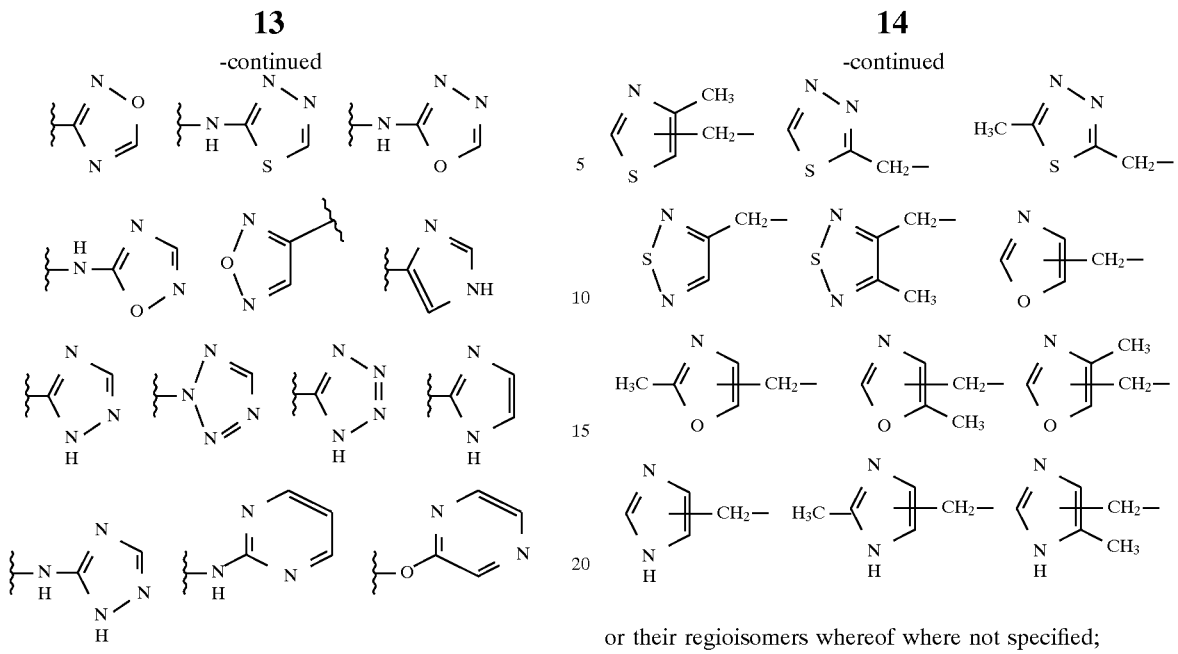

wherein the heterocycle is optionally substituted with a substituent selected from: —N(R²)(R²), —O(R²), $C_1$–$C_3$ alkyl, halogen, and trifluoromethyl;

Y is selected from the group consisting of: hydrogen,

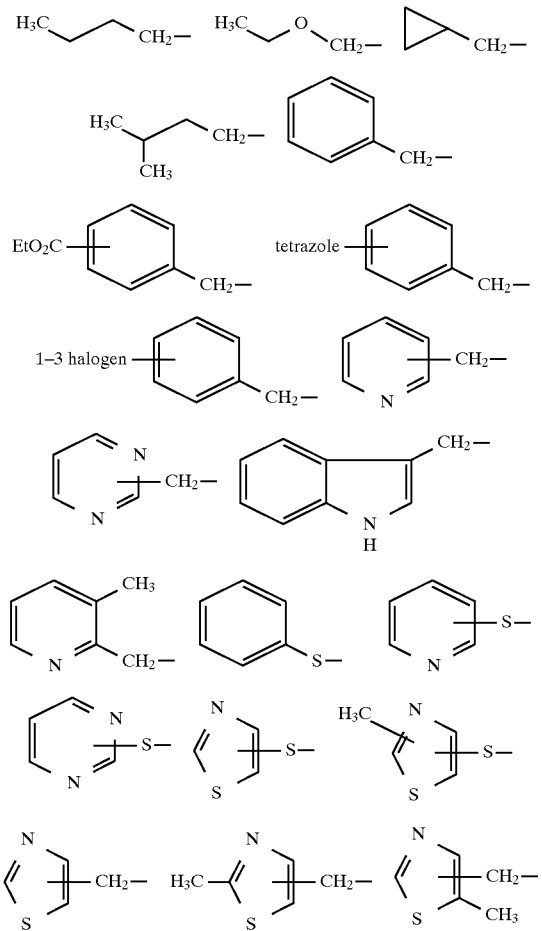

or their regioisomers whereof where not specified;

D is selected from: —N(R⁷)—, —S(O)$_m$—, —C(O)— and —C(H)(R⁷)—, wherein R⁷ is selected from: —R², —(CH₂)$_q$aryl, —C(O)R², —SO₂R², —C(O)N(R²)(R²), —C(O)OR², 1-H-tetrazol-5-yl, —SO₂N(R²)aryl, —SO₂N(R²)(R²) and the (CH₂)$_q$ may be optionally substituted by $C_1$–$C_4$ alkyl, and the R² and aryl may be optionally further substituted with a substituent selected from: —OR$^{2a}$, —C(O)OR$^{2a}$, —C(O)N(R$^{2a}$)(R$^{2a}$), halogen, —$C_1$–$C_4$ alkyl, and the aryl is selected from of triazolyl, oxadiazolyl, 1H-tetrazolyl, and thiadiazolyl;

l is 0, 1 or 2;
m is 0, 1, or 2;
q is 0, 1, 2, 3, or 4;
r is 0, 1, 2, or 3;
t is 0, 1, 2, or 3;
v is 0, 1, or 2;

and pharmaceutically acceptable salts and individual diastereomers thereof.

One embodiment of the most preferred compounds of the instant invention includes compounds of the formula:

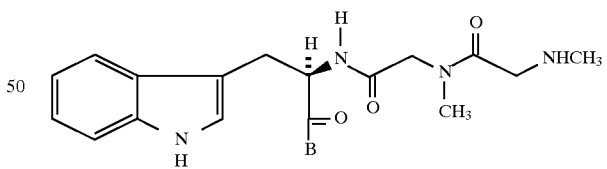

wherein B is selected from the group consisting of:

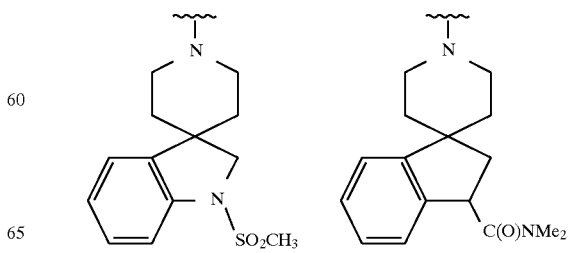

-continued

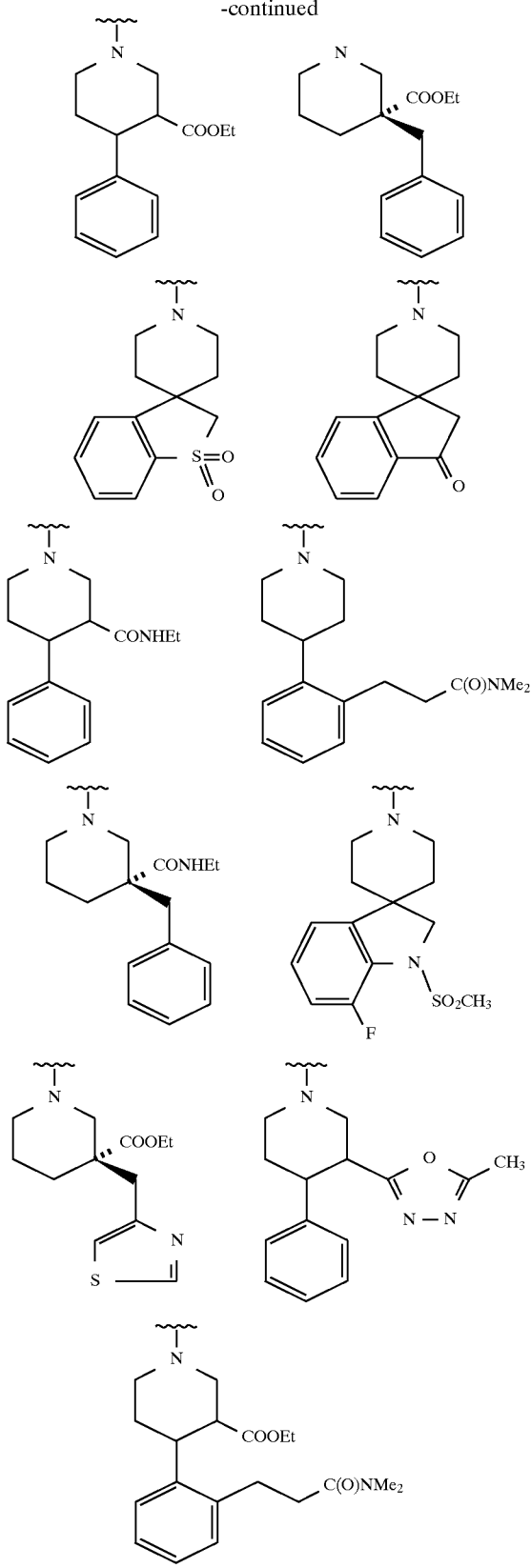

and pharmaceutically acceptable salts and individual diastereomers thereof.

Another embodiment of the most preferred compounds of the instant invention includes compounds of the formula:

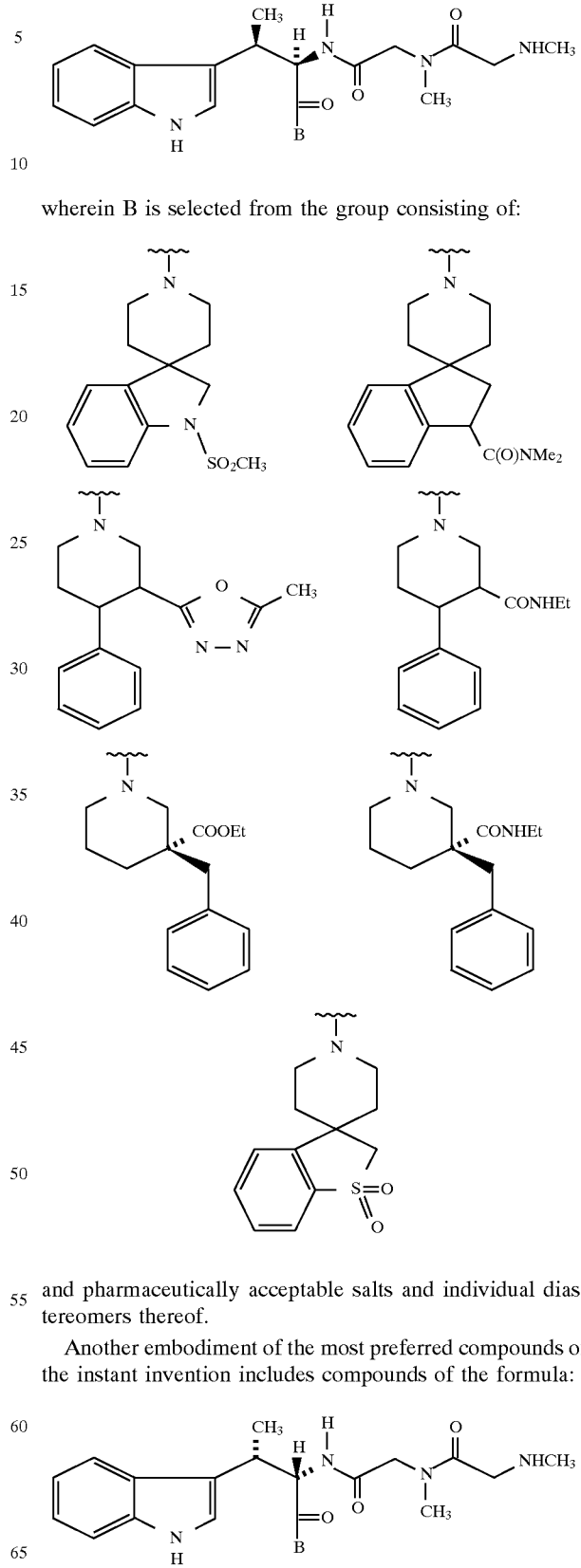

wherein B is selected from the group consisting of:

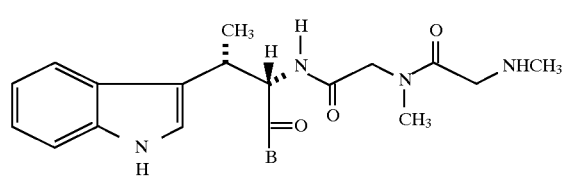

and pharmaceutically acceptable salts and individual diastereomers thereof.

Another embodiment of the most preferred compounds of the instant invention includes compounds of the formula:

wherein B is selected from the group consisting of:

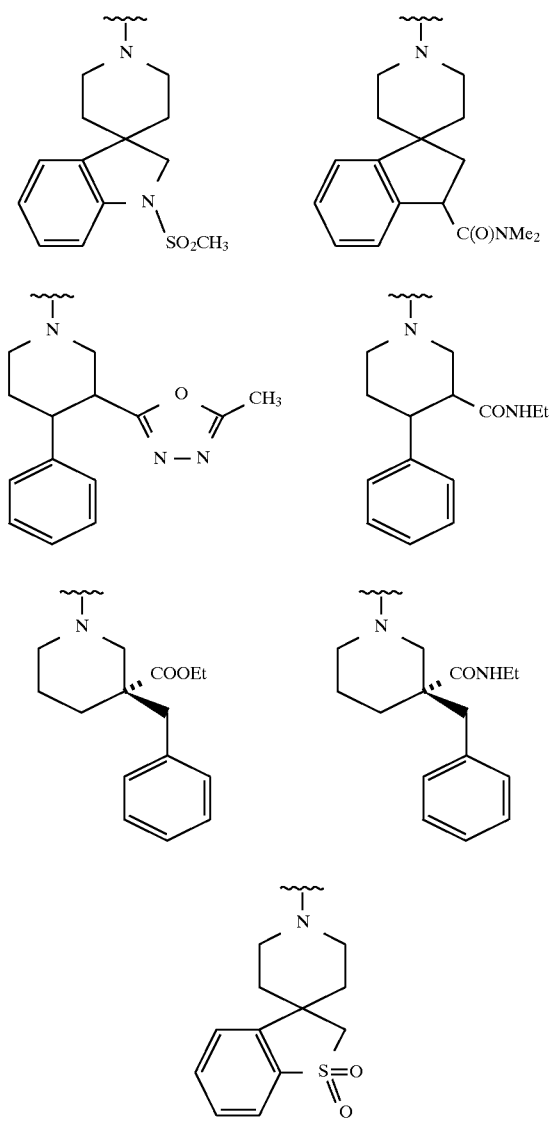

and pharmaceutically acceptable salts and individual diastereomers thereof.

Another embodiment of the most preferred compounds of the instant invention includes compounds of the formula:

wherein B is selected from the group consisting of:

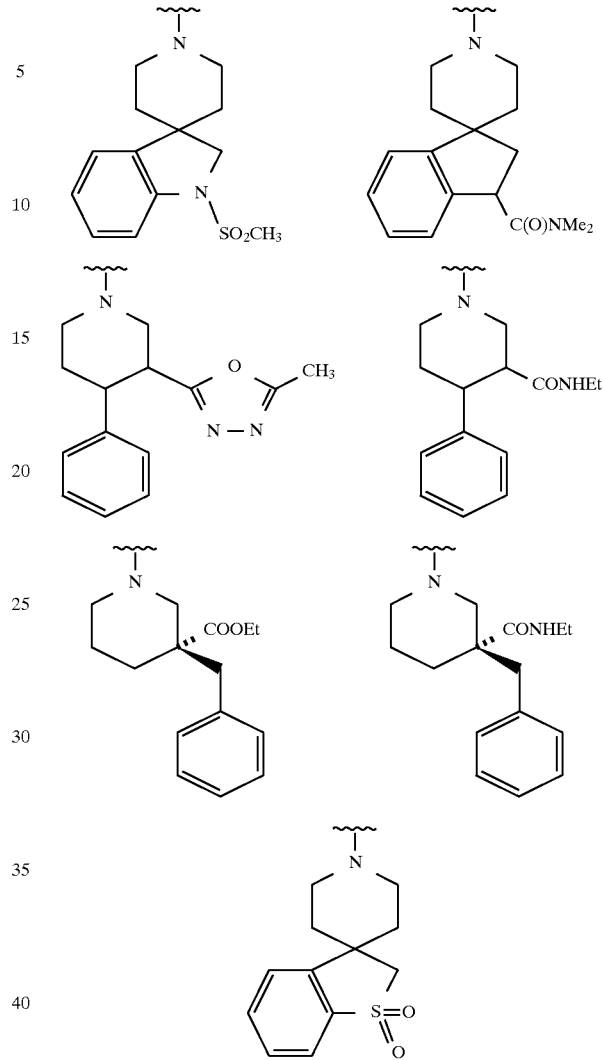

and pharmaceutically acceptable salts and individual diastereomers thereof.

Specific compounds within the instant invention include the following:

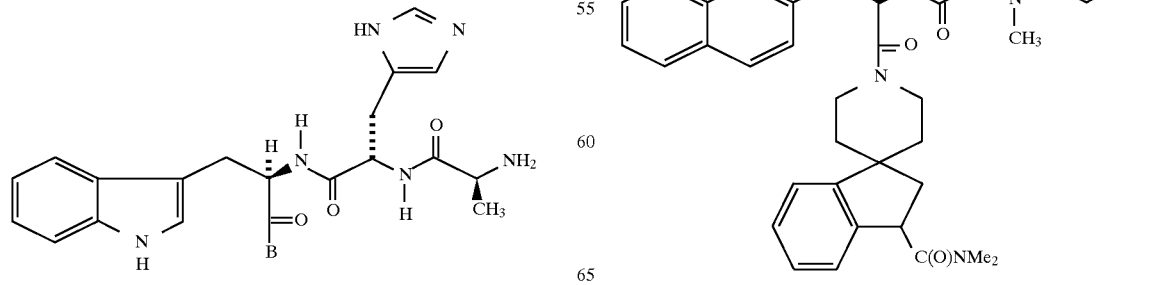

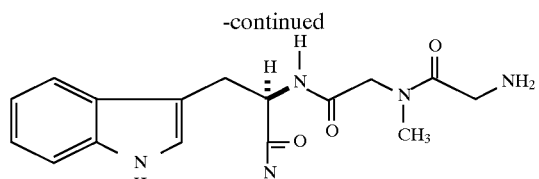
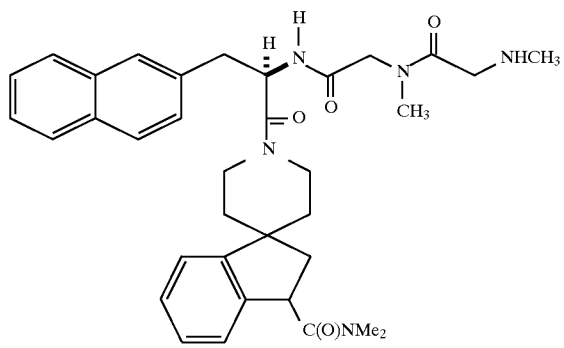
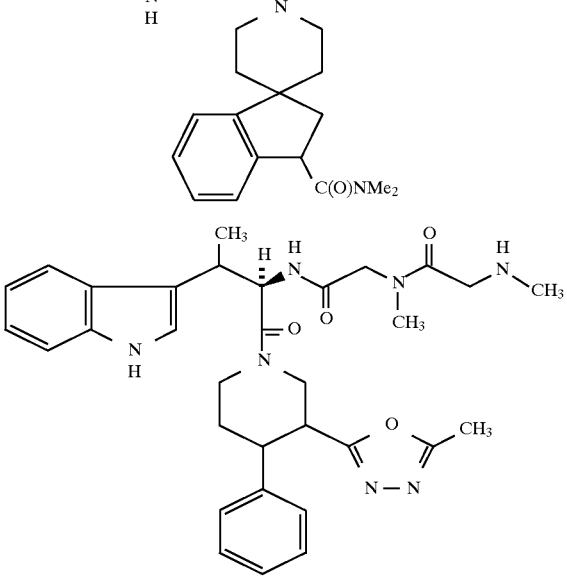
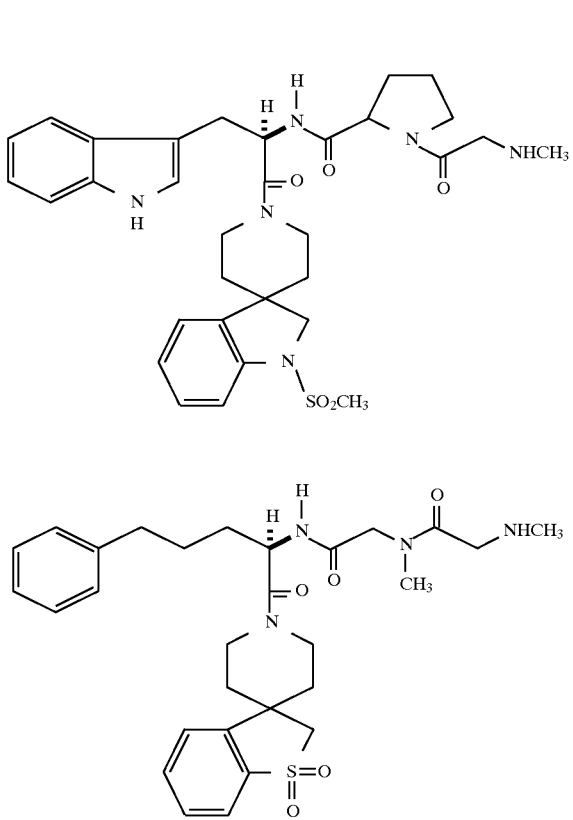
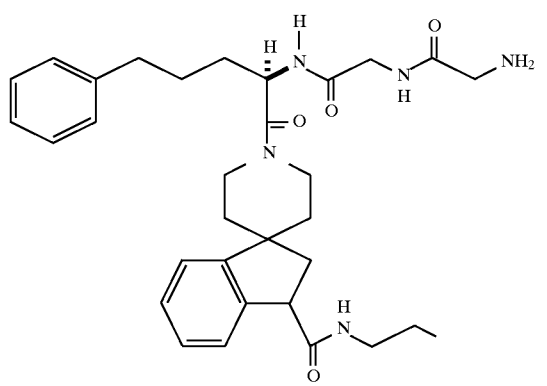

and pharmaceutically acceptable salts and individual diastereomers thereof where not otherwise specified.

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris/dimethylamino)-phosphonium hexafluorophosphate |
| calc. | calculated |
| CBZ, Cbz | Benzyloxycarbonyl |
| DCC | Dicyclohexylcarbodiimide |
| DMF | N,N-dimethylformamide |
| DMAP | 4-Dimethylaminopyridine |
| EDC | 1-(3-dimethylaminopropyl)-3-ethylcarbodi-imide hydrochloride |
| EI-MS | Electron ion-mass spectroscopy |
| Et | ethyl |
| eq. | equivalent(s) |
| FAB-MS | Fast atom bombardment-mass spectroscopy |
| HOBT, HOBt | Hydroxybenztriazole |
| HPLC | High pressure liquid chromatography |
| KHMDS | Potassium bis(trimethylsilyl)amide |
| LAH | Lithium aluminum hydride |
| LHMDS | Lithium bis(trimethylsilyl)amide |

| | |
|---|---|
| Me | methyl |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Tetramethylsilane |

The compounds of the instant invention have at least two asymmetric centers when B is:

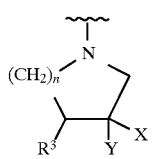

and both X and Y are groups other than hydrogen and are different from each other. Additional asymmetric centers may be present depending upon the nature of the various substituents on the molecule. Each such asymmetric center will independently produce two optical isomers and it is intended that all of the possible optical isomers and diastereomers in mixture and as pure or partially purified compounds are included within the ambit of this invention. In the case of the asymmetric center which bears the X and Y groups, in most cases, both R— and S— configurations are consistent with useful levels of growth hormone secretagogue activity. In addition configurations of many of the most preferred compounds of this invention are

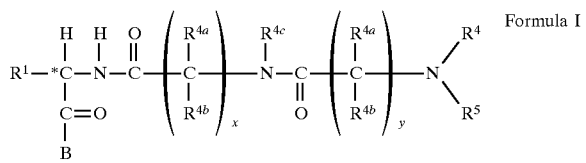

Formula I indicated. When the carbon atom in Formula I bearing an asterisk is of a defined two diastereomers result according to the absolute configuration at the carbon atom bearing the X and Y groups. These diastereomers are arbitrarily referred to as diastereomer 1 ($d_1$) and diastereomer 2 ($d_2$) in this invention and, if desired, their independent syntheses or chromatographic separations may be achieved as described herein. Their absolute stereochemistry may be determined by the x-ray crystallography of crystalline products or crystalline intermediates which are derivatized, if necessary, with a reagent containing an asymmetric center of known absolute configuration.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds of Formula I of the present invention may be carried out in sequential or convergent synthetic routes. Syntheses detailing the preparation of the compounds of Formula I in a sequential manner are presented in the following reaction schemes.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present and can be found in Greene, T, and Wuts, P. G. M., *Protective Groups in Organic Synthesis*, John Wiley & Sons, Inc., New York, N.Y. 1991. CBZ and BOC were used extensively in the synthesis, and their removal conditions are known to those skilled in the art. For example, removal of CBZ groups can be achieved by a number of methods known in the art; for example, catalytic hydrogenation with hydrogen in the presence of a nobel metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active α-Amino Acids*, Pergamon Press: Oxford, 1989). Many of the piperidines, pyrrolidines, and hexahydro-1H-azepines of Formula 2 are either commercially available or known in the literature and others can be prepared following literature methods described for analogous compounds. Some of these methods are illustrated in the subsequent schemes. The skills required in carrying out the reaction and purification of the resulting reaction products are known to those in the art. Purification procedures includes crystallization, normal phase or reverse phase chromatography.

SCHEME 1

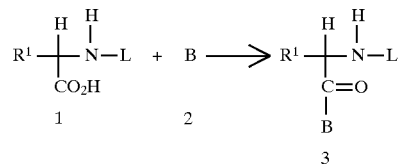

Intermediates of Formula 3 may be synthesized as described in Scheme 1. Coupling of amine of Formula 2, whose preparations are described later if they are not commercially available, to protected amino acids of Formula 1, wherein L is a suitable protecting group, is conveniently carried out under standard peptide coupling conditions.

SCHEME 2

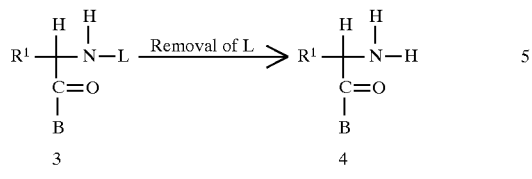

Conversion of 3 to intermediate 4 may be carried out as illustrated in Scheme 2 by removal of the protecting group L (CBZ, BOC, etc.)

SCHEME 3

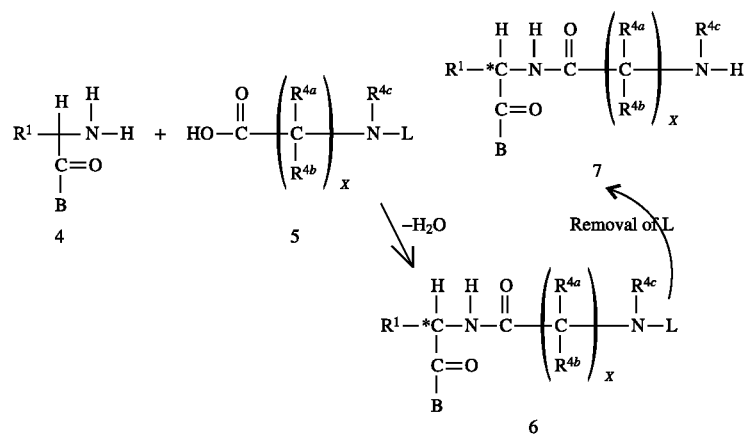

Intermediates of Formula 6, wherein L is a protecting group may be prepared as shown in Scheme 3 by coupling intermediates of Formula 4 to protected amino acids of Formula 5 under the standard peptide coupling reaction conditions. The amino acids 5, as amino acid 1, are either commercially available or can be synthesized by routine methods. The removal of L in 6 to afford 7 can be carried out as noted above.

SCHEME 4

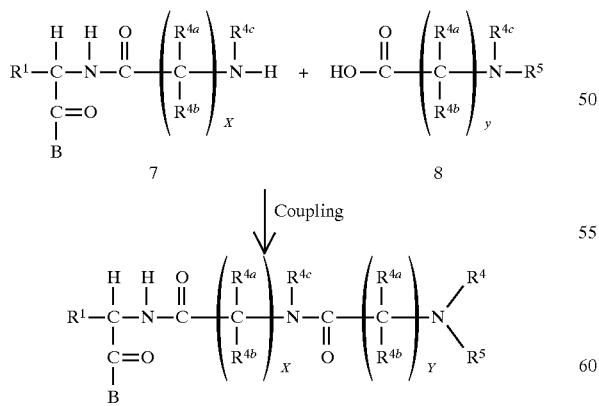

Elaboration of 7 to compounds of Formula 1 can be accomplished as shown in Scheme 4 by coupling intermediates of Formula 7 to amino acids of Formula 8 under standard peptide coupling reaction conditions.

SCHEME 5

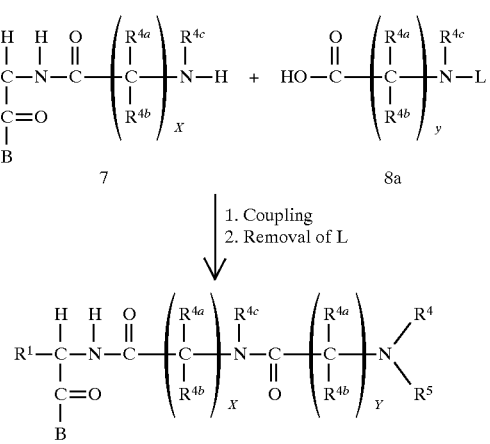

As shown in Scheme 5, if $R^4$ or $R^5$ is a hydrogen then the protected amino acids 8a are employed in the coupling reaction wherein L is a protecting group as defined above. The removal of L in 10 to afford I can be carried out as noted above.

SCHEME 6

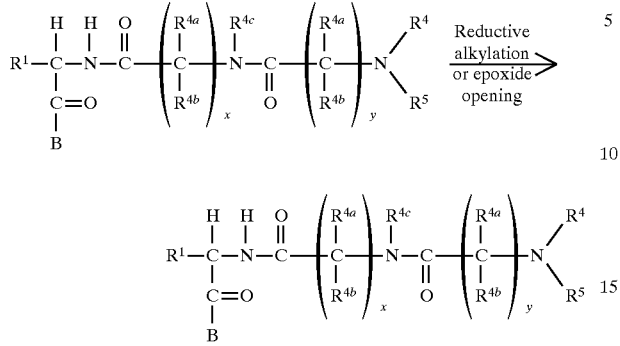

(where R⁴ is substituted/unsubstituted alkyl)

Compounds of Formula I wherein $R^4$ and/or $R^5$ is a hydrogen may be further elaborated to new Compounds I which are substituted on the amino group as depicted in Scheme 6. Reductive alkylation of I with an aldehyde is carried out under conditions known in the art; for example, by catalytic hydrogenation with hydrogen in the presence of platinum, palladium, or nickel catalysts or with chemical reducing agents such as sodium cyanoborohydride in a protic solvent such as methanol or ethanol in the present of catalytic amount of acid. Alternatively, a similar transformation can be accomplished via an epoxide opening reaction.

The compounds of general Formula I of the present invention may also be prepared in a convergent manner as described in Schemes 7, 8 and 9.

SCHEME 7

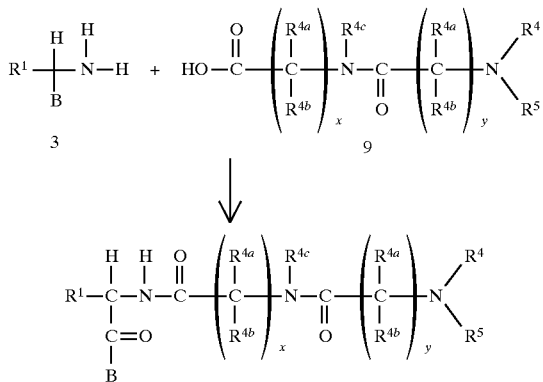

Intermediates of Formula 9 can be synthesized by well documented methods in the literature. Elaboration of 9 to compounds of Formula 1 can be accomplished as shown in Scheme 7 by coupling intermediates of Formula 3 to amino acids of Formula 9 under standard peptide coupling reaction conditions.

SCHEME 8

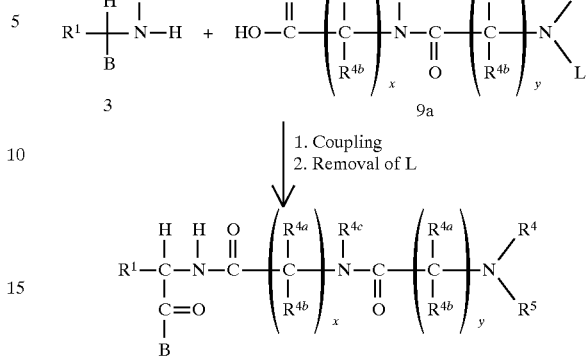

As shown in Scheme 8, if $R^4$ or $R^5$ is a hydrogen then the protected amino acids 9a are employed in the coupling reaction wherein L is a protecting group as defined above. The removal of L to afford I can be carried out as noted above. When $R^4$ and/or $R^5$ is H, substituted alkyl groups may be optionally added to the nitrogen atom as described in Scheme 4.

SCHEME 9

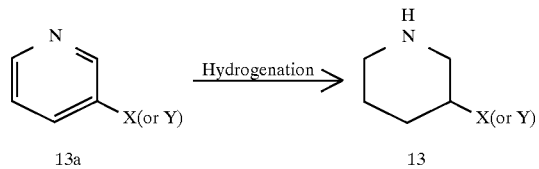

3-Monosubstituted piperidines of formula 13 can be prepared by the reduction of pyridine derivatives or their salts by hydrogenation in a suitable organic solvent such as water, acetic acid, alcohol, e.g. ethanol, or their mixture, in the presence of a noble metal catalyst such as platinum or an oxide thereof on a support such as activated carbon, and conveniently at room temperature and atmospheric pressure or under elevated temperature and pressure. 3-Monosubstituted piperidines can also be prepared by modification of the X or Y moiety of the existing 3-monosubstituted piperidines.

SCHEME 9A

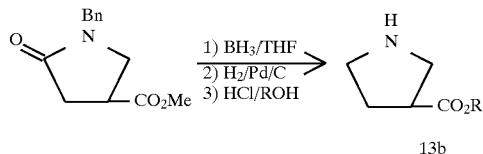

3-Monosubstituted pyrrolidines are commercially available or can be conveniently prepared by literature procedures. Shown in Scheme 9A is an example of the preparation of these compounds via pyrrolidine-3-carboxylic acid ester. The commercially available compound methyl 1-benzyl-4-oxo-3-pyrrolidinecarboxylate is reduced by borane (*J. Chem. Soc.*, 24, 1618–1619). Removal of the benzyl group by catalytic hydrogenolysis followed by ester exchange in an appropriate alcohol medium such as ethyl alcohol in the presence of acid gave the compound 13b. The ester functionality may be further modified through conventional chemistry to other groups as defined by X. 3-Monosubstituted pyrrolidines may also be prepared by catalytic hydrogenation of 3-substituted pyrroles.

SCHEME 9B

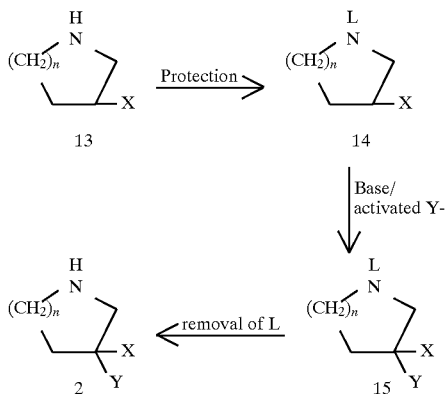

13c

Hexahydro-1H-azepines are commercially available or may be prepared by the literature procedure. Hexahydro-1H-azepine-3-carboxylic acid (Krogsgaard-Larsen, P. et al., *Acta. Chem. Scand.*, B32, 327, (1978)) is esterified in an alcohol solvent in the presence of acid. The ester functionality may be further modified through conventional chemistry to other groups within the definition of X.

SCHEME 10

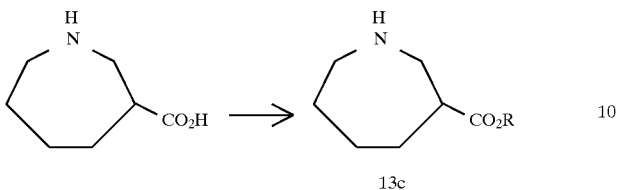

Illustrated in Scheme 10 is a general way to prepare di-substituted piperidines, pyrrolidines, and hexahydro-1H-azepines. Compounds of Formula 13 wherein X is an electron withdrawing group such as —CN, —$CO_2R_8$, where $R_8$ is alkyl, aryl, and ($C_1$–$C_4$alkyl)aryl are known compounds or may be prepared by methods analogous to those used for the preparation of such known compounds. The secondary amine of compounds of Formula 13 may be first protected by a protecting group L such as BOC and CBZ using the conventional techniques. Introduction of the Y substitution can be achieved by first reacting compounds of Formula 14 with a strong base such as lithium bis(trimethylsilyl)amide, lithium diisopropylamide following by addition of alkylating or acylating reagents such as alkyl halides, aryl alkyl halides, acyl halides, and haloformates in a inert solvent such as THF at temperatures from –100° to room temperature. Thio derivatives where the sulfur is attached directly to an alkyl or an aryl group can be prepared similarly by reacting with a disulfide. The halides used in these reactions are either commercially available or known compounds in the literature or may be prepared by methods analogous to those used for the preparation of known compounds. The protecting group L in compounds of formula 15 may be removed with conventional chemistry to give compounds of Formula 2.

SCHEME 11

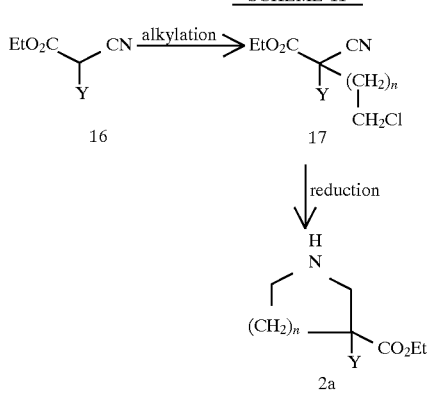

Alternative ways of preparing compounds of Formula 2 include construction of the ring itself (Jacoby, R. L. et al, *J. Med. Chem.*, 17, 453–455, (1974)). Alkylation of the cyanoacetates of general formula 16, which are commercially available or may be prepared from literature procedures, with alkyl dihalides such as 1-bromo-2-chloroethane or 1-bromo-3-chloropropane yields the chloride 17. Reduction of the nitrites 17 by borane or by hydrogenation using Raney Ni as a catalyst gives the corresponding primary amines, which upon refluxing in ethanol to give compounds of Formula 2a.

SCHEME 12

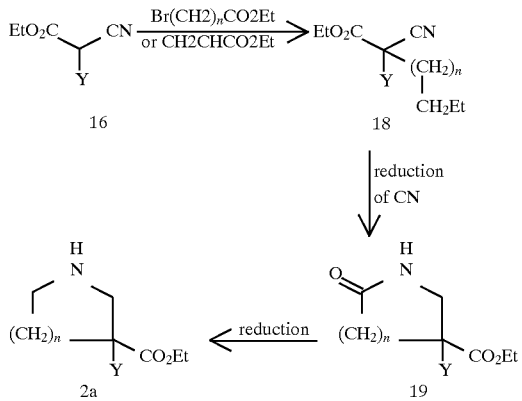

Alternatively, the cyanoacetates of general formula 16 may be alkylated with an ethoxycarbonylalkyl bromide or reacted with ethyl acrylate to give compounds of Formula 18. Reduction of the nitriles 18 by borane or by hydrogenation using Raney Ni as a catalyst gives the corresponding primary amines, which upon refluxing in ethanol gives lactam 19. Reduction of the lactam 19 by borane gives compounds of Formula 2a.

SCHEME 13

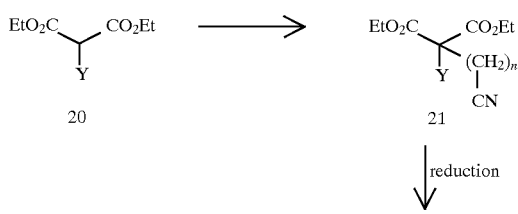

-continued
SCHEME 13

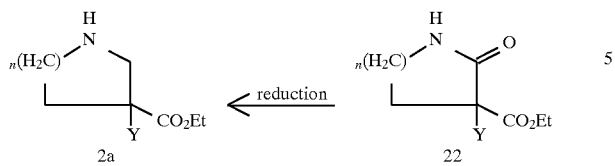

Alternatively, a malonate of general formula 20 may be alkylated with cyanoalkyl bromide or can be reacted with acrylonitrile to form compounds of formula 21. Reduction of the nitriles 21 by borane or by hydrogenation using Raney Ni as a catalyst gives the corresponding primary amines, which upon refluxing in ethanol gives lactam 22. Reduction of the lactam 22 by borane gives compounds of formula 2a.

SCHEME 14

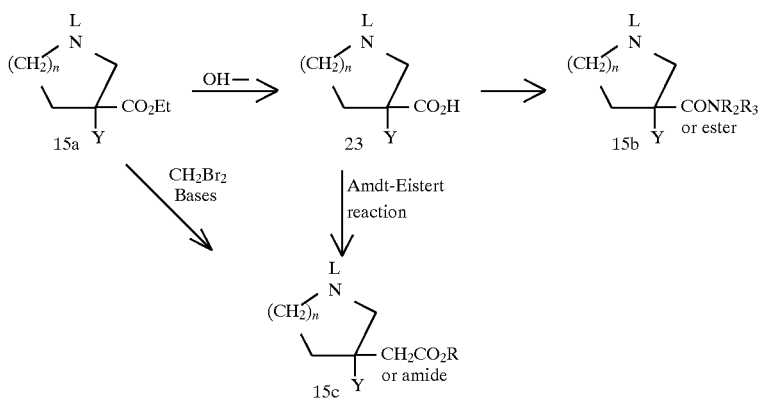

The X, Y functionalities in compounds of general structure 15 may be further elaborated to groups not accessible by direct alkylation. For example in Compound 15 when X=CO$_2$Et the ester (provided that this is the only ester group in the molecule) can be saponified to the carboxylic acid, which can be further derivatized to amides or other esters. The carboxylic acid can be converted into its next higher homologue, or to a derivative of the homologous acid, such as amide or ester by an Arndt-Eistert reaction. Alternatively, the ester can be directly homologated by the protocol using ynolate anions described by C. J. Kowalski and R. E. Reddy in *J. Org. Chem.*, 57, 7194–7208 (1992). The resulting acid and/or ester may be converted to the next higher homologue, and so on and so forth. The protecting group L may be removed through conventional chemistry.

SCHEME 15

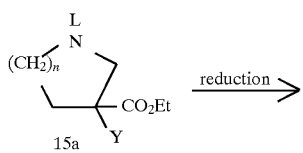

-continued
SCHEME 15

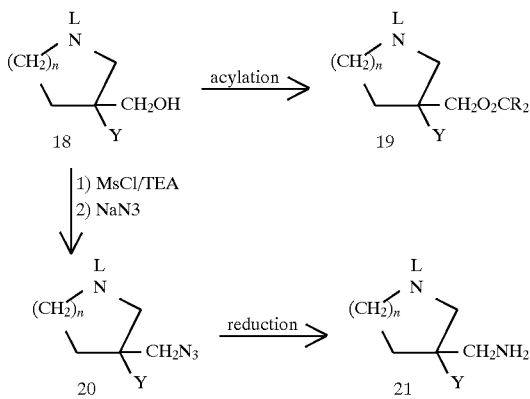

The ester in 15a may be reduced to an alcohol 18 in a suitable solvent such as THF or ether with a reducing agent such as DIBAL-H and conveniently carried out at temperatures from −100° C. to 0° C. The alcohol may be acylated to Compound 19 in a suitable solvent such as dichloromethane using an acyl halide or acid anhydride in the presence of a base such as triethyl amine (TEA). The hydroxy group in 18 may also be converted to a good leaving group such as mesylate and displaced by a nucleophile such as cyanide, a thiol or an azide. Reduction of the azide in compounds of Formula 20 to an amine 21 can be achieved by hydrogenation in the presence of a noble metal such as palladium or its oxide or Raney nickel in a protic solvent such as ethanol. The nitrile can be reduced to afford the homologous amine. The amine of Formula 21 may be further elaborated to amides, ureas sulfonamides as defined by X through conventional chemistry. The protecting group L may be removed through conventional chemistry.

SCHEME 16

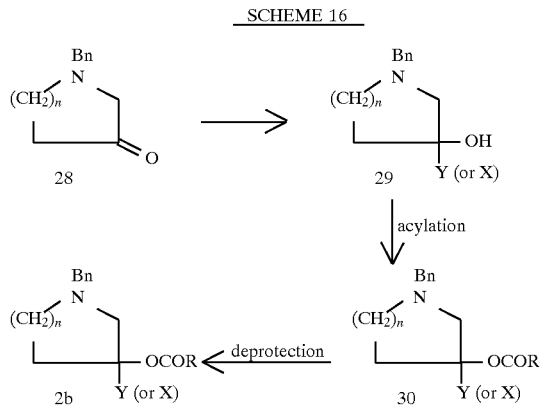

In cases where oxygen is directly attached to the ring, a convenient method involves the addition reaction by an activated form of an alkyl, aryl, alkylaryl group, such as lithium reagent, Grignard reagents, and the like with a ketone of general formula 28, which is commercially available. Further derivatization of the resulting hydroxy group by acylation, sulfonylation, alkylation, and the like gives compounds as defined by Y or X through conventional chemistry. Removal of the benzyl protective group may be carried out under the usual conditions to give compounds of general formula 2b. Shown in Scheme 16 is a general example of acylations.

SCHEME 17

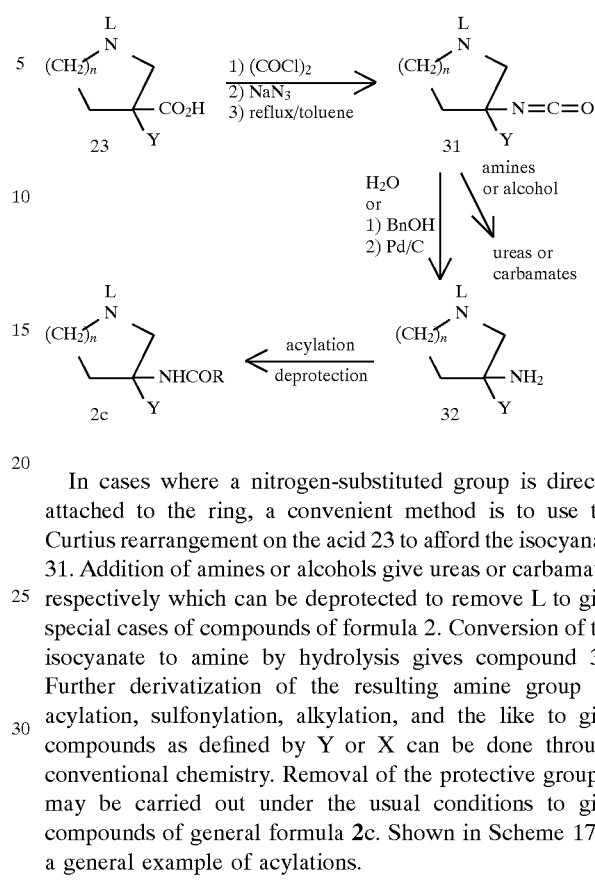

In cases where a nitrogen-substituted group is directly attached to the ring, a convenient method is to use the Curtius rearrangement on the acid 23 to afford the isocyanate 31. Addition of amines or alcohols give ureas or carbamates respectively which can be deprotected to remove L to give special cases of compounds of formula 2. Conversion of the isocyanate to amine by hydrolysis gives compound 32. Further derivatization of the resulting amine group by acylation, sulfonylation, alkylation, and the like to give compounds as defined by Y or X can be done through conventional chemistry. Removal of the protective group L may be carried out under the usual conditions to give compounds of general formula 2c. Shown in Scheme 17 is a general example of acylations.

SCHEME 18

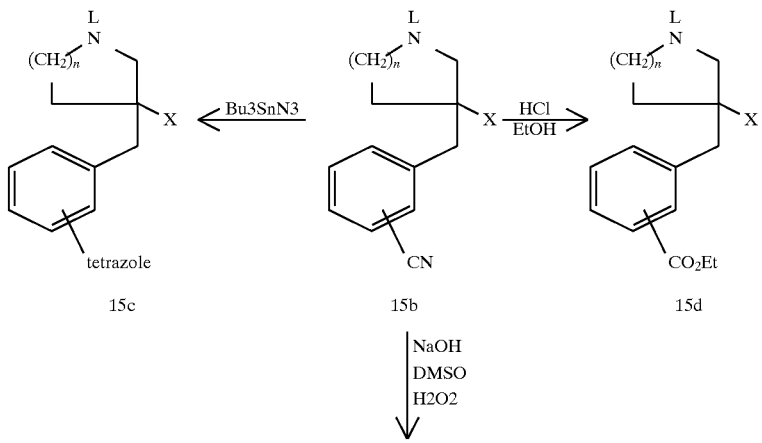

SCHEME 18 -continued

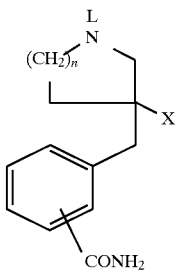

15e

For compounds that are not readily obtainable by direct alkylation as shown in Scheme 10, modifications of easily obtainable compounds of general formula 15 may be conducted to achieve the desired substitution through conventional chemistry. For example, compounds with Y being hydroxybenzyl may be prepared by demethylation of the corresponding compound wherein Y is methoxybenzyl. Similarly, compounds with Y being aminobenzyl may be prepared by reduction of the corresponding compound wherein Y is nitrobenzyl. Shown in Scheme 18 is an example of a procedure that uses nitrile as a starting point for the preparation of compounds with different substitutions. Removal of the protective group L gives compounds of general formula 2 as described in Scheme 10.

Compounds of the general formula 2 prepared in this way are racemic when X and Y are not identical. Resolution of the two enatiomers can be conveniently achieved by classical crystallization methods by using a chiral acid such as L- or D-tartaric acid, (+) or (−)-10-camphorsulfonic acid in a suitable solvent such as acetone, water, alcohol, ether, acetate or their mixture. Alternatively, the racemic amine 2 can be reacted with a chiral auxiliary such as (R) or (S)—O—acetylmandelic acid followed by chromatographic separation of the two diastereomers, and removal of the chiral auxiliary by hydrolysis. Alternatively asymmetric alkylation can also be utilized for the synthesis of optically active intermediate by introducing a removable chiral auxiliary in X or in place of L with subsequent chromatographic separation of diastereomers.

In cases where a sulfide is present in the molecule, it may be oxidized to a sulfoxide or to a sulfone with oxidizing agents such as sodium periodate, m-chloroperbenzoic acid or Oxone® in an solvent such as dichloromethane, alcohol or water or their mixtures.

The compounds of the present invention may also be prepared from a variety of substituted natural and unnatural amino acids of formulas 46. The preparation of many of these acids is described in U.S. Pat. No. 5,206,237. The preparation of these intermediates in racemic form is accomplished by classical methods familiar to those skilled in the art (Williams, R. M. "Synthesis of Optically Activeα-Amino Acids" Pergamon Press: Oxford, 1989; Vol. 7). Several methods exist to resolve (DL)-amino

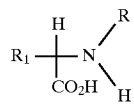

acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in J. Am. Chem. Soc. 1989, 111, 6354–6364.

When it is desirable to synthesize these intermediates in optically pure form, established methods include: (1) asymmetric electrophilic amination of chiral enolates (J. Am. Chem. Soc. 1986, 108, 6394–6395, 6395–6397, and 6397–6399), (2) asymmetric nucleophilic amination of optically active carbonyl derivatives, (J. Am. Chem. Soc. 1992, 114, 1906; Tetrahedron Lett. 1987, 28, 32), (3) diastereoselective alkylation of chiral glycine enolate synthons (J. Am. Chem. Soc. 1991, 113, 9276; J. Org. Chem. 1989, 54, 3916), (4) diastereoselective nucleophilic addition to a chiral electrophilic glycinate synthon (J. Am. Chem. Soc. 1986, 108, 1103), (5) asymmetric hydrogenation of prochiral dehydroamino acid derivatives ("Asymmetric Synthesis, Chiral Catalysis; Morrison, J. D., Ed; Academic Press: Orlando, Fla, 1985; Vol 5), and (6) enzymatic syntheses (Angew. Chem. Int. Ed. Engl. 1978, 17, 176).

SCHEME 19

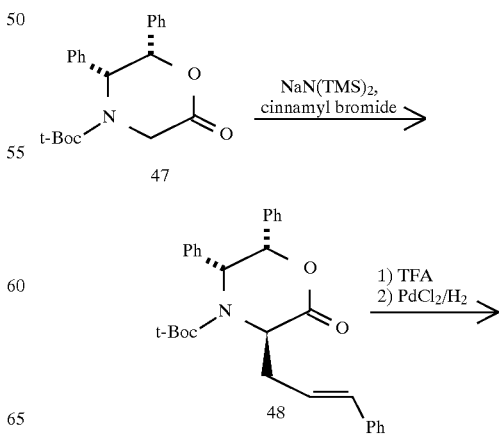

-continued
SCHEME 19

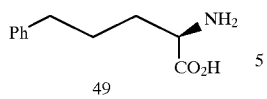

49

For example, alkylation of the enolate of diphenyloxazinone 47 (J. Am. Chem. Soc. 1991, 113, 9276) with cinnamyl bromide in the presence of sodium bis(trimethylsilyl)amide proceeds smoothly to afford 48 which is converted into the desired (D)-2-amino-5-phenylpentanoic acid 49 by removing the N-t-butyloxycarbonyl group with trifluoroacetic acid and hydrogenation over a $PdCl_2$ catalyst (Scheme 19).

SCHEME 20

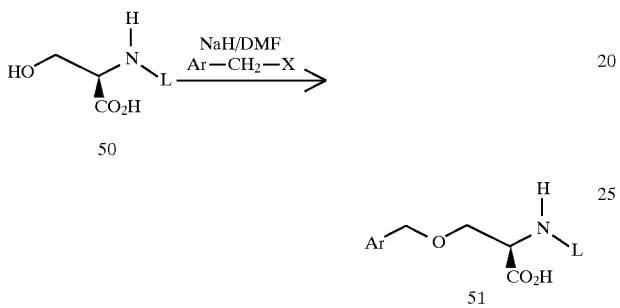

Intermediates of formula 46 which are O-benzyl-(D)-serine derivatives 51 are conveniently prepared from suitably substituted benzyl halides and N-protected-(D)-serine 50. The protecting group L is conveniently a BOC or a CBZ group. Benzylation of 64 can be achieved by a number of methods well known in the literature including deprotonation with two equivalents of sodium hydride in an inert solvent such as DMF followed by treatment with one equivalent of a variety of benzyl halides (Synthesis 1989, 36) as shown in Scheme 20.

The O-alkyl-(D)-serine derivatives may also be prepared using an alkylation protocol. Other methods that could be utilized to prepare (D)-serine derivatives of formula 51 include the acid catalyzed benzylation of carboxyl protected intermediates derived from 50 with reagents of formula $ArCH_2OC(=NH)CCl_3$ (O. Yonemitsu et al., Chem. Pharm. Bull. 1988, 36, 4244). Alternatively, alkylation of the chiral glycine enolates (J. Am. Chem. Soc. 1991, 113, 9276; J. Org. Chem. 1989, 54, 3916) with $ArCH_2OCH_2X$ where X is a leaving group affords 51. In addition D,L-O-aryl(alkyl) serines may be prepared and resolved by methods described above.

The spiro piperidines of formula 52 may be prepared by a number of methods, including the syntheses described below.

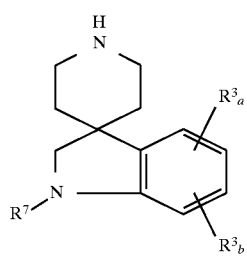

52

SCHEME 21

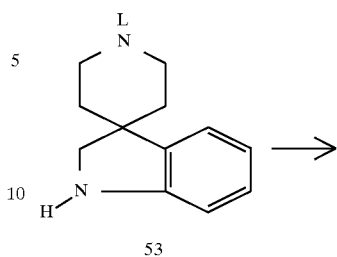

As shown in Scheme 21, the spiropiperidine of formula 43, wherein L is a defined protecting group, is synthesized by methods that are known in the literature (for example H. Ong et al J. Med. Chem. 1983, 23, 981–986). The indoline nitrogen of 54, wherein L is a protecting group such as methyl or benzyl, can be reacted by with a variety of electrophiles to yield spiro piperidines of formula 54, wherein $R_9$ can be a variety of functionalities. Compound 54 can be reacted with, for example, isocyanates in an inert solvent like dichloromethane to yield urea derivatives, chloroformates in an inert solvent such as dichloromethane to yield carbamates, acid chlorides, anhydrides, or acyl imidazoles to generate amides, sulfonyl chlorides to generate sulfonamides, sulfamyl chlorides to yield sulfamides. Also, the indoline nitrogen of 53 can be reductively alkylated with aldehydes with conditions known in the art. When the aldehyde used in the reductive amination reaction is a protected glyoxylic acid of structure HCOCOOM, wherein M is a defined protecting group, M can be removed from the product and further derivatized. Alternatively, 53 can be reacted with epoxides to produce 53, wherein $R^9$ is β-hydroxy-substituted alkyl or arylalkyl groups. The indoline 53 can also be transformed to compounds of formula 54, wherein $R^9$=phenyl or substituted phenyl, heteroaryl or substituted heteroaryl, by carrying out the reacting 53 with a fluoro phenyl or fluoro heteroaryl reagent. This chemistry is detailed by H. Ong et al J. Med. Chem. 1983, 23, 981–986.

SCHEME 22

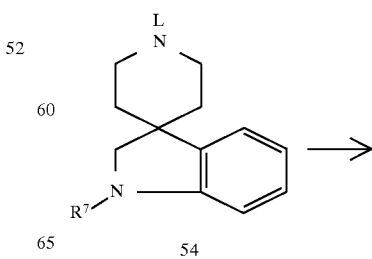

54

-continued
SCHEME 22

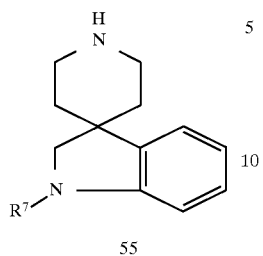

55

The spiro piperidine intermediate 54 (L=Me or Bn), wherein $R^7$ is hydrogen or most of the derivatives described above, can be demethylated or debenzylated to produce 55, wherein $R^9$ is hydrogen or most of the derivatives described above, as shown in Scheme 22. For compounds of formula 54, wherein L=Me, demethylation can be carried out by a number methods familiar those skilled in the art. For example, demethylation of 54 be accomplished by reacting it with cyanogen bromide and potassium carbonate in an inert solvent solvent such as dichloromethane to yield a cyanamide which can reduced to give 55 by treatment with lithium aluminum hydride in refluxing tetrahydrofuran, refluxing strong acid like aqueous hydrochloric acid, or with Grignard reagents like methyl magnesium bromide. Alternatively, demethylation of 54 can be effected with the ACE-Cl method as described in R. Olofson et al. *J. Org. Chem.* 1984, 49, 2795 and references therein. For intermediates of formula 54, wherein L=Bn, removal of benzyl group can be accomplished by reductive methods including hydrogenation in the presence of platinum or palladium catalyst in a protic solvent like methanol. Alternatively, debenzylation of 54, L=Bn, can be effected with the ACE-Cl method as described in R. Olofson et al. *J. Org. Chem.* 1984, 49, 2795 and references therein.

SCHEME 23

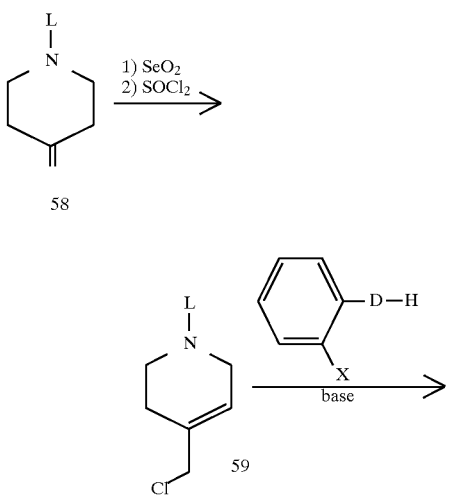

-continued
SCHEME 23

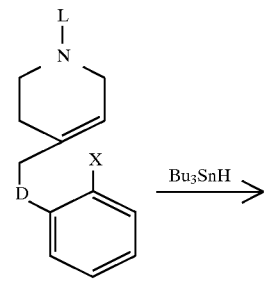

60

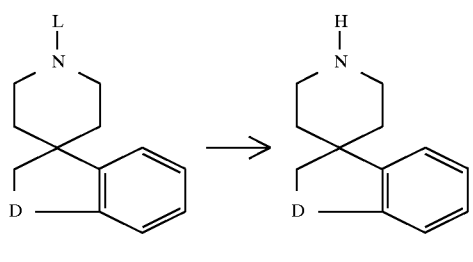

57      56

D = O, S, $NR^7$, X = halides, Se, S

The Spiro heterocyclic compounds of formula 56 can be prepared by a number of methods, including the syntheses as described in Scheme 23. Allylic oxidation of the protected piperidine 58 is accomplished by classical methods familiar to those skilled in the art (Rabjohn, N. *Org. React.* 1976, 24, 261). The resulting allylic alcohol is treated with thionyl chloride in an inert solvent such as benzene to provide the corresponding chloride 59. When D=O or S, the alkylation is carried out in DMF or acetone as solvent with potassium carbonate as a base, and when D=$NR^7$ ($R^7$=H, alkyl, aryl, acyl, sulfonyl, carbamate) the reaction is carried out with sodium hydride as a base in an inert solvent such as THF to afford the cyclization precursor 60. When L is a defined protecting group, compound 60 can be cyclized by a number methods familiar to those skilled in the art. For example, cyclization of 60 can be accomplished by reaction with tributyltin hydride (Curran, D. P. *Synthesis* 1988, 417 and 489) in an inert solvent such as benzene to yield 57. Alternatively, compound 57 (D=$NR_9$) can be prepared by the method shown in Schemes 24 and 25.

SCHEME 24

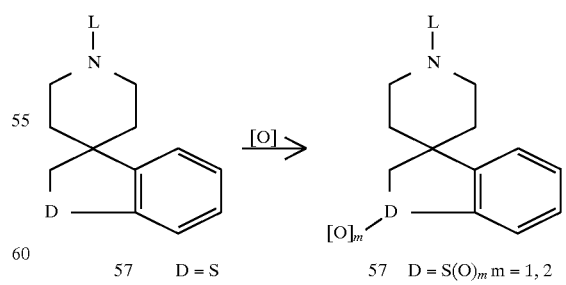

57   D = S      57   D = S(O)$_m$ m = 1, 2

As shown in Scheme 24, when D=S, compound 57 can be oxidized to the sulfoxide 57 (n=1) and the sulfone 57 (n=2) by many oxidizing agents. For example, sodium periodate is often used for the synthesis of sulfoxides and Oxone is used for the synthesis of sulfones. Removal of the protecting group provides the amine 56 which then can be incorporated into a growth hormone secretagogue via the chemistry detaileds in Scheme 1 and 8 shown above which utilize generic intermediate 2.

Compounds of formula I wherein $R^4$ and $R^5$ are each hydrogen can be further elaborated by reductive alkylation with an aldehyde by the aforementioned procedures or by alkylations such as by reaction with various epoxides. The products, obtained as hydrochloride or trifluoroacetate salts, are conveniently purified by reverse phase high performance liquid chromatogrphy (HPLC) or by recrystallization.

SCHEME 26

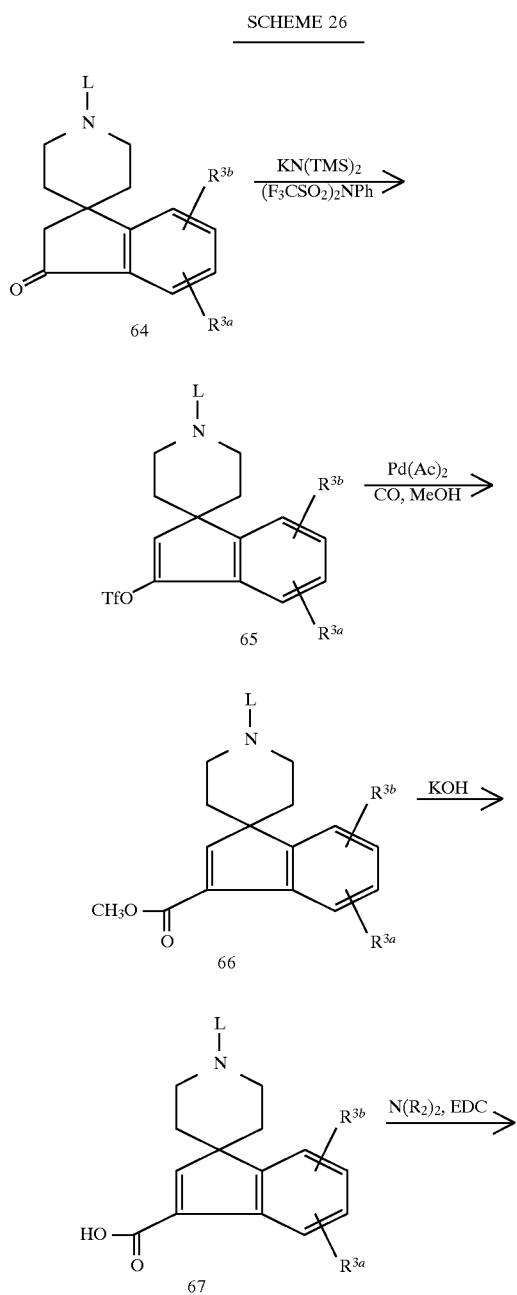

-continued
SCHEME 26

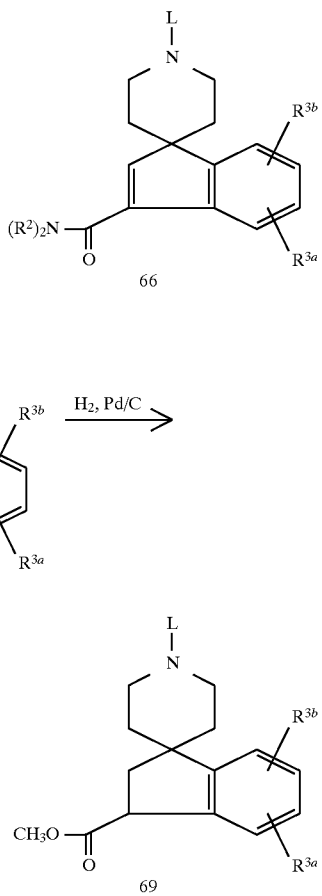

Homologation of the spiroindanone 64 provides easy access to spiroindanyl intermediates containing acid and ester groups. This chemistry is described in Scheme 26. Treatment of 64 with a base in an inert solvent such as THF followed by the addition of a triflating agent provides the enol triflate. Carboxylation of the enol triflate according to the procedure of Cacchi, S. *Tetrahedron Letters*, 1985, 1109–1112 provides the ester 66. The protecting group can then be removed as described above and the resulting amine can be incorporated into the subject compound via the chemistry depicted in Schemes 1 and 8. A compound containing an acid function is readily available via saponification of the ester group as the final step of the synthesis.

Saponification of the ester of 66 provides an acid which can be conveniently derivatized as for example reaction with an amine in the presence of a coupling agent such as EDC gives amides which can then be incorporated into final compounds following the chemistry detailed in Schemes 1 and 8.

Hydrogenation of 66 using a palladium catalyst in an inert solvent provides the saturated compounds which can then either be derivatized as above or carried on to the final products via the chemistry described in Schemes 1 and 8. The ester may also be reduced to a primary alcohol with LAH and to a aldehyde with DIBALH. Reductive alkylation of the aldehyde with ammonium acetate and sodium cyanoborohydride affords an amino methyl analog. These hydroxymethyl and aminomethyl analogs may then be further reacted to afford additional growth hormone secretagogues of the general formula I. Chiral acids are available by a variety of methods known to those skilled in the art including asymmetric catalytic hydrogenation and resolution of a pair of diastereomeric salts formed by reaction with a chiral amine such as D or L α-methylbenzylamine. The absolute stereochemistry can be determined in a number of ways including X-ray crystallography of a suitable crystalline derivative.

Spiroindane intermediates, for incorporation into growth hormone secretagogues, can be further elaborated in the benzylic position by the chemistry detailed in the following schemes.

SCHEME 27

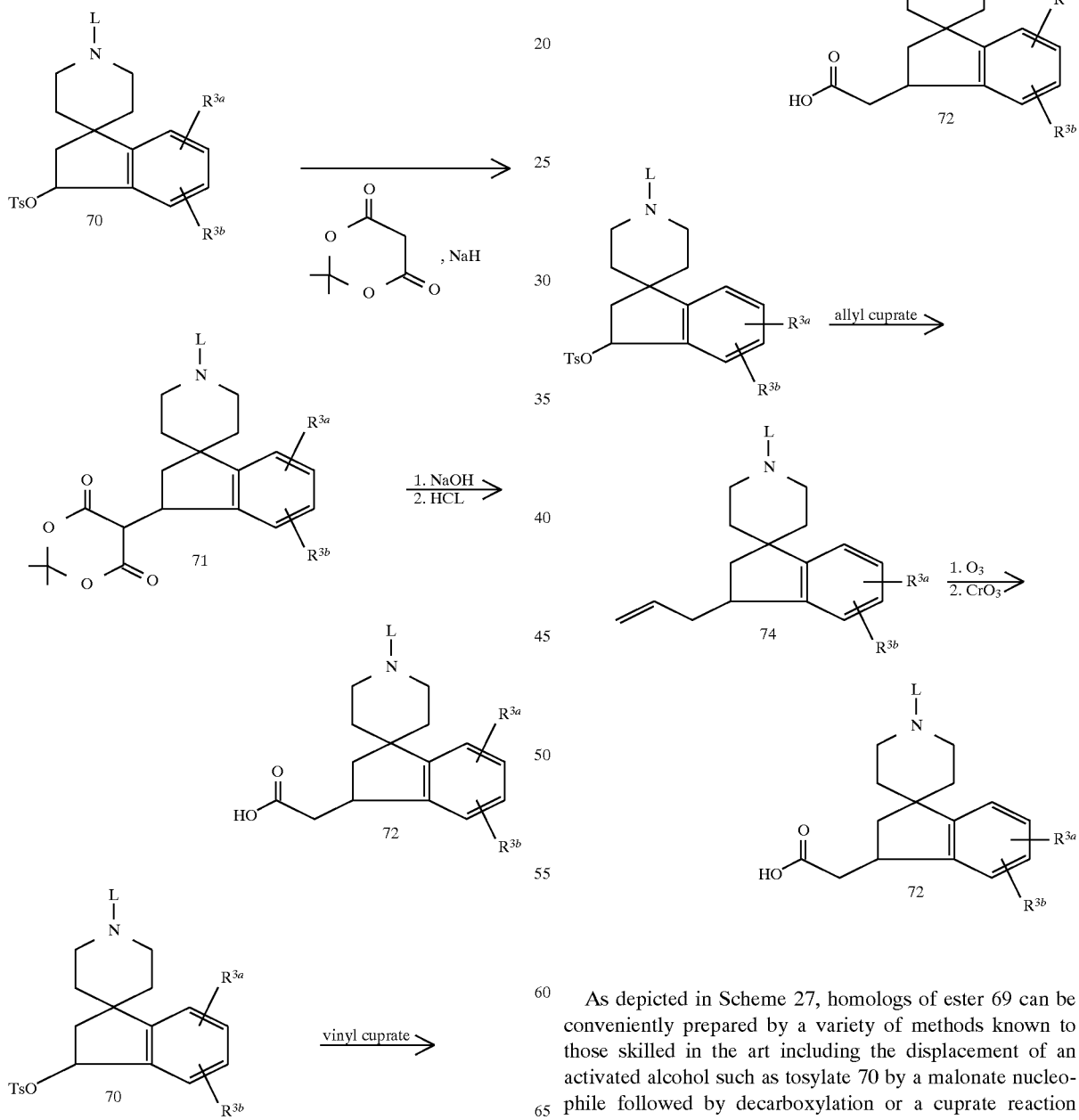

-continued
SCHEME 27

As depicted in Scheme 27, homologs of ester 69 can be conveniently prepared by a variety of methods known to those skilled in the art including the displacement of an activated alcohol such as tosylate 70 by a malonate nucleophile followed by decarboxylation or a cuprate reaction followed by the adjustment of the chain length or oxidation state as appropriate.

SCHEME 28

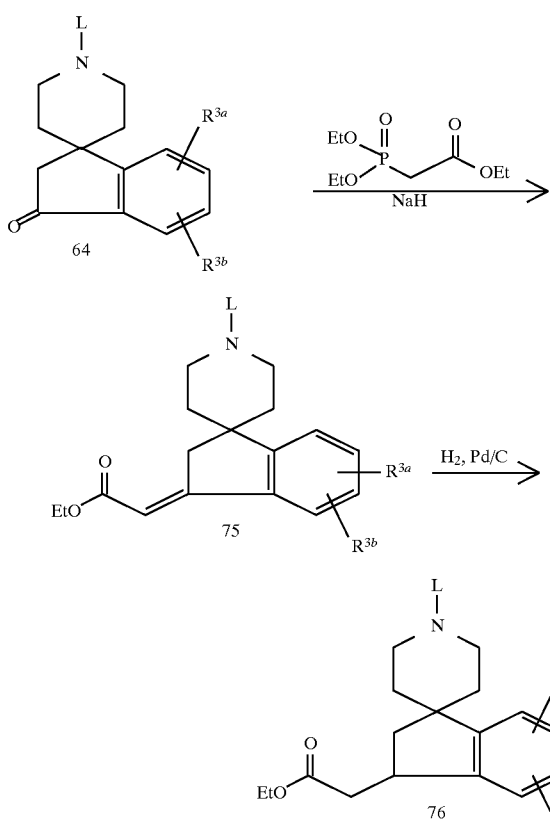

Alternatively the reaction of spiroindanone 64 with Wittig or Emmons reagents also provides access to homologs of ester 69. The chemistry is described in Scheme 28. Treatment of triethylphosphite-acetate with a base in an inert solvent such as THF followed by the addition of ketone 64 provides the unsaturated ester 75. Hydrogenation of 75 using a palladium catalyst in an inert solvent provides the saturated ester 76. The protecting group can then be removed as described above and the resulting amine can be incorporated into a final compound via the chemistry described in Schemes 1 and 8. A secretagogue containing an acid function can be obtained via saponification of the ester function as the final step of the synthesis.

Chiral esters and acids are available by a variety of methods known to those skilled in the art including asymmetric catalytic hydrogenation, chomatographic resolution of a pair of diastereomers, and via crystallization of salts formed from chiral amines such as D or L-α-methylbenzylamine. The absolute stereochemistry can be determined in a number of ways including X-ray crystallography of a suitable crystalline derivative.

The ester can be reduced to an alcohol by treatment with LAH and to an aldehyde with DIBALH. Reductive alkylation of the aldehyde with ammonium acetate and sodium cyanoborohydride affords an amino methyl analog. These hydroxymethyl and aminomethyl analogs may then be further reacted to afford additional growth hormone secretagogues of the general formula 1.

Saponification of ester 44 provides an acid which can be conveniently derivatized as for example reaction with an amine in the presence of a coupling reagent such as EDC gives amides which can be incorporated into a secretagogue as detailed in Schemes 1 and 8.

Homologation of ester 44 is possible using a variety of methods known to those skilled in the art including the method described in *J. Org. Chem.* 1992, 57 7194–7208.

SCHEME 29

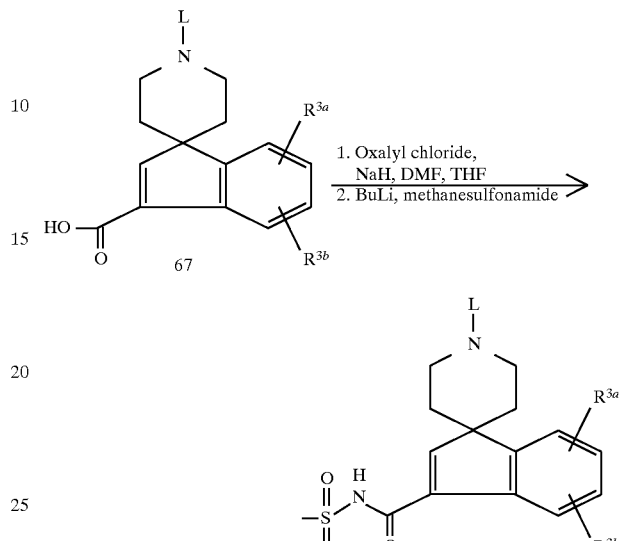

As shown in Scheme 29, a variety of acid equivalents can also be incorporated into the spiroindane intermediates for example acylsulfonamides are readily available from acids such as 67 and 72. Treatment of the spiroindane acid with a base in an inert solvent such as THF followed by the addition of oxalyl chloride provides an acid chloride which is then treated with a sodium salt of a sulfonamide. The protecting group can then be removed using chemistry described above and the resulting amine can be incorporated into a final compound using chemistry depicted in Schemes 1 and 8.

SCHEME 30

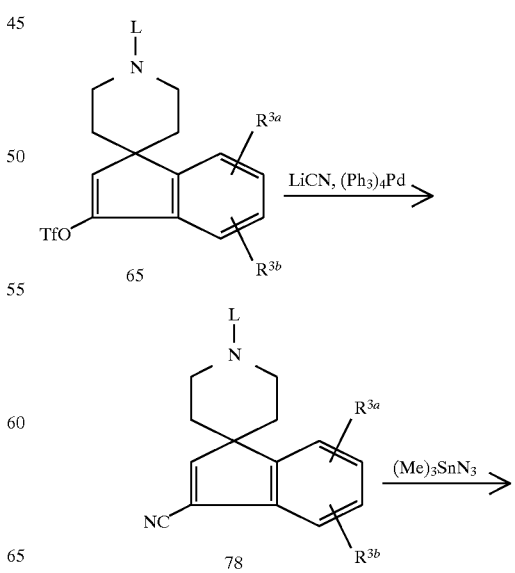

-continued
SCHEME 30

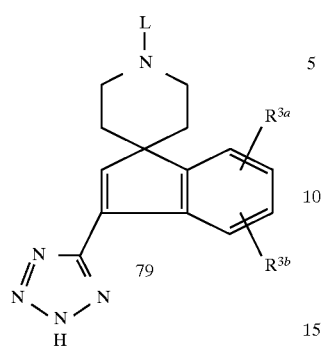

As shown in Scheme 30, tetrazole spiroindane intermediates are available from nitriles of both the shorter and longer homolog series. For example the reaction of enol triflate 65 with a cyanide anion and a palladium catalyst in the presence of an inert solvent such as toluene provides the unsaturated nitrile which can be converted into the tetrazole by reaction with trimethylstannyl azide in an inert solvent at elevated temperatures. Reduction of the indene double bond in 78 and 79 with catalysts such as Pd/C in ethanol affords the corresponding saturated analogs.

SCHEME 31

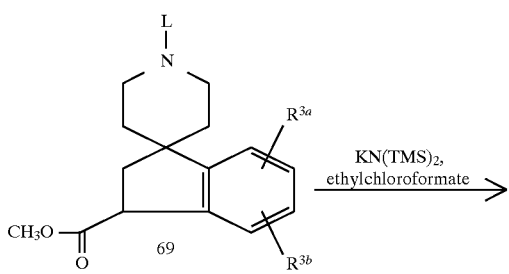

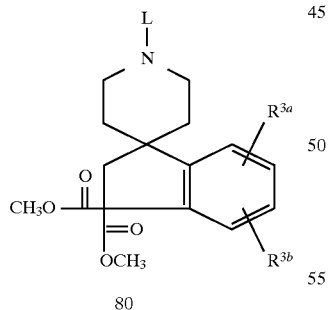

As shown in Scheme 31, esters such as 69 can be conveniently acylated or alkylated next to the ester function by treatment with a variety of bases and alkylating or acylating agents. For example reaction of 69 with potassium bis(trimethyl-silylamide) in an inert solvent such as THF followed by the addition of ethyl chloroformate provides 80 in good yield. Removal of the protecting group and incorporation into the subject compounds can be accomplished as described above.

SCHEME 32

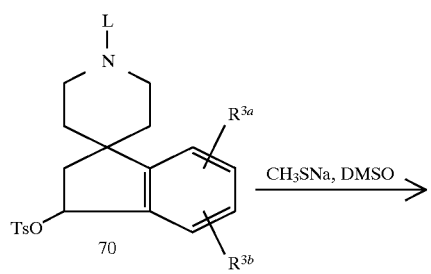

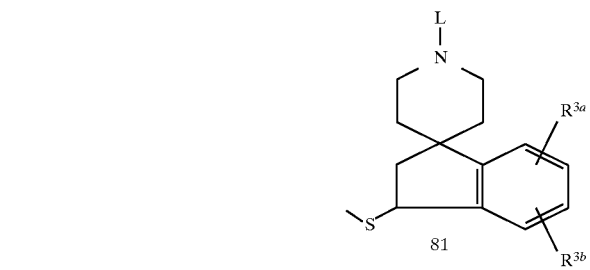

As shown in Scheme 32, further substitution at the benzylic position of the spiroindanes is readily carried out via the tosylate of the alcohol. Displacement of the tosylate with a variety of nucleophiles is possible. For example treatment of tosylate 70 with sodium thiomethoxide in DMSO provides the sulfide 81. The protecting group can be removed as above and the resulting amine can be incorporated into the final compound employing chemistry described in Schemes 1 and 8. Alternatively the sulfide can be oxidized to the sulfoxide or sulfone by treatment with the appropriate oxidizing agent prior to deprotection or as the final step in the synthesis.

SCHEME 33

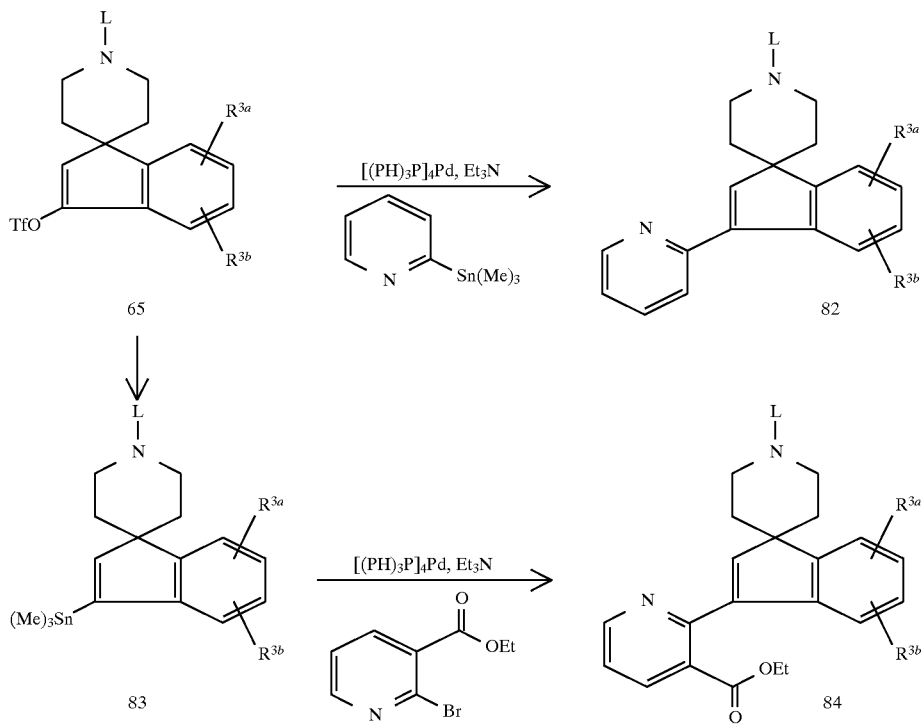

As shown in Scheme 33, the incorporation of aryl and heteroaryl groups into the benzylic position of spiroindanes is most conveniently carried out via the enol triflate 65. Palladium catalysed reaction of the enol triflate with a variety of aryl or heteroarylstannanes in an inert solvent such as toluene provides the desired intermediates. For example 2-trimethylstannyl-pyridine reacts with 65 in the presence of a catalytic amount of tetrakis (triphenylphosphene)palladium in toluene at refux to give the coupled product 82. Alternativiely the enol triflate 65 can be converted into the vinyl stannane 83 by reaction with hexamethylditin and a palladium catalyst in an inert solvent such as toluene. The vinyl stannane can then be coupled with a variety of aryl or hetero aryl bromides or triflates, for example coupling to 2-bromo-3-carbo-methoxypyridine provides 84. The protecting group L can be removed from the coupled products using chemistry described above and the resulting amine can be included in the final compound as described in Schemes 1 and 8.

In some cases the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay disclosed by Smith, et al., Science, 260, 1640–1643 (1993) (see text of FIG. 2 therein). In particular, all of the compounds prepared in the following examples had activity as growth hormone secretagogues in the aforementioned assay. Such a result is indicative of the intrinsic activity of the present compounds as growth hormone secretagogues.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the latter's catabolic side effects or with other pharmaceutically active materials wherein the combination enhances efficacy and minimizes side effects.

Growth promoting and anabolic agents include, but are not limited to, TRH, diethylstilbesterol, amino acids, estrogens, ,β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox. or peptides disclosed in U.S. Pat. No. 4,411,890.

A still further use of the compounds of this invention is in combination with other growth hormone secretagogues such as the growth hormone releasing peptides GHRP-6, GHRP-1 as described in U.S. Pat. Nos. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. In particular, the compounds of this invention may be used in combination with growth hormone releasing factor, an analog of growth hormone releasing factor, IGF-1, or IGF-2. For example, a compound of the present invention may be used in combination with IGF-1 for the treatment or prevention of obesity. In addition, a compound of this invention may be employed in conjunction with retinoic acid to improve the condition of musculature and skin that results from intrinsic aging.

The present invention is further directed to a method for the manufacture of a medicament for stimulating the release of growth hormone in humans and animals comprising combining a compound of the present invention with a pharmaceutical carrier or diluent.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia; treatment of hypercortisonism and Cushing's syndrome; treatment of peripheral neuropathies; replacement of growth hormone in stressed patients; treatment of osteochondrody-splasias, Noonans syndrome, sleep disorders, schizophrenia, depression, Alzheimer's disease, delayed wound healing, and psychosocial deprivation; treatment of pulmonary dysfunction and ventilator dependency; prevention or treatment of congestive heart failure, improving pulmonary function, restoring systolic and diastolic function, increasing myocardial contractility, decreasing peripheral total vascular resistance, diminishing or preventing loss of body weight and enhancing recovery following congestive heart failure; increasing appetite; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and prevention of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. Likewise, the instant compounds are useful in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of: osteoporosis; catabolic illness; immune deficiency, including that in individuals with a depressed $T_4/T_8$ cell ratio; bone fracture, including hip fracture; musculoskeletal impairment in the elderly; growth hormone deficiency in adults or in children; short stature in children; obesity; sleep disorders; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skilled on the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T. Role of Bisphosphonates in Metabolic Bone Diseases. *Trends in Endocrinol. Metab.*, , 4, 19–25 (1993). Bisphosphonates with these utilities include alendronate, tiludronate, dimethyl-APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the growth hormone secretagogues of this invention.

Osteoporosis and other bone disorders may also be treated with compounds of this invention in combination with calcitonin, estrogens, raloxifene and calcium supplements such as calcium citrate or calcium carbonate.

Anabolic effects especially in the treatment of geriatric male patients are obtained with compounds of this invention in combination with anabolic steroids such as oxymetholone, methyltesterone, fluoxymesterone and stanozolol.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg. of body weight daily are administered to patients and animals, e.g., mammals, to obtain effective release of growth hormone. Preferably, the dosage level will be about 0.001 to about 25 mg/kg per day; more preferably about 0.01 to about 10 mg/kg per day.

The following examples are provided for the purpose of further illustration only and are not intended to be limitations on the disclosed invention.

INTERMEDIATE 1

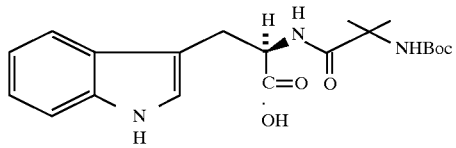

Step A:

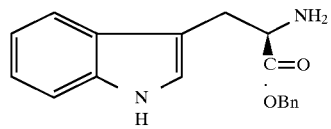

To a solution of the commercially available N-t-BOC-D-tryptophan (25.0 g, 82.2 mmol), benzyl alcohol (10.2 mL, 98.6 mmol), and DMAP (100 mg) in dichloromethane (200 mL) at 0° C., was added EDC (17.4 g, 90.4 mmol) in several portions over a one hour period. The reaction mixture was stirred at room temperature for six hours and was poured into water (200 mL), and the organic layer was separated. The organic solution was washed with a mixture of brine and 3N hydrochloric acid, dried over anhydrous magnesium sulfate, filtered and concentrated to give a thick oil, which solidified upon standing.

To a solution of this oil in 30 mL of dichloromethane was added 20 mL of TFA and stirred for 1 h. The reaction mixture was concentrated, neutralized carefully with saturated aqueous sodium bicarbonate solution, and extracted with dichloromethane (2×100 mL). The combined organic solution was washed with brine (100 mL), passed through a short column of silica gel eluting with 5–10% methanol in dichloromethane to give 23.2 g of the amine as an oil after evaporation.

Step B:

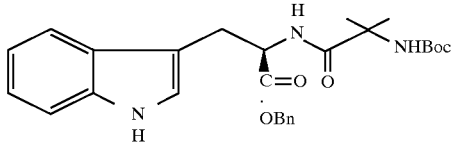

To a solution of the above product, HOBT (10.6 g, 78.8 mmol) and N-BOC-α-methyl alanine (19 g, 94.5 mmol) in 200 mL of dichloromethane, was added EDC (19.5 g, 0.102 mol) in several portions at 0° C. After 5 minutes, the clear reaction mixture became milky. After stirring at room temperature overnight, the reaction mixture was poured into 200 mL of water and the organic layer was separated. The organic solution was washed with brine, and with a brine and saturated sodium bicarbonate solution, dried over anhydrous magnesium sulfate, filtered and concentrated to give a thick oil, which was purified by flash chromatography eluting with 10–40% ethyl acetate in hexane to give the desired material (28.7 g). $^1$H NMR (CDCl$_3$, 200 MHz) δ 8.48 (br.s, 1H), 7.54 (br.d, 1H), 7.38–7.23 (m, 3H), 7.19 (br.d, 2H), 7.15–7.00 (m, 1H), 6.90 (d, 1H), 6.86 (d, 1H), 5.06 (br.s, 2H), 4.95 (ddd, 1H), 3.30 (2dd, 2H), 1.40 (s, 15H)

Step C:

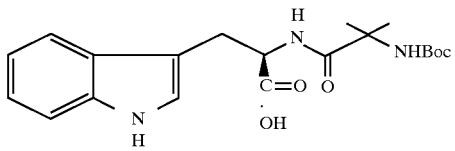

A solution of the material from Step B (28.7 g) in 200 mL of ethanol was stirred at RT under a H$_2$ balloon for 20 minutes in the presence of 10% palladium on carbon (2 g). The catalyst was filtered off through a pad of celite and washed with ethyl acetate. The filtrate was concentrated to give the acid as a slightly pink foam (23.3 g).

$^1$H NMR (CD$_3$OD, 400 MHz) δ 7.56 (d, J=8 Hz, 1 H), 7.31 (dd, J=1, 8 Hz, 1 H), 7.09 (s, 1 H), 7.07 (dt, J=1, 7 Hz, 1 H), 6.98 (dt, J=1, 7 Hz, 1 H), 4.69 (t, J=6 Hz, 1 H), 3.34–3.23 (m, 2 H), 1.35 (s, 3 H), 1.34 (s, 9 H), 1.29 (s, 3 H). FAB-MS calc. for C$_{20}$H$_{27}$N$_3$O$_5$: 389; Found 390 (M+H), 290 (M+H−100 (BOC)).

INTERMEDIATE 2

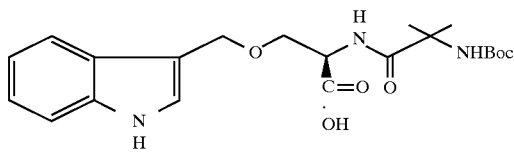

Following the procedures for the preparation of Intermediate 1 using N-t-Boc-O-Benzyl-D-serine in the place of N-t-BOC-D-tryptophan gave Intermediate 2. FAB-MS calc. for C$_{19}$H$_{28}$N$_2$O$_6$: 380; Found 381 (M+H), 325 (M+H−56 (t-Bu)), 281 (M+H−100 (BOC)).

INTERMEDIATE 3

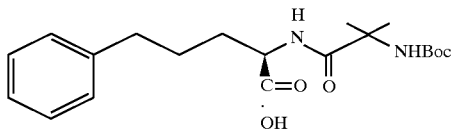

Step A: (DL)-N-Acetyl-2-amino-5-phenylpentanoic acid

To a solution of sodium (2.3 g, 0.1 mol) in ethanol (60 mL) under nitrogen at room temperature, was added diethyl acetamidomalonate. The mixture was stirred at room temperature for one hour, and then 1-bromo-3-phenylpropane was added dropwisely. After the addition, the mixture was stirred at room temperature for two hours, then refluxed overnight. It was cooled to room temperature and partitioned between water and ethyl acetate. The organic layer was washed with sodium bicarbonate in water, dried over MgSO4 and evaporated to give an intermediate (32.5 g, 97%). $^1$H NMR (CDCl3, 400 MHz) 7.26–7.10 (m, 5 H); 6.75 (br. s, 1 H); 4.19 (q, J=7 Hz, 4 H); 2.58 (t, J=7.9 Hz, 2 H); 2.39–2.35 (m, 2 H); 2.00 (s, 3 H); 1.43–1.39 (m, 2 H); 1.20 (t, J=7 Hz, 6 H).

The product above was suspended in 190 mL of 2.5N NaOH in water and refluxed for two hours. The mixture was cooled to 0° C., and it was carefully neutralized with 6N HCl to pH2. The precipitate was collected using a glass sinter funnel and washed with a small amount of cold water and air dried. The solid was then suspended in 300 mL of water and refluxed for four hours. The solution was cooled and acidified to pH1 and the solid was collected by filtration (15.3 g, 67%). $^1$H NMR (CD3OD, 400 MHz) 7.26–7.12 (m, 5 H); 4.90–4.37 (m, 1 H); 2.65–2.60 (m, 2 H); 1.97 (s, 3 H); 1.87–1.82 (m, 1 H); 1.73–1.65 (m, 3 H).

Step B: (D)-N-Acetyl-2-amino-5-phenylpentanoic acid

The racemic intermediate from the previous step (10 g, 42.5 mmol) and CoCl3-6H$_2$O were dissolved in 21 ml of 2N KOH and 200 mL of water at 40° C., and the pH of the solution was adjusted to 8 by the addition of the several drops of 2N KOH. Then acylase I (Aspergillus sp, 0.5 u/mg, from Sigma; 0.9 g) was added with vigorous stirring. The reaction mixture was stirred for one day at 40° C. and the pH was kept at 8 by the addition of a few drops of KOH. The solid which formed was filtered off. The filtrate was acidified by 3N HCl to pH2, and was extracted with ethyl acetate (200 mL×4). The organic extracts were combined and evaporated to give a white solid (4.64 g, 46%) $^1$H NMR (CD3OD, 400 MHz) 7.26–7.12 (m, 5 H); 4.90–4.37 (m, 1 H); 2.65–2.60 (m, 2 H); 1.97 (s, 3 H); 1.87–1.82 (m, 1 H); 1.73–1.65 (m, 3 H).

Step C: (D)-N-t-Boc-2-amino-5-phenylpentanoic acid

The intermediate from step B (4.2 g, 17.8 mmol) was suspended in 2N HCl (100 mL) and refluxed for two hours. The reaction mixture was evaporated in vacuo to remove water and hydrochloric acid to yield a white solid. To a solution of this solid in 50 mL of water, was added 3N NaOH until the pH 11, then di-t-butyl dicarbonate (4.66 g, 21.4 mmol) was added with vigorous stirring. After four hours, the reaction mixture was acidified to pH2 with 3N HCl and it was extracted with ethyl acetate (100 mL×3). The organic extracts were combined and evaporated to give a white solid (6.56 g, crude) which was used without purification. $^1$H NMR (CD3OD, 400 MHz) 7.26–7.12 (m, 5 H); 4.11–4.08 (m, 1 H); 2.65–2.60 (m, 2 H); 1.83–1.62 (m, 4 H); 1.43 (s, 9 H).

Step D:

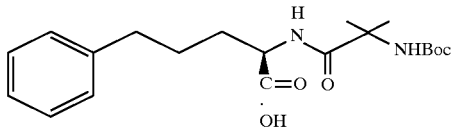

Following the procedures for the preparation of Intermediate 1 using (D)-N-t-Boc-2-amino-5-phenylpentanoic acid in the place of N-t-BOC-D-tryptophan gave Intermediate 3. ¹H NMR (CDCl₃, 400 MHz) 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

INTERMEDIATE 4

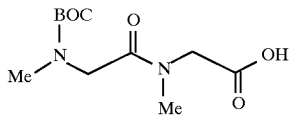

Step A:

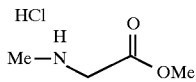

A solution of N-Boc Sarcosine (1.66 g) in methanol was cooled to 0° C. and thionyl chloride (0.67 ml) was added slowly. After stirring for 12 hours at room temperature the mixture was concentrated to give the desired product.

Step B:

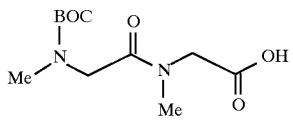

To a solution of the above intermediate in chloroform was added N-Boc Sarcosine (2.0 g), EDC (3.35 g), HOBt (1.42 g) and triethylamine (3.7 ml) and stirred for 12 hours at room temperature. The mixture was poured into 1N HCl and extracted with methylene chloride, dried over sodium sulfate, filtered and concentrated to give 3 g of coupled product. To this material in methanol was added 6N NaOH at room temperature and stirred for 5 hours. The mixture was concentrated to remove the methanol and the residue was extracted with methylene chloride. The organic layer was discarded. The aqueous layer was cooled to 0° C. and acidified with conc. HCl to pH=1.0 and extracted with ethyl acetate. The organic layer was dried over sodium sulfate and concentrated to give desired product (2.0 g).

EXAMPLE 1

N-acetyl-Threo-(2R,3S)-β-methyl tryptophan R-(+)-α-methylbenzyl amine salt

Racemic β-methyltryptophan was prepared by the method of Snyder and Matteson (*J. Am. Chem. Soc.* 1957, 79, 2217). Isomer A (100 g) was suspended in 1.25 L of 90/10 acetone water at 20° C. and 50 mL of R-(+)-α-methylbenzylamine was added in one portion. The suspension cleared briefly before a thick white suspension formed which quickly turned to a solid mass. After aging overnight, an additional 500 mL of acetone was added to facilitate agitation and filtration. The suspension was filtered and the cake washed with 500 mL of acetone and sucked to a damp cake. The solid was suspended in 2.5 L of 90/10 acetone/water and heated to boiling on a steam bath. The white slurry was allowed to cool to 20° C. overnight. The product was collected by filtration, washed with acetone and dried yielding 39.1 g of the title compound. α=+9.1° (c=1, MeOH). Stereochemical assignments were made by comparison to published compounds: *J. Org. Chem.* 1994, 59, 4239 and *J. Org. Chem.* 1995, 60, 4978.

EXAMPLE 2

N-acetyl-Threo-(2S,3R)-β-methyltryptophan S-(−)-α-methylbenzyl amine salt

The mother liquors from Example 1 were combined and concentrated to ca. 1 L and 400 mL of 1N HCl was added. The resulting suspension was stirred for 1 hr initially at 20° C. then at 0° C. The product was filtered and washed with water until the filtrate was neutral. The product was sucked to a damp cake weighing 79 g. The solid was suspended in 1 L of 95% acetone/water and 40 mL of S-(−)-α-methylbenzylamine was added followed by 1 L of 90% acetone/water. After a few minutes a solid mass formed. An additional 500 mL of acetone was added and the mixture heated on a steam bath for ca. 0.5 hr. This was then allowed to stand at 20° C. overnight. The product was collected by filtration, washed with 500 mL of acetone, and sucked to a damp cake. The product was suspended in 2 L of 95% acetone/water and heated on a steam bath to boiling. The white suspension was allowed to cool to 20° C. overnight. The product was collected by filtration, washed with 500 mL of acetone and dried yielding 54 g. α=−9.0° (c=1, MeOH).

EXAMPLE 3

N-acetyl-Erythro (2R,3R)-β-methyltryptophan R-(+)-α-methylbenzyl amine salt 170 g of Isomer B (prepared as described by the reference in Example 1) which was a brittle foam containing ethyl acetate was dissolved in 2.5 L of ethyl acetate containing 100 mL of ethanol. To this was added 60 mL of R-(+)-α-methylbenzylamine. After 10 min, an additional 2 L of ethyl acetate was added and the resulting thick suspension was aged at 20° C. for 3 days. The product was collected by filtration, washed with ethyl acetate and and sucked to a damp cake. The salt was re-slurried four times with hot ethyl acetate containing 2% water (1×2.5 L, 2×6 L, and 1×8 L). The yield of dried product was 43.2 g of salt. α=−19.6° (c=1, MeOH).

EXAMPLE 4

N-acetyl-Erythro (2S ,3S)-β-methyltryptophan S-(−)-α-methylbenzyl amine salt

The mother liquors from Example 3 were combined and concentrated to ca. 2 L and washed twice with 500 mL 1N HCl. The washes were back extracted once with ethyl acatate, and the combined ethyl acetate extracts washed twice with brine. The solution was diluted to 6 L with ethyl acatate and 60 mrL of S-(−)-α-methylbenzylarnine was added. After 10 min the resulting suspension was heated to boiling. The suspension was allowed to cool to ambient temperature with stirring overnight. The product was collected by filtration washed with ethyl acetate and and sucked to a damp cake. The salt was suspended in 6 L of ethyl acetate and suspension was heated to boiling. The suspension was allowed to cool to ambient temperature with stirring overnight. The product was collected by filtration washed with ethyl acetate and dried. The yield of dried product was 65.8 g of salt. α=+19.7° (c=1, MeOH).

EXAMPLE 5

N-acetyl-threo-(2S,3R)-β-methyltryptophan

The salt from Example 2 (53 g) was stirred with 400 mL 1N HCl at 20° C. for 20 min. The suspension was filtered and the cake washed with water until the filtrate was neutral. The wet cake was used directly for the next reaction. A sample was dried affording the title compound. α=−26.4° (c=1,MeOH).

EXAMPLE 6 threo-(2S,3R)-β-methyltryptophan

The wet cake from Example 5 was suspended in with 400 mL of 1N HCl and refluxed for 12 hours. The solution was cooled to 20° C., and half of the solution was used for example 7. The title compound was isolated by adjusting the pH to 7.0 with sodium hydroxide, cooling the resulting suspension to 0° C., filtering, washing the cake with water and drying. α=−29.3° (c=0.9, H$_2$O).

EXAMPLE 7

N-t-BOC-threo-(2S,3R)-β-methyltryptophan

The pH of the aqueous solution from Example 6 was adjusted to 7 with sodium hydroxide and cooled to 0° C. 20 g of potassium carbonate, 19 g of di-t-butyl dicarbonate, and 150 mL of THF were added. The mixture was allowed to warm slowly to ambient temperature overnight. The reaction was extracted twice with ether, the aqueous acidified with 2N HCl and extracted twice with ethyl acetate. The combined ethyl acetate extracts were washed with brine, dried with MgSO$_4$, filtered and concentrated affording 21.2 g of the title compound.

EXAMPLE 8

N-acetyl-threo-(2R,3S)-β-methyltryptophan

The title compound was prepared essentially following the procedure of Example 5. α=+26.6° (c=1,MeOH).

EXAMPLE 9 threo-(2R,3S)-β-methyltryptophan

The title compound was prepared essentially following the procedure of Example 6. α=+30.6° (c=0.9, H$_2$O).

EXAMPLE 10

N-t-BOC-threo-(2R,3R)-β-methyltryptophan

The title compound was prepared essentially following the procedure of Example 7.

EXAMPLE 11

N-acetyl-Erythro (2S,3S)-β-methyltryptophan

The salt from Example 4 (65 g) was stirred with 250 mL 1N HCl and 1.5 L of ethyl acetate at ambient temperature for 5 min. The layers were partitioned and the ethyl acetate layer was washed with 1N HCl, H$_2$O and brine, dried with MgSO$_4$, filtered and concentrated to afford the title compound as a brittle foam.

EXAMPLE 12

Erythro (2S,3S)-β-methyltryptophan

The product from Example 11 was suspended in with 500 mL of 2N HCl and refluxed for 4 hours. The solution was cooled to 20° C., and half of the solution was used for Example 13. The title compound isolated as a foam by concentrating the solution in vacuo.

EXAMPLE 13

N-t-BOC-Erythro (2S,3S)-β-methyltryptophan

The pH of the aqueous solution from Example 6 was adjusted to 7 with sodium hydroxide and cooled to 0° C. 24 g of potassium carbonate, 22 g of di-t-butyl dicarbonate, and 150 mL of THF were added. The mixture was allowed to warm slowly to ambient temperature overnight. The reaction was extracted twice with ether The aqueous acidified with 2N HCl.and extracted twice with ethyl acetate. The combined ethyl acetate extracts were washed with brine, dried with MgSO$_4$ filtered and concentrated. The solid was redissolved in ether, and the ether removed in vacuo while flushing with hexanes. The resulting slurry was filtered and dried affording 20.1 g of the title compound.

EXAMPLE 14

N-acetyl-threo-(2R,3R)-β-methyltryptophan

The title compound was prepared essentially following the procedure of Example 11. α=° (c=1,MeOH).

EXAMPLE 15 threo-(2R,3R)-β-methyltryptophan

The title compound was prepared essentially following the procedure of Example 12. α=° (c=0.9, H$_2$O).

EXAMPLE 16

N-t-BOC-threo-(2R,3R)-β-methyltryptophan

The title compound was prepared essentially following the procedure of Example 13.

EXAMPLE 17

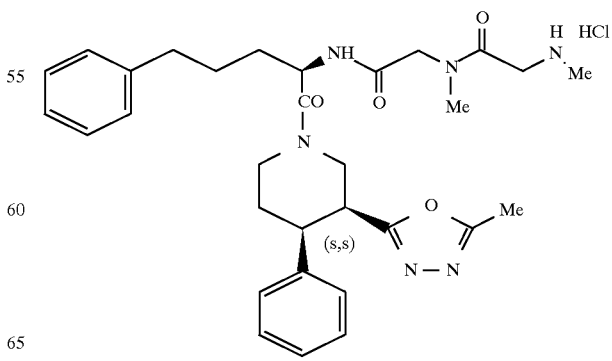

Step A:

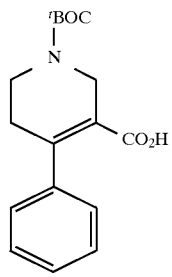

To a solution of 3-ethoxycarbonyl-4-piperidone hydrochloride (25 g, 120 mmole) and 3-methoxycarbonyl-4-piperidone hydrochloride (25.3 g, 130 mmole) in 70 ml of 6N aqueous sodium hydroxide was added di-t-butyl-dicarbonate (55 g, 255 mmole) in 200 ml of dioxane at 0° C. After ½ hour at 0° C. and 3 hours at room temperature the mixture was diluted with ethyl acetate and washed with 0.5N hydrochloric acid and brine. The organic layer was dried over magnesium sulfate, filtered and concentrated. To the crude residue in 800 ml of methylene chloride was added diisopropylethylamine (65 ml, 375 mmole) and triflic anhydride (46 ml, 275 mmole) at −78° C. After ½ hour the mixture was poured into saturated sodium bicarbonate solution and extracted with methylene chloride. The organic layer was washed with 1N hydrochloride, brine and dried over magnesium sulfate. The organic layer was concentrated to give the vinyl triflate. To a solution of the vinyl triflate in 700 ml of THF was added $K_2CO_3$ (51.7, 375 mmole), phenylboronic acid (25 g, 205 mmole) and $Pd(PPh_3)_4$ (3.7 g, 3.2 mmole) at room temperature. The reaction mixture was refluxed for 16 hours and then poured into water and extracted with ether (3×). The organic layers were washed with water (3×), brine and dried over magnesium sulfate. The solution was then concentrated to dryness. The residue was dissolved in 100 ml of ethanol and 6N NaOH (100 ml) was added and refluxed for 3 hours. The mixture was concentrated to dryness, the residue was dissolved in water and extracted with methylene chloride. The organic layer was discarded. The aqueous layer was cooled in an ice bath and was acidified with 6N HCl to pH=2.0. The aqueous layer was extracted with ether (3×), brine, dried over sodium sulfate and concentrated to give the desired acid (68.3 g).

Step B:

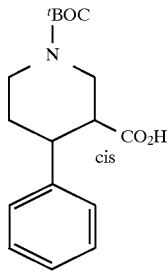

The intermediate from Step A (68.3 g, 225 mmole) was dissolved in 300 ml of methanol and hydrogenated over $Pd(OH)_2$ (3.7 g) at 40 psi for 6 hours and then at one atmosphere for 16 hours. The mixture was filtered through Celite to remove Pd catalyst and the filtrate was concentrated under vacuum to give the cis acid (68.9 g).

Step C:

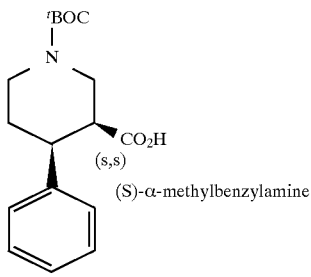

The intermediate obtained in Step B (68.9 g) and (S)-α-methylbenzylamine (28.9 ml, 225 mmole) were dissolved in methanol with heating. The solution was left in refrigerator for 16 hours and the crystals that were formed were filtered off (25 g). Recrystallization from 1500 ml of ethyl acetate/methanol (5/1) gave the desired amine salt (19 g). The stereochemistry of this compound was determined by X-ray crystallographic analysis.

Step D:

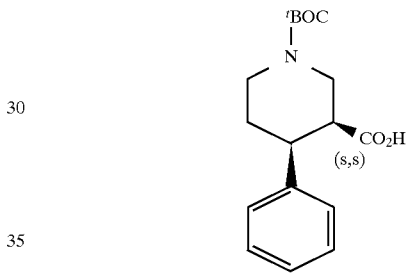

The intermediate from Step C (19 g) was suspended in 1N HCl and was extracted with ether. The organic extracts were combined, dried over sodium sulfate, and evaporated to give the title compound as a white solid. (13.6 g).

Step E:

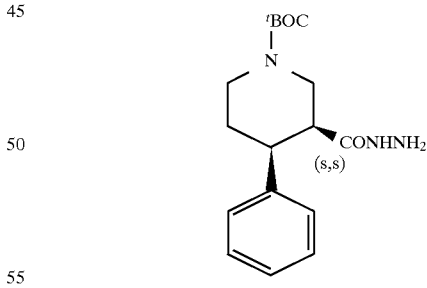

To a solution of the intermediate from Step D (10 g) in THF (200 ml) was added carbonyldiimidazole (5.8 g) at room temperature. After 1 hour this mixture was slowly added to a solution of hydrazine in ethanol (200 ml) at 0° C. over a 30 minutes period. The resulting mixture was warmed to room temperature and stirred an additional hour. The mixture was concentrated and the residue was taken up in water and extracted with methylene chloride, brine, dried over sodium sulfate and concentrated to give desired product (10.2 g).

Step F:

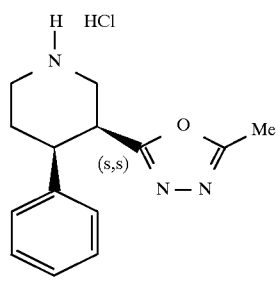

A solution of the intermediate from Step E (5.0 g) and triethyl orthoacetate (10 ml) were heated to 100° C. for 4 hours. The mixture was poured into 0.5N HCl and extracted with methylene chloride. The organic layer were washed with water, brine and dried over sodium sulfate. Concentration in vacuum and purification by MPLC (hexanes/ethyl acetate=2/1) gave the desired product which was dissolved in ethyl acetate and bubbled HCl gas at 0° C. until it was saturated. The mixture was stirred at room temperature for 30 minutes and evaporated to give the desired product (4.0 g).

Step G:

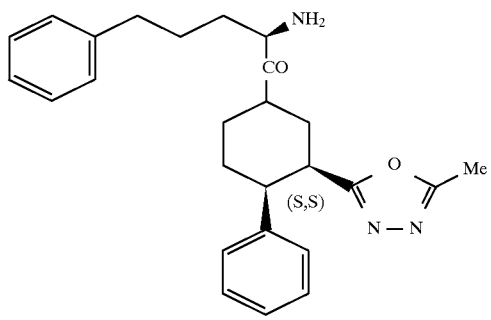

To a solution of the intermediate prepared in Step F (396 mg) in chloroform was added (D)-N-t-Boc-2-amino-5-phenyl pentanoic acid (492 mg), EDC (541 mg), HOBt (226 mg) and triethylamine (0.58 ml) and stirred at room temperature for 12 h. The mixture was poured into 1N HCl and extracted with methylene chloride, dried over sodium sulfate, filtered and concentrated. The residue was purified by RPLC (chromatotron) (hexanes/ethyl acetate=1/1) to give the coupled product (490 mg). To this coupled product in methylene chloride was added TFA and the mixture was stirred at room temperature for 1 hour. The reaction mixture was concentrated and the residue was taken up in water, basified with 1N NaOH and extracted with chloroform. The organic layer was washed with brine, dried over sodium sulfate, filtered and concentrated to give the desired product (350 mg).

Step H:

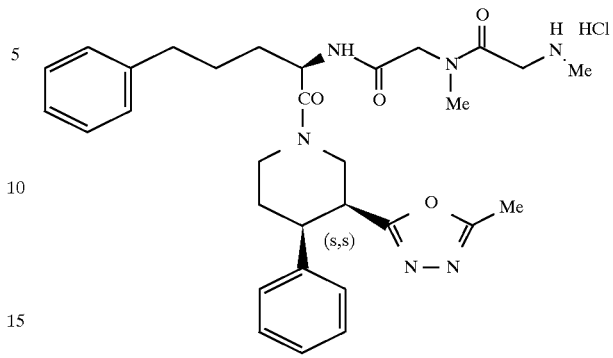

To a solution of the compound from Step G (100 mg) in chloroform was added Intermediate 4 (34 mg), EDC (53 mg) and HOBt (22 mg) and stirred at room temperature for 12 h. The mixture was poured into 1N HCl and extracted with methylene chloride. The combined organics was dried over sodium sulfate, filtered and concentrated and the residue was purified by PLC (methylene chloride/methanol 20/1) to give the coupled product. To a solution of this material in ethyl acetate at 0° C. was bubbled in HCl gas until it was saturated. The mixture was stirred at room temperature for 10 minutes and was evaporated to give a desired product (39 mg).

$^1$H NMR (400 MHz, CD3OD, mixture of rotamers): 7.31–7.04 (m, 10 H), 4.85–4.62 (m, 2H), 4.13–3.98 (m, 5 H), 3.65 (m, 1 H), 3.37 (m, 1 H), 3.18 (m, 1 H), 3.01 (s, 3/2 H), 2.97 (s, 3/2 H), 2.74 (s, 3 H), 2.92–2.35 (m, 3 H), 2.29 (s, 3 H), 2.00–1.54 (m, 6 H). FAB-MS: 561.3 (M+1).

The following compounds were prepared according to the methods described in Steps G and H for the synthesis of Example 17 by using proper amino acids.

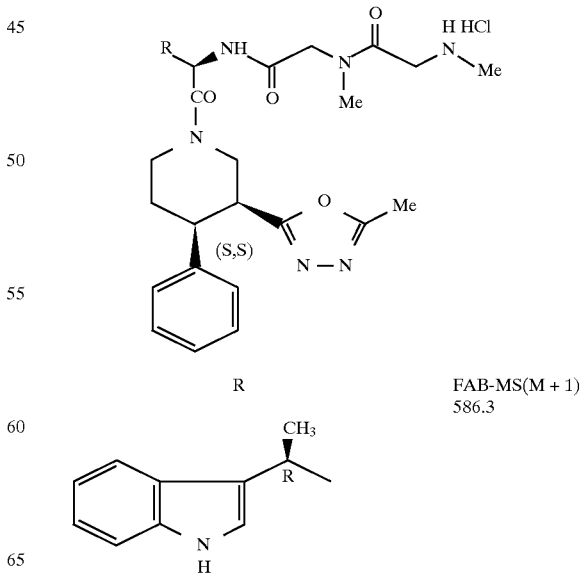

R     FAB-MS(M + 1)
             586.3

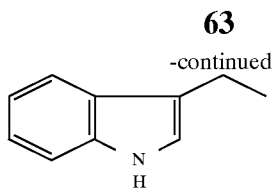
572.2

EXAMPLE 18

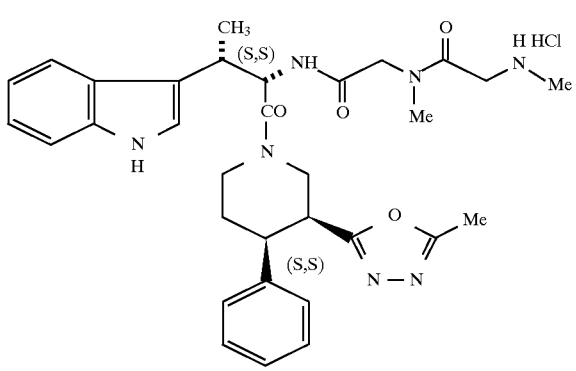

Prepared as described in Example 17 but by using N-Boc-(2S,3S)-2-methyl-Trp instead of (D)-N-t-Boc-2-amino-5-phenyl pentanoic acid). FAB-MS: 586.3 (M+1).

EXAMPLE 19

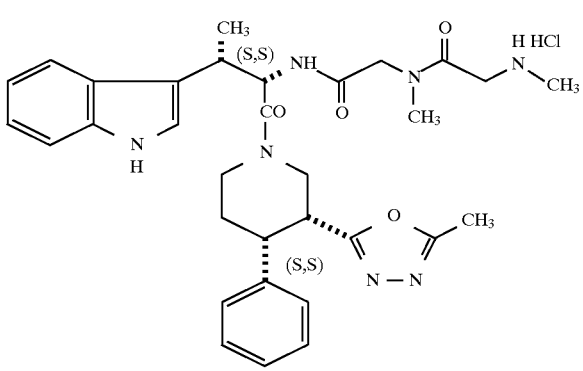

Step A:

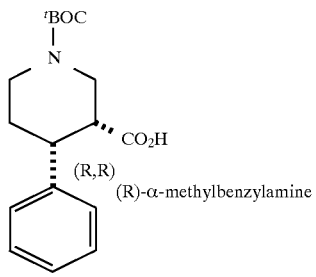
(R)-α-methylbenzylamine

The mother liquid from Step C of Example 17 was concentrated to give an off-white solid (68 g). This material was dissolved in 1N NaOH and extracted with methylene chloride. The organic layer was discarded. The aqueous layer was acidified with conc. HCl at 0° C. to pH=1.0 and the precipitate that had formed was collected after stirring at 0° C. for 10 minutes. The white solid was dried under nitrogen to give 28 g of acid. The acid was dissolved in hot methanol and (R)-α-methylbenzylamine (11.12 g) was added. The solution was left in refrigerator for 16 hours and the crystals that had formed were filtered off (15 g).

Step B:

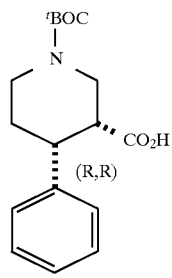

The intermediate from Step A (4.3 g) was suspended in 1N HCl and was extracted with ether. The extracts were combined, dried over sodium sulfate and evaporated to give a white solid. (3.0 g).

Step C:

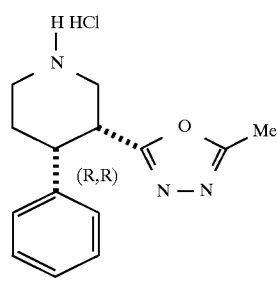

Prepared from the intermediate (750 mg) from Step B by using the procedure described in Steps E and F of Example 17.

Step D:

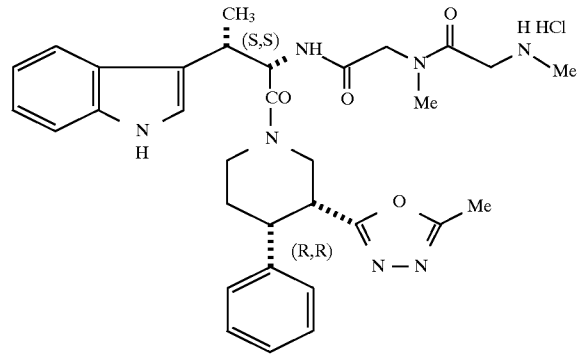

Prepared from the intermediate synthesized in Step C by using the procedures described in Steps G and H of Example 17 (N-Boc-β-(S)-methyl-(L)-Trp was used instead of (D)-N-t-Boc-2-amino-5-phenyl pentanoic acid). FAB-MS: 586.3 (M+1).

EXAMPLE 20

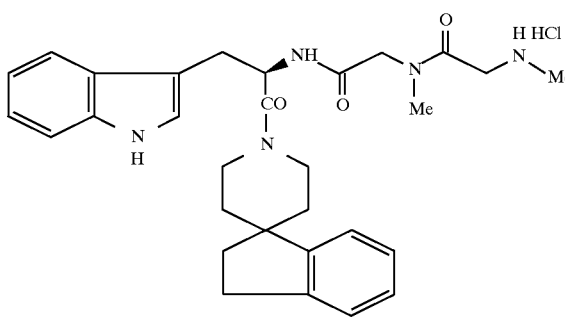

Prepared from spiro-indanyl piperidine (see *J. Med. Chem.* 1992, 35, 2033 for preparation) and N-Boc-(D)-Trp as detailed in Steps G and H of Example 17. FAB-MS: 516.2 (M+1).

EXAMPLE 21

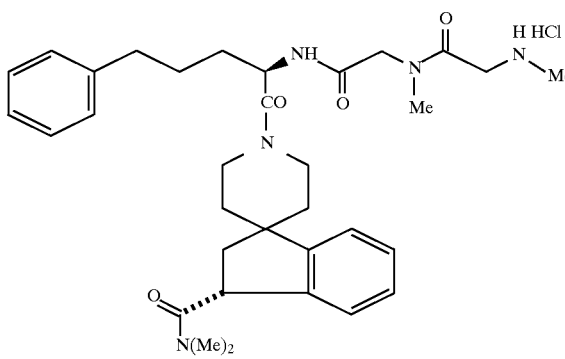

Step A:

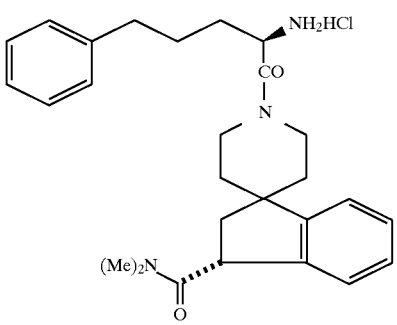

The intermediate from Example 38 Step G was deprotected with ethyl acetate/HCl and the resulting product (200 mg, 0.68 mmol) was coupled to (2R)-N-t-Boc-5-phenyl pentanoic acid (240 mg, 0.81 mmol) using EDC (190 mg, 1 mmol), HOBT (130 mg, 1.0 mmol) and NMM (0.097 ml, 0.88 mmol). The BOC protected title compound (130 mg) was obtained after purification (Prep TLC dichlormethane/ acetone 9:1). The title compound was obtained after treatment with ethyl acetate HCl.

Step B:

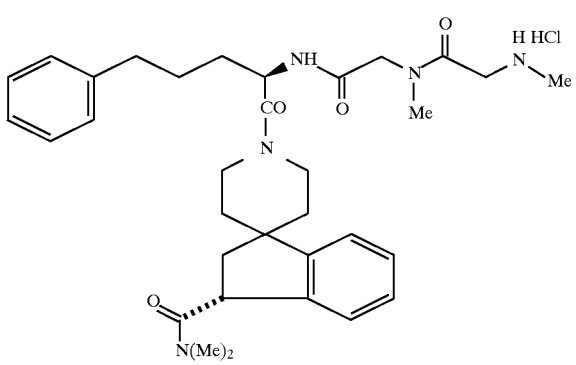

Prepared from the intermediate obtained from Step A by the procedure described in Example 17, Step G and Step H to give the desired compound. $^1$H NMR (400 MHz, CD3OD, mixture of rotamers):

7.30–7.05 (m, 9H), 4.92 (m, 1 H), 4.58 (m, 1H), 4.49 (m, 1 H), 4.27–3.84 (m, 6 H), 3.33 (m, 1/2 H), 3.20 (m, 1/2 H), 3.04 (s, 3 H), 3.02 (s, 3 H), 2.99 (s, 3/3 H), 2.96 (s, 3/3 H), 2,.94 (s, 3/3 H), 2.74 (s, 3 H), 3.00–2.50 (m, 3 H), 2.16 (m, 1 1/2 H), 1.90–1.42 (m, 7 1/2 H). FAB-MS: 576.4 (M+1).

EXAMPLE 22

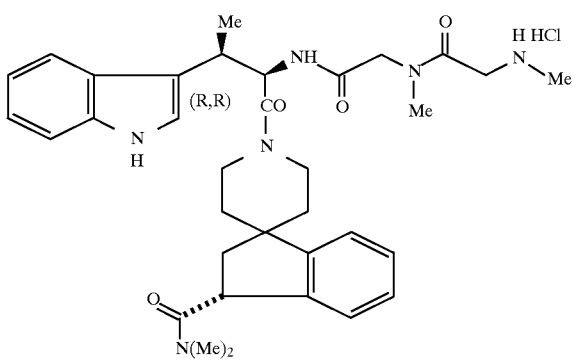

Step A:

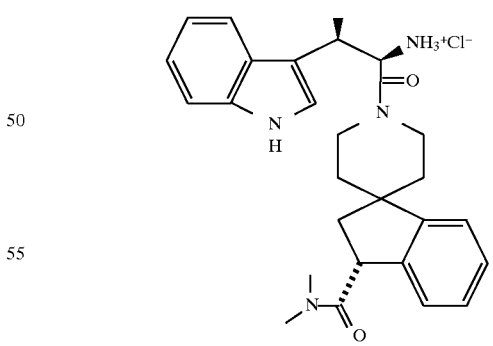

A sample of the title compound from Example 38 Step G was deprotected with a saturated solution of HCl in ethyl acetate to give the hydrochloride salt (6.3 g, 21 mmol). To this salt in dichloromethane at 0° C. was added (R,R)-b-methyltryptophan (7.0 g, 22 mmol), HOBT (4.4 g, 33 mmol), NMM (4.83 ml,44 mmol) and finally EDC(6.3 g, 33 mmol). The reaction mixture was warmed to room temperature and stirred overnight. It was then poured into ethyl acetate and washed with 1N HCl, saturated bicarb, and brine then dried over magnesium sulfate. The organic layer was filtered and concentrated. Purification by flash chromatography (ethyl acetate) provided the title compound (10 g, 17.9 mmol). A solution of this intermediate (1.32 g, 2.6 mmol)) in ethyl acetate (8 mL) was cooled to 0° C. While stirring, HCl-EtOAc was added to the mixture (10 mL). The reaction was stirred for 20 minutes, until TLC analysis indicated that the reaction was complete. The solution was then concentrated to remove the ethyl acetate to afford 1.25 g of the product (100%). ESI-MS calc. for C28H33N4O2: 457; Found 458 (M+H).

Step B:

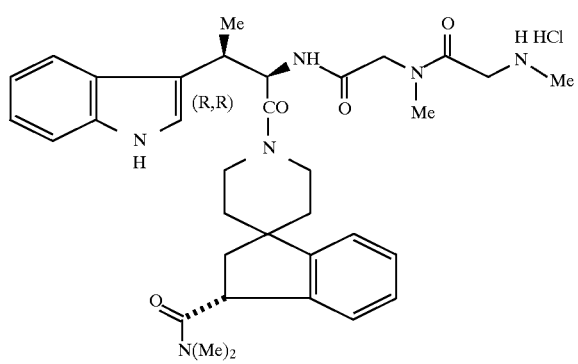

Prepared from the intermediate obtained from Step A by the procedure described in Example 17, Step G (using N-Boc-b-(R)-methyl-(D)-Trp instead of (D)-N-t-Boc-2-amino-5-phenyl pentanoic acid) and Step H to give the desired compound. FA-B-MS: 601.5 (M+1).

EXAMPLE 23

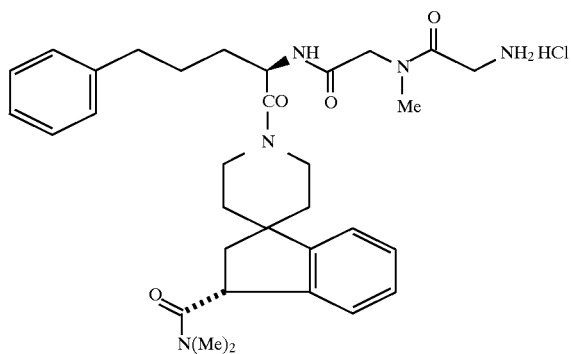

Step A:

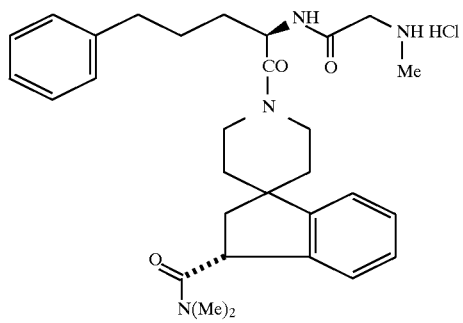

Prepared from the intermediate obtained from Example 21, Step A by standard peptide-type coupling but N-Boc-Sarcosine was used instead of Intermediate 4.

Step B:

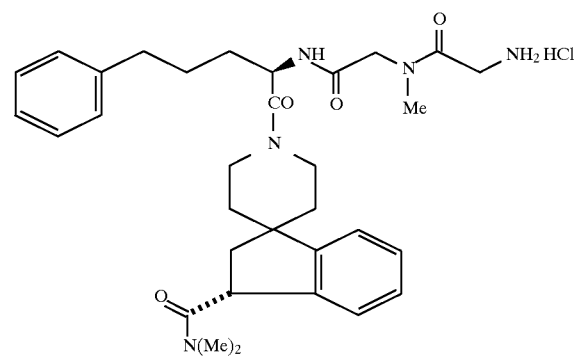

To a solution of the intermediate prepared from Step A (11 mg) in chloroform was added N-Boc-Gly (4.3 mg), EDC (8 mg), HOBt (3.3 mg) and triethylamine (0.008 ml) and stirred for 12 hours. The reaction mixture was poured into 1N HC, extracted with methylene chloride, dried over sodium sulfate, filtered and concentrated. The residue was purified by PLC (methylene chloride/methanol=10/1) to give the coupled product. This coupled product was deprotected by the HCl/ethyl acetate protocol to give a desired product (11 mg).

$^1$H NMR (400 MHz, CD3OD, mixture of rotamers): 7.27–7.04 (m, 9 H), 4.92 (m, 1 H), 4.56 (m, 1H), 4.49 (m, 1H), 4.24–3.87 (m, 6H), 3.33 (m, 1/2 H), 3.20 (m, 1/2 H), 3.04 (s, 3 H), 3.02 (s, 3 H), 2.99 (s, 3/2 H), 2.97 (s, 3/2 H), 3.00–2.50 (m, 3 H), 2.16 (m, 1 1/2 H), 1.90–1.42 (m, 7 1/2 H). FAB-MS: 562.4 (M+1).

Additional compounds were prepared as described in Example 23 Step B using the appropriate amino acids.

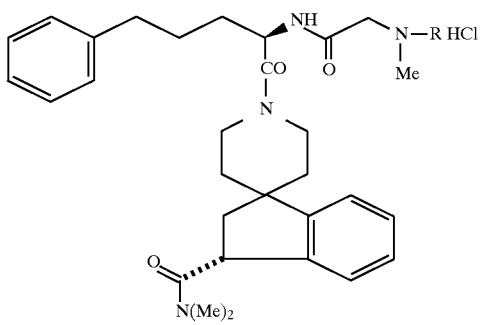

| R | FAB-MS: |
|---|---|
| D-Ala | 576.4 |
| L-Ala | 576.4 |

EXAMPLE 24

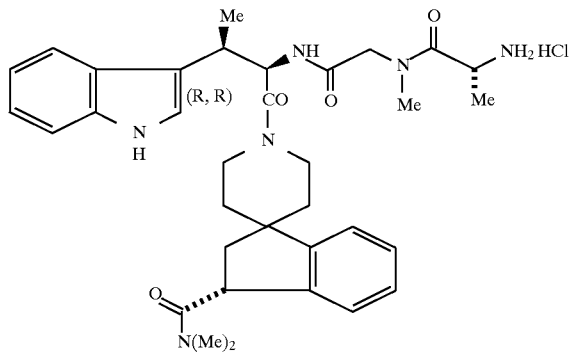

Prepared from the intermediate obtained from Example 22, Step A by using peptide-type coupling methods as described above. FAB-MS: 601.6 (M+1).

EXAMPLE 25

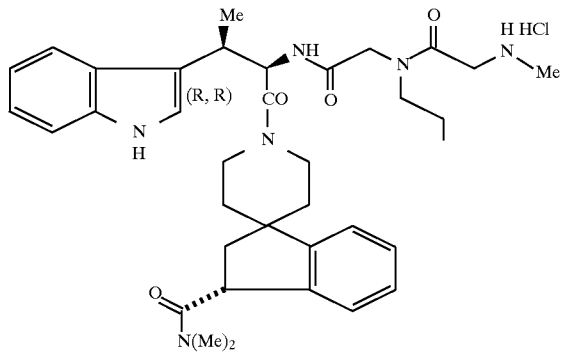

Step A:

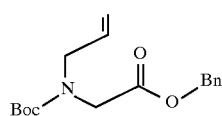

To a solution of N-Boc-Gly (3.0 g) in methylene chloride (100 ml) was added benzyl alcohol (1.6 ml), EDC (4.4 g) and a catalytic amount of DMAP. After 2 hours, the mixture was poured into 1N HCl and extracted with methylene chloride, dried over sodium sulfate, filtered and concentrated to give N-Boc-Gly-OBn (4.5 g). To a solution of N-Boc-Gly-OBn (1.32 g) in THF (10 ml) was added potassium bis(trimethylsilyl)amide (1.19 g) in THF (20 ml) at −78° C. After 30 minutes at −78° C. allyl bromide (0.52 ml) was added to the reaction mixture slowly. The resulting mixture was slowly warmed up to room temperature and stirred for an additional 12 hours. The mixture was poured into 1N HCl and extracted with ether, the combined organics were dried over sodium sulfate, filtered and concentrated. The residue was purified by chromatotron (hexanes/ethyl acetate=10/1) to give desired product (585 mg).

Step B:

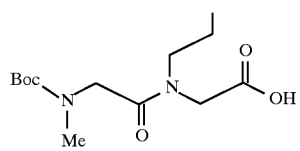

The intermediate obtained from Step A (585 mg) was treated TFA with at room temperature for 10 minutes. The mixture was concentrated and azeotroped with toluene (3×) to give a white solid. To this white solid in chloroform was added EDC (729 mg), N-Boc-Sar (435 mg), triethylamine (0.78 ml) and a catalytic amount of DMAP. After 12 hours the mixture was poured into 1N HCl and extracted with methylene chloride, the combined organics were dried over sodium sulfate, filtered and concentrated The residue was purified by PLC (hexanes/ethyl acetate=5/1) to give the coupled product (115 mg). This material (115 mg) in methanol was hydrogenated over Pd(OH)$_2$ at 1 ATM for an hour. The mixture was filtered through Celite to remove Pd catalyst and the filtrate was concentrated under vacuum to give the desired product (88 mg).

Step C:

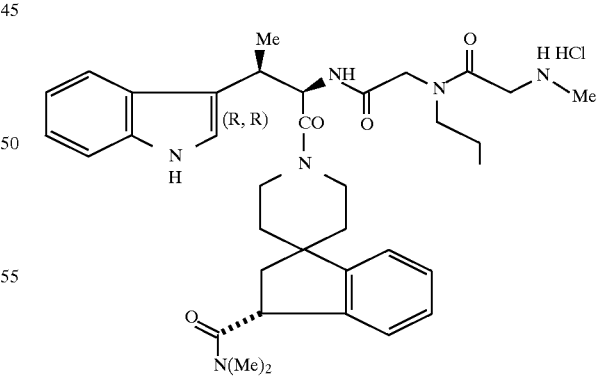

Prepared from the intermediate obtained from Example 22, Step A and the compound synthesized in Step B by standard coupling and deprotection chemistry. FAB-MS: 629.3 (M+1).

EXAMPLE 26

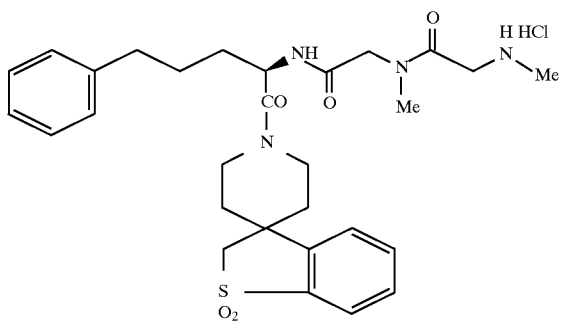

Step A:

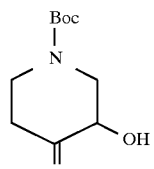

To a suspension solution of methyltriphenyl-phosphonium iodide (30 g, 74 mmole) in 150 mL of THF was slowly added butyllithium (2.5N, 25.5 mL, 63.7 mmole) at 0° C. After an hour at room temperature, N-t-BOC protected 4-piperidone (prepared from 4-piperidone monohydrate hydrochloride by the procedure described in Protective Groups in Organic Synthesis T. W. Greene, John Wiley and Sons, NY. 1981.) in 50 mL of THF was added to reaction mixture at room temperature slowly. This reaction was stirred for 2 hours and filtered. The filtrate was concentrated and purified (MPLC, silica gel, hexanes/ethyl acetate=10/1) to give the Wittig product (7.9 g) in 82% yield. To a suspension of selenium dioxide/silica gel (prepared according to the procedure described in Chem. Lett. 1981, 1703) in 30 mL methylene chloride was added t-butyl hydroperoxide (1.23 mL). After 15 minutes, the Wittig product (0.72 g, 3.69 mmole) in 5 mL of methylene chloride was added. The cloudy solution was stirred for 3 hours and filtered though Celite. The filtrate was washed with water, brine and dried over sodium sulfate. The organic layer was concentrated and purified by flash chromatography (hexanes/ethyl acetate=4/1) to give the desired compound in 52% yield (0.41 g).

Step B:

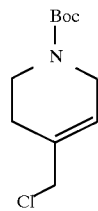

The intermediate obtained from Step A (400 mg, 1.88 mmole) was dissolved in 10 mL benzene and thionyl chloride (0.165 ml, 2.26 mmole) was added and heated to 60° C. for 25 minutes. The resulting mixture was poured into NaHCO$_3$ (aq.) and extracted with ether. The ether layer was dried over magnesium sulfate and concentrated to give desired compound (333 mg, 77%).

Step C:

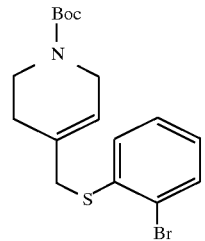

The intermediate obtained from Step B (330 mg, 1.43 mmole) was dissolved in 10 mL of acetone and 2-bromothiophenol (0.172 ml, 1.43 mmole) and potassium carbonate (390 mg, 2.86 mmole) were added. The reaction mixture was heated to 60° C. for an hour and then filtered though silica gel (100% ether). The organic layer was concentrated and purified by flash chromatography (silica gel, hexanes/ethyl acetate=10/1) to give the desired compound in 84% yield (460 mg).

Step D:

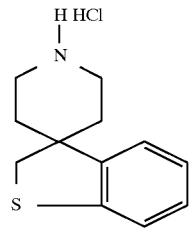

The intermediate obtained from Step C (450 mg, 1.17 mmole) was dissolved in 60 mL of benzene and AIBN (10 mg) and tributyltin hydride (0.644 mL, 2.39 mmole) were added. This mixture was refluxed for 2 hours and concentrated. The residue was dissolved in ether and bromine was added till the reaction solution turned to a brownish color. To this brownish solution at room temperature was added DBU (0.65 mL) in dropwise manner. The resulting cloudy solution was filtered though silica gel and washed with ether. The ether solution was concentrated and the residue was purified by radial chromatography (silica gel, hexanes/ethyl acetate= 10/1) to give desired compound (157 mg) in 43% yield. $^1$H NMR (400 MHz, CDCl$_3$): 7.18 (d, 7 Hz, 1 H), 7.12 (t, 7 Hz, 1 H), 7.06 (m, 2 H), 4.11(m, 2 H), 3.30 (s, 3 H), 2.89 (m, 2 H), 1.79 (m, 4 H), 1.47 (s, 9 H).

The cyclized product was dissolved in ethyl acetate and HCl gas was bubbled at 0° C. until it was saturated. The mixture was stirred at room temperature for 30 minutes and evaporated to give the desired product.

Step E:

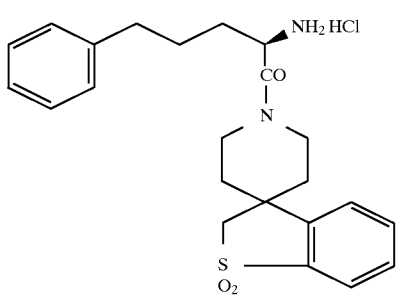

To a solution of the intermediate prepared in Step D (724 mg) in chloroform was added (D)-N-t-Boc-2-amino-5-phenyl pentanoic acid (873 mg), EDC (1.14 g), HOBt (445 mg) and diisopropylethyl-amine (0.57 ml). After 12 hours at room temperature the mixture was poured into 1N HCl and extracted with methylene chloride. The combined organics were dried over sodium sulfate, filtered and concentrated. The residue was purified by chromatotron (hexanes/ethyl acetate=1/1) to give the coupled product. To this product in methanol was added OXONE (4.6 g) at 0° C. and stirred for 1 hour. The mixture was poured into water and extracted with ether. The ether extracts were dried over sodium sulfate, filtered and concentrated to give sulfone. The N-Boc group was removed by treatment with HCl gas at 0° C. in ethyl acetate(1.03 g).

Step F:

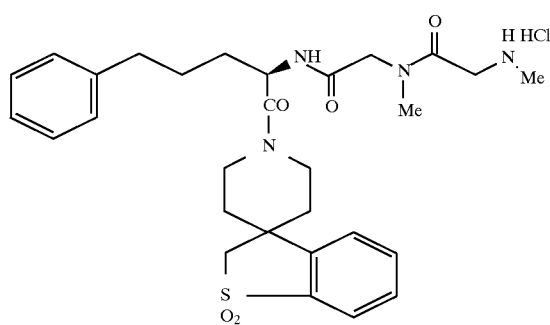

The title compound was prepared from the intermediate obtained from Step E (20 mg) by standard peptide-type coupling and deprotection chemistry. FAB-MS: 555.0 (M+1).

EXAMPLE 27

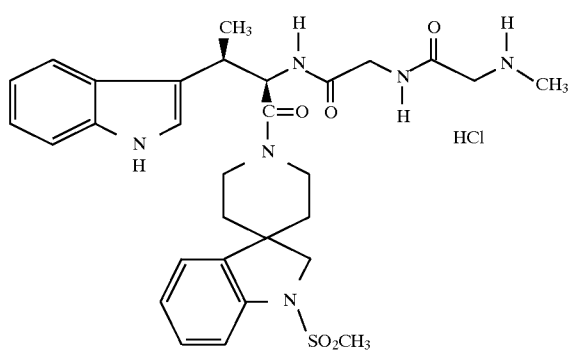

Step A:

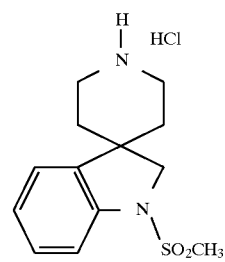

To a solution of 1.20 g (5.8 mmol) of 1'-methyl-1,2-dihydro-spiro[3H-indole-3,4'-piperdine] (prepared as described in H. Ong et al *J. Med. Chem.* 1983, 23, 981–986) in 20 mL of dry dichloromethane at 0° C. was added triethylamine (0.90 mL; 6.4 mmol) and methanesulfonyl chloride (0.49 mL; 6.35 mmol) and stirred for 30 min. The reaction mixture was poured into 15 mL of saturated aqueous sodium bicarbonate solution and extracted with dichloromethane (2×10 mL). The combined organics were washed with brine (20 mL), dried over anhydrous potassium carbonate, filtered and the solvent removed under reduced pressure to yield 1.44 g of the methanesulfonamide derivative as pale yellow oil which was used without purification.

To a solution of above crude product in 20 mL of dry 1,2-dichloroethane at 0° C. was added 1.0 mL (9.30 mmol) of 1-chloroethyl chloroformate, and then stirred at RT for 30 min and finally at reflux for 1 h. The reaction mixture was concentrated to approximately one third of the volume and then diluted with 20 mL of dry methanol and refluxed for 1.5 h. The reaction was cooled to RT and concentrated to approximately one half of the volume. The precipitate was filtered and washed with a small volume of cold methanol. This yielded 1.0 g of the piperidine HCl salt as a white solid. The filtrate was concentrated and a small volume of methanol was added followed by ether. The precipitated material was once again filtered, washed with cold methanol, and dried. This gave an additional 0.49 g of the desired product. Total yield 1.49 g (70%). $^1$H NMR(CDCl$_3$, 200 MHz) d 7.43–7.20 (m, 3H), 7.10 (dd, 1H), 3.98 (bs, 2H), 3.55–3.40 (bd, 2H), 3.35–3.10 (m, 2H), 2.99 (s, 3H), 2.15 (t, 2H), 2.00 (t, 2H).

Step B:

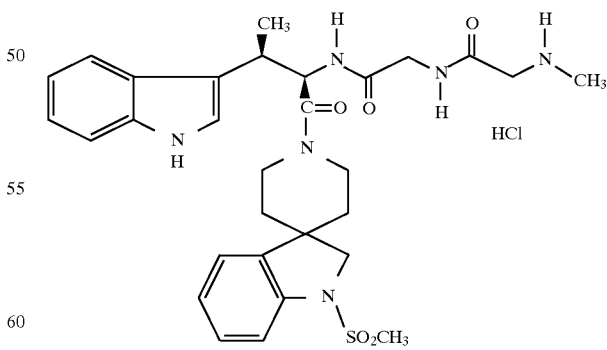

To a suspension of 1.2 g of the piperidine prepared in Step A in 15 mL of acetonitrile was added 0.50 mL of N-methylmorpholine, 1.00 g of (2R, 3R)-N-tBOC-2-methyl-tryptophan (synthesized as described in Example), 0.80 g of HOBT, and 1.00 g of EDC and stirred at RT for 3 h. The reaction mixture was diluted with 100 mL of ether and washed with 50 mL of 0.05N HCl, 50 mL of saturated sodium bicarbonate solution, dried over MgSO$_4$, and concentrated. A solution of the above intermediate in 50 mL of ethyl acetate at 0° C. was treated with HCl (g) for 2 min. and then stirred for 1 h. Dry ether (50 mL) was added, and the precipitated solid was collected by filtration. The yield was 1.44 g.

The above compound was coupled with Intermediate 4 under the standard peptide-type coupling reaction conditions as described above. Purification of the crude product by flash chromatography with dichloromethane-acetone 1:1 as the eluent gave the BOC compound that was deprotected by the HCl/ethyl acetate protocol to give the title compound as a pale yellow solid. $^1$H NMR (CDCl$_3$; 400 MHz).

EXAMPLE 28

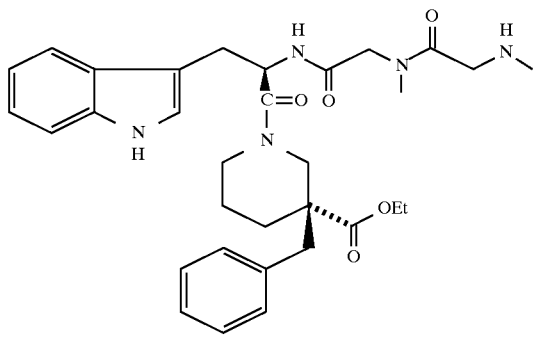

Step A:

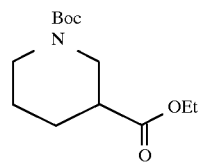

To a stirred solution of ethyl nipecotate (15 g, 95.4 mmol) and DMAP (0.05 eq.) in dichloromethane at 0° C. was added dropwise by an addition funnel di-tert-butyl dicarbonate (21.8 g, 100 mmol) in dichloromethane (200 mL). The mixture was stirred for 2–3 hours. The solution was washed with 3N HCl and saturated sodium chloride, dried over anhydrous magnesium sulfate; then filtered and concentrated to give the desired product (18.7 g, 88%).

Step B:

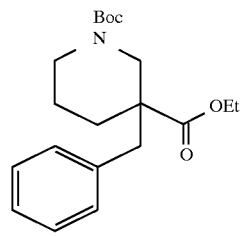

To a stirred solution of ethyl N-t-Boc nipecotate (7 g, 26.90 mmol) in THF (100 mL) at −78° C. under argon was added LHMDS (28 mL, 28 mmol) over a 10 minute period. The solution was allowed to stir an additional 30 minutes at −78° C.; then benzyl bromide (4.8 g, 28 mmol) was added slowly to the solution. The reaction mixture was stirred overnight and allowed to warm to room temperature. The material was concentrated, then diluted with water, and extracted using ethyl acetate (2×200 mL). The organic layer was dried over anhydrous magnesium sulfate, filtered, and concentrated. Purification by silica gel flash column chromatography, eluting with 20% ethyl acetate in hexane, provided the title compound. (8.32 g, 88%). FAB-MS calc. for C$_{20}$H$_{29}$NO$_4$: 347; Found 348 (M+H).

Step C:

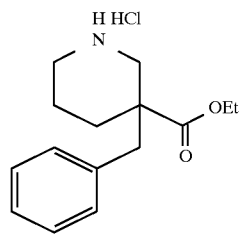

A solution of the intermediate from Step B (8 g, 23.02 mmol) in ethyl acetate (80 mL) was cooled to 0° C. While stirring, hydrogen chloride gas was bubbled into the mixture until saturation occurred. The reaction was stirred for 40 minutes, until TLC analysis indicated that the reaction was complete. The solution was then concentrated to remove the ethyl acetate to afford the product (6.53 g, 99%). $^1$H NMR (CDCl$_3$, 400 MHz) d 7.25–7.19 (m, 3 H), 7.04–7.01 (m, 2 H), 5.35 (v. br. s, 2 H), 4.22–4.10 (m, 2 H), 3.44 (d, J=13 Hz, 1 H), 3.21 (br. d, J=12.7 Hz, 1 H), 2.95 (d, J=13.5 Hz, 1 H), 2.76–2.68 (m, 3 H), 2.22 (br. d, J=13 Hz, 1 H), 1.73–1.71 (m, 1 H), 1.61–1.48 (m, 2 H), 1.18 (t, J=7 Hz, 3 H). FAB-MS calc. for C$_{15}$H$_{21}$NO$_2$: 247; Found 248 (M+H).

Step D:

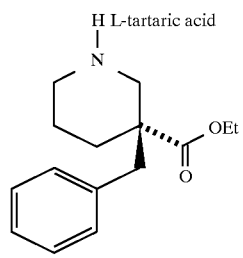

The intermediate from previous step (50.8 g) was dissolved in dichloromethane and it was washed with 3N NaOH. The aqueous layer was extracted with dichloromethane and the combined solution was dried (MgSO$_4$) and evaporated to give the free amine as an oil. The ethyl 3-benzyl nipecotate and D-tartaric acid (31 g) were dissolved in 880 mnL of water/acetone (1:4) solution with heating. The solution was left in the refrigerator overnight and the crystals which were formed were filtered off. Recrystallization in 470 mL of water/acetone (1:4) at room temperature gave the ethyl 3-(R)-benzyl nipecotate D-tartaric acid salt (21 g).

The combined mother liquor was evaporated and to it was added 3N NaOH and dichloromethane, the mixture was stirred for 30 minutes and the organic layer was separated. The aqueous was extracted twice with dichloromethane and the combined organic extracts were dried over MgSO4 and evaporated to give 24.4 g of the S-isomer enriched compound. It was crystallized with L-tartaric acid (14.8 g) in 400 mL of water/acetone (1:4) at room temperature to give ethyl 3 (S)-benzyl nipecotate L-tartaric acid salt (27.3 g). $^1$H NMR (CD$_3$OD, 400 MHz) d 7.31–7.22 (m, 3 H), 7.12–7.09 (m, 2 H), 4.40 (s, 2 H, from tartaric acid), 4.30–4.10 (m, 2 H), 3.49 (br. d, J=13 Hz, 1 H), 3.06 (d, J=13.6 Hz, 1 H), 2.98 (d, J=13 Hz, 1 H), 2.92 (dt, J=3.3 Hz, 13 Hz, 1 H), 2.82 (d, J=13.6 Hz, 1 H), 2.30 (d, J=12.4 Hz, 1 H), 1.88 (td, J=3 Hz, 14.5 Hz, 1 H), 1.69 (dt, J=3 Hz, 13 Hz, 1 H), 1.63–1.51 (m, 1 H), 1.25b (q, J=7.1 Hz, 3 H).

Step E:

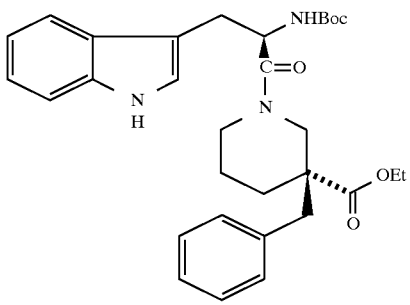

Ethyl 3 (S)-benzyl nipecotate L-tartaric acid salt (39.74 g) was suspended in 70 mL of 3N NaOH and 70 mL of water, followed by extraction with dichloromethane. The extracts were combined, dried, and evaporated to give a thick oil. To a stirred solution of the oil, N-t-Boc D-TrpOH (30.43 g) and HOBt (13.5 g) in dichloromethane (200 mL) at 0° C., was added EDC (23 g) in several portions. The mixture was stirred overnight and it was poured into water and 3N HCl and was extracted with dichloromethane. The organic layer was washed with brine, saturated sodium bicarbonate, dried over MgSO$_4$ and evaporated to give a crude product (67.7 g), which was used without further purification. FAB-MS calc. for C$_{31}$H$_{39}$N$_3$O$_5$: 533; Found 534 (M+H)

Step F:

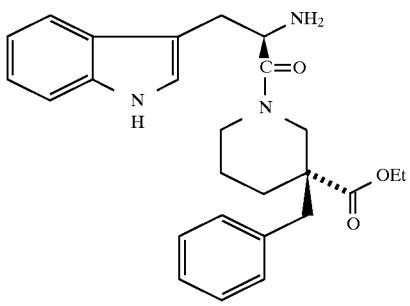

To a solution of the intermediate from the previous step (67.7 g crude) in ethyl acetate (100 mL) at 0° C., was bubbled HCl gas until it was saturated. The reaction mixture was stirred at 0° C. for 30 minutes and was evaporated to remove excess HCl and ethyl acetate. The residue was suspended in dichloromethane and was washed with a mixture of 3N NaOH (70 mL) and water (100 mL). The organic layer was dried (MgSO$_4$), evaporated to a small volume and used in next step without further purification. FAB-MS calc. for C$_{26}$H$_{31}$N$_3$O$_3$: 433; Found 434 (M+H)

Step G:

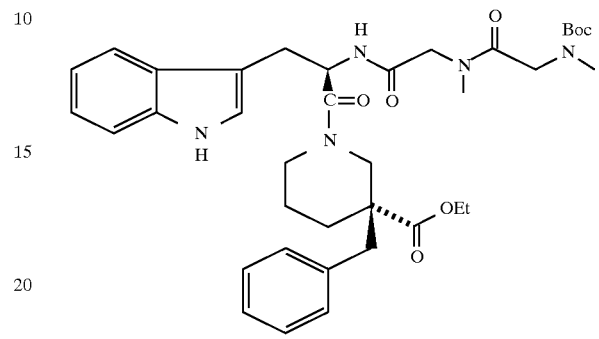

A solution containing the intermediate obtained in the last step (150 mg, 0.319 mmol), N-Boc-Sar-SarOH (83 mg, 0.319 mmol), and HOBT (43 mg) in dichloromethane (100 mL) was stirred at room temperature and to it was added EDC (123 mg). The reaction mixture was stirred overnight and was worked up by diluting it with dichloromethane and washing with 3N HCl, brine, and saturated sodium bicarbonate solution. The organic layer was dried over MgSO$_4$, and evaporated. This residue was purified by MPLC eluting with 7% methanol in ethyl acetate to give the desired compound (188 mg, 87%)

Step H:

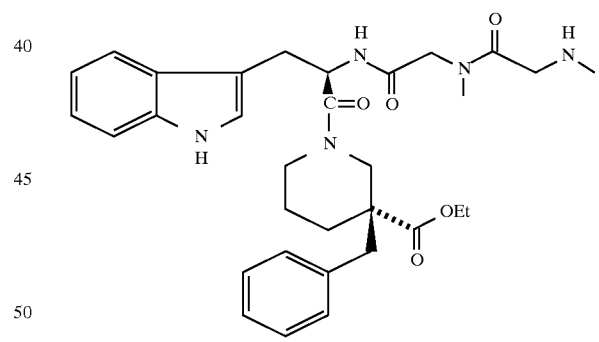

To a solution of the intermediate from the previous step (160 mg, 0.237 mmol) in ethyl acetate (10 mL) at 0° C., was bubbled HCl gas until it was saturated. The reaction mixture was stirred at 0° C. for 15 minutes and was evaporated to remove excess HCl and ethyl acetate to give the salts as white solid (138 mg, 95%). FAB-MS calc. for C$_{32}$H$_{41}$N$_5$O$_5$: 575; Found 576 (M+H)

EXAMPLE 29

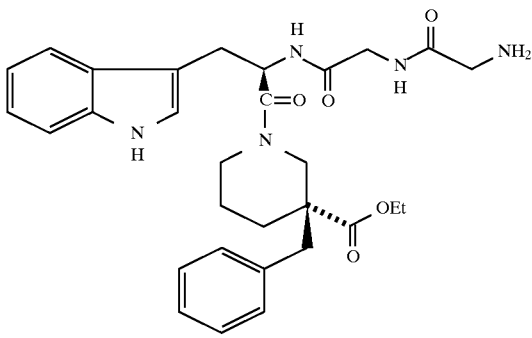

The title compound was prepared according to the similar procedures as discribed in Example 28, but by using Glycine instead of Sarcosine. FAB-MS calc. for $C_{30}H_{37}N_5O_5$: 547; Found 548 (M+H)

EXAMPLE 30

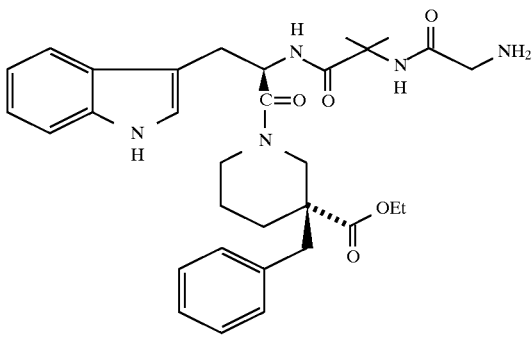

Step A:

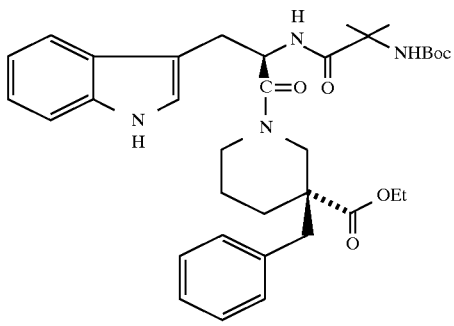

A solution containing the intermediate obtained in the Step F, Example 28, Boc-Aib-OH (Aib: alpha-amino-isobutyric acid, 20.3 g), and DMAP (200 mg) in dichloromethane (100 mL) was stirred at room temperature and to it was added EDC (24 g) in several portions. The reaction mixture was stirred for 3 hours and was worked up by diluting it with dichloromethane and washing with 3N HCl, brine, and saturated sodium bicarbonate solution. The organic layer was dried over $MgSO_4$, and evaporated to give a thick oil. This oil was passed through a pad of silica gel, eluting with 60% ethyl acetate in hexane to remove some very polar impurities, to give the desired compound (54.2 g). FAB-MS calc. for $C_{35}H_{46}N_4O_6$: 618; Found 619 (M+H)

Step B:

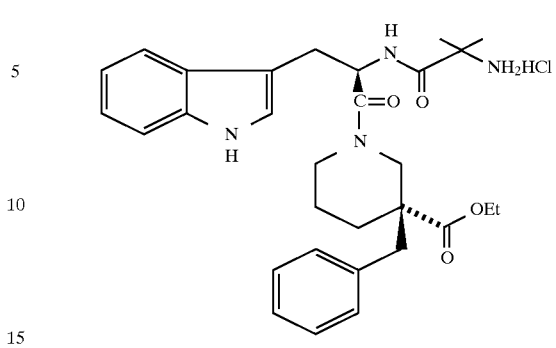

To a solution of the intermediate from the previous step (54.2 g) in ethyl acetate (100 mL) at 0° C., was bubbled HCl gas until it was saturated. The reaction mixture was stirred at 0° C. for 15 minutes and was evaporated to remove excess HCl and ethyl acetate. The residue was first dissolved in dichloromethane (100 mL) and then ethyl acetate (300 mL) was added. The mixture was stirred overnight and the solid was collected by filtration to give the title compound (34 g). Further evaporation of the mother liquor to a small volume gave the second crop of product (10.1 g). FAB-MS calc. for $C_{30}H_{38}N_4O_4$: 518; Found 519 (M+H) $^1$H NMR ($CD_3OD$, 400 MHz) compound exists in two rotamers in approximately a 5/3 ratio that slowly interconvert relative to the NMR time scale d 7.60 (d, J=7.9 Hz, 5/8 H), 7.55 (d, J=7.9 Hz, 3/8 H), 7.34–6.93 (m, 9H), 5.36 (dd, J=5.2 Hz, 9.7 Hz, 3/8 H), 5.31 (dd, J=6.7 Hz, 8.8 Hz, 5/8 H), 4.23 (br. d, J=13.7 Hz, 3/8 H), 4.10–4.00 (m, 6/8 H), 4.04–3.98 (m, 3/8 H), 3.96–3.82 (m, 10/8 H), 3.80(br. d, J=13.5 Hz, 5/8 H), 3.36 (br. d, J=13.3 Hz, 5/8 H), 3.29–3.22, 3.17–3.10, (2m, 2H), 3.20 (br. d, J=14.5 Hz, 3/8 H), 3.10–2.96 (m, 5/8 H), 2.90 (s, 6/8 H), 2.60 (d, J=13.4 Hz, 5/8), 2.41 (d, J=13.4 Hz, 5/8 H), 2.19–2.12, 1.82–1.70, 1.68–1.60, 1.50–1.40, 1.34–1.25, 1.05–0.95 (6m, 4 H),1.55 (s, 9/8 H), 1.50 (s, 15/8 H), 1.09 (t, J=7.1 Hz, 3 H).

Step C:

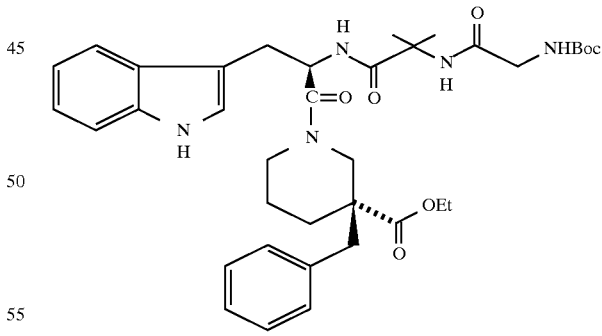

A stirred solution of the intermediate obtained in the previous step (100 mg, 0.18 mmol), N-Boc-GlyOH (32 mg), and HOBT (25 mg) in dichloromethane (10 mL) was added EDC (69 mg). The reaction mixture was stirred overnight and was worked up by diluting it with dichloromethane and washing with 3N HCR, brine, and saturated sodium bicarbonate solution. The organic layer was dried over $MgSO_4$, and evaporated. This residue was purified by MPLC eluting with ethyl acetate to give the desired compound (105 mg, 86%).

Step D:

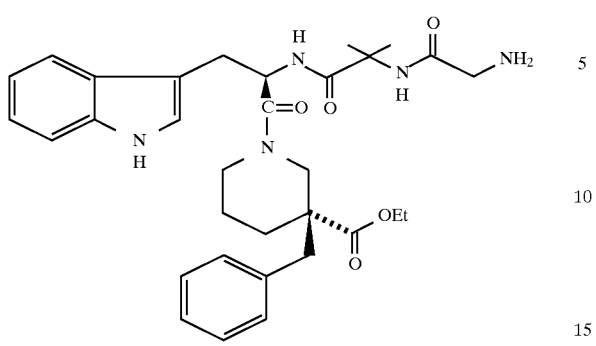

To a solution of the intermediate from the previous step (105 mg, 0.155 mmol) in ethyl acetate (10 mL) at 0° C., was bubbled HCl gas until it was saturated. The reaction mixture was stirred at 0° C. for 15 minutes and was evaporated to remove excess HCl and ethyl acetate to give the salts as white solid (91 mg, 96%). FAB-MS calc. for $C_{32}H_{41}N_5O_5$: 575; Found 576 (M+H).

EXAMPLE 31

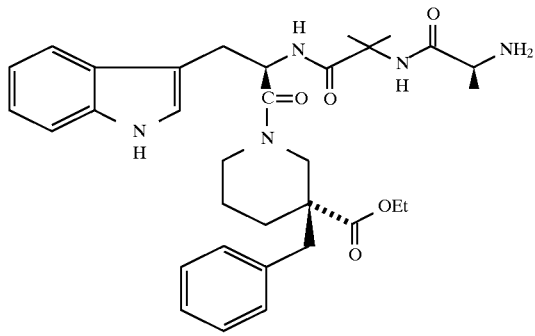

The title compound was prepared according to the same procedure as described above in Examples 28–30, but using the appropriate Boc protected amino acids which were subsequently deprotected as described above. FAB-MS calc. for $C_{33}H_{43}N_5O_5$: 589; Found 590 (M+H)

EXAMPLE 32

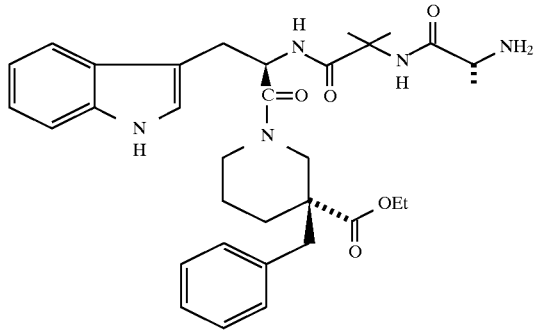

The title compound was prepared according to the same procedure as described above in Examples 28–30, but using the appropriate Boc protected amino acids which were subsequently deprotected as described above. FAB-MS calc. for $C_{33}H_{43}N_5O_5$: 589; Found 590 (M+H)

EXAMPLE 33

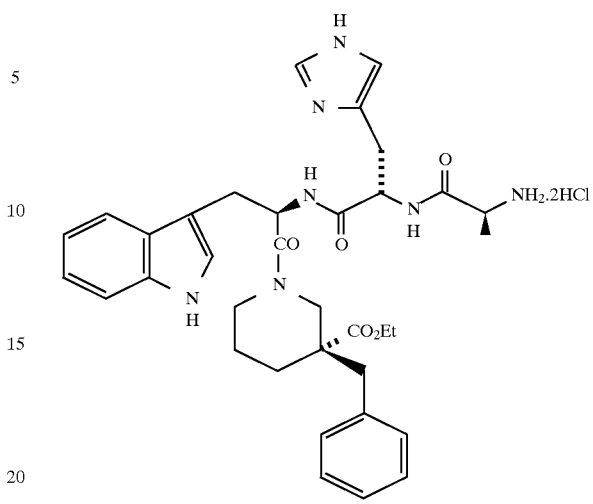

Step A:

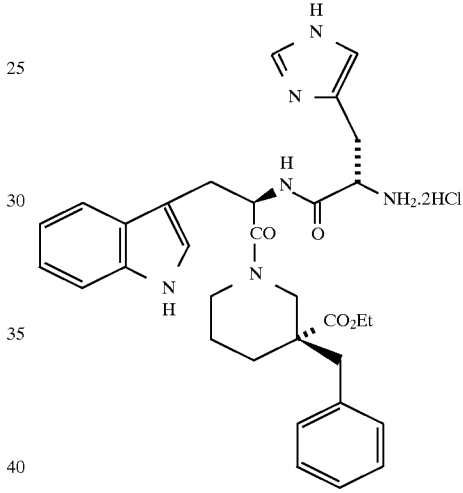

To a cold solution of the product from Example 28, Step F (223 mg) in $CH_2Cl_2$ (3 ml) was added N-methyl-morpholine (0.075 ml), Boc-His(Boc) (205 mg) [obtained from dicyclohexylammonium salt of Boc-His(Boc)], HOBT (114 mg) and EDC (134 mg; 0.699 mmol). The reaction mixture was stirred at room temperature for 2 hours and then partitioned between a mixture of $EtOAc/H_2O$. The organic phase was separated and washed with sat. $NaHCO_3$, water, 10% citric acid, water, then dried over $MgSO_4$, filtered and concentrated in vacuo to give the crude product as a foam. Purification of the crude product by flash chromatography using ethyl acetate as the eluant provided 283 mg of the protected dipeptide. The dipeptide (283 mg) was dissolved in THF (5 ml) and the solution was saturated with with dry HClg for 1 minute. The reaction was sealed and stirred at room temperature for 30 minutes. The solvent and excess reagent were removed in vacuo, and the resulting residue was triturated with EtOAc to give the titled compound (240 mg).

FAB-MS: m/e calculated for $C_{32}H_{38}N_6O_4$: 570; found: 571 (M+H).

Step B:

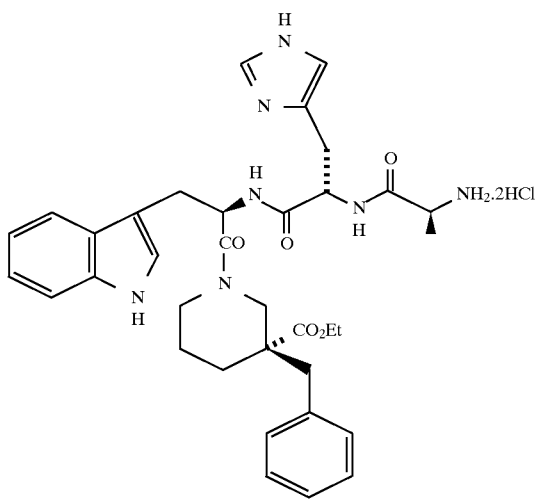

To a cold (0° C.) solution of the titled compound from Step A (126 mg) in CH$_2$Cl$_2$ (2 ml) were added Boc-L-Ala (47 mg), HOBT (50 mg), N-methylmorpholine (49 ml) and EDC (58 mg). The reaction was stirred at room temperature overnight and then partitioned between EtOAc/H$_2$O. The organic phase was separated, washed with 10% NaHCO$_3$, water, 10% citric acid, water, then dried over MgSO$_4$, filtered and concentrated in vacuo. The crude product thus obtained was purified by flash chromatography (20:1 CH$_2$Cl$_2$/MeOH) to provide 81 mg of the Boc-protected tripeptide. The protected tripeptide (81 mg) was then reacted at room temperature with a cold solution of saturated HCl/THF (5 ml) for 1 h. The solvent was removed in vacuo, and the residue was triturated with dry ether to provide the titled compound as a white solid (70 mg). FAB-MS: m/e calculated for C$_{35}$H$_{43}$N$_7$O$_5$: 641; found: 642 (M+H).

EXAMPLE 34

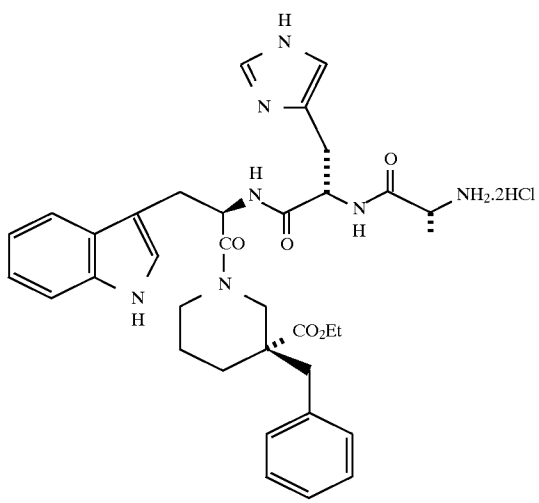

To a cold (0° C.) solution of the titled compound from Example 33, Step A (126 mg) in CH$_2$Cl$_2$ (2 ml) were added Boc-D-Ala (47 mg), HOBT (50 mg), N-methylmorpholine (49 ml) and EDC (58 mg). The reaction was stirred at room temperature overnight, and then partitioned between EtOAc/H$_2$O layers. The organic phase was separated and washed with 10% NaHCO$_3$, water, 10% citric acid, water, then dried over MgSO$_4$, filtered and concentrated in vacuo to give the crude product. Purification of the crude product by flash chromatography (20:1 CH$_2$Cl$_2$/MeOH) provided 85 mg of the Boc-protected tripeptide. The protected tripeptide (85 mg) was then reacted with a cold solution of saturated HCl/THF (5 ml) for 1 h at room temperature. The solvent was removed in vacuo, and the residue was triturated with dry ether to provide the titled compound as a white solid (69 mg). FAB-MS: m/e calculated for C$_{35}$H$_{43}$N$_7$)$_5$: 641; found: 642 (M+H).

EXAMPLE 35

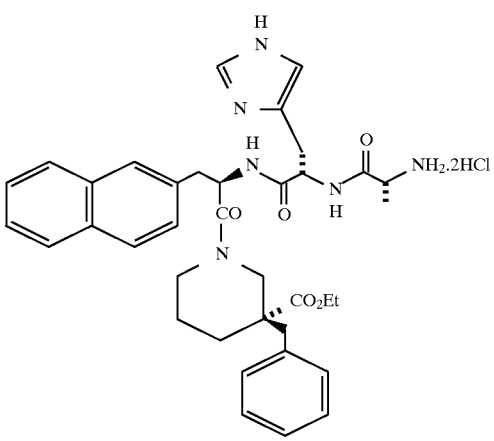

Step A:

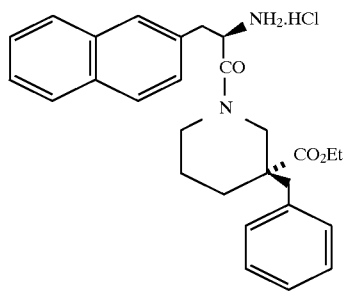

To a solution of Boc-D-β-Nal (0.41 g) in CH$_2$Cl$_2$ (5 ml) at 0° C. were added ethyl-3-(S)-benzyl-nipecotate (0.36 g) (obtained from Example 28, Step C), HOBT (0.282 g), and EDC (0.296 g). The mixture was stirred at room temperature overnight and then partitioned between EtOAc/water. The organic phase was separated and washed with 10% NaHCO$_3$, water, 10% citric acid, water, then dried over MgSO$_4$, filtered and concentrated in vacuo. The crude product, thus obtained, was purified by flash column chromatography on silica-gel using EtOAc-hexanes (1:3) as the eluent to provide the desired Boc-D-b-Nal amide (0.6 g). The protected intermediate was then dissolved in a saturated solution of HCl(g) in EtOAc (6 ml), and the solution was stirred at room temperature for 1 hour. The solvent and excess reagent was removed in vacuo, and the solid residue obtained was triturated with dry ether, filtered and dried in vacuo over P$_2$O$_5$ overnight to give the titled product (0.5 g). FAB-MS: m/e calculated for C$_{28}$H$_{32}$N$_2$O$_3$: 444; found: 445 (M+H).

Step B:

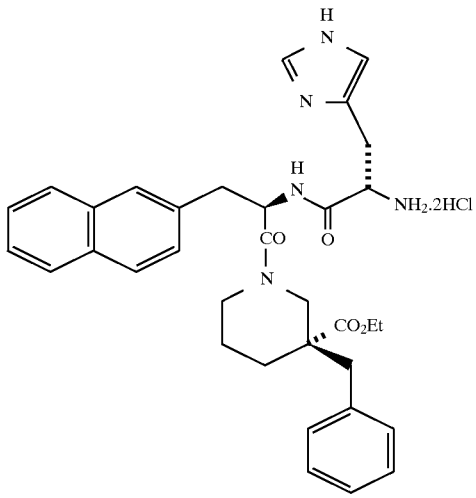

The title compound was prepared from the intermediate obtained in Step A (0.2 g) using the procedure described in Example 33, Step A. FAB-MS: m/e calculated for $C_{34}H_{39}N_5O_4$: 581; found: 582 (M+H).

Step C:

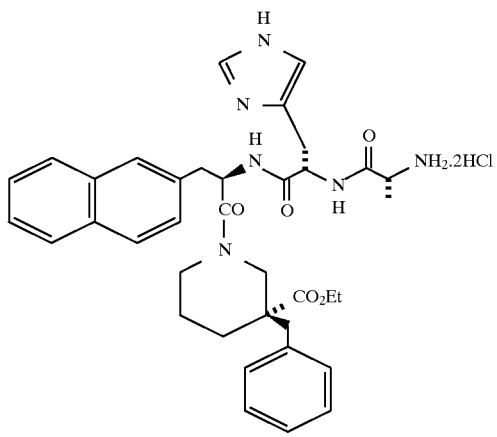

The titled compound was prepared from the intermediate obtained by using the procedure described in Example 34. FAB-MS: m/e calculated for $C_{37}H_{44}N_6O_5$: 652; found: 653 (M+H).

EXAMPLE 36

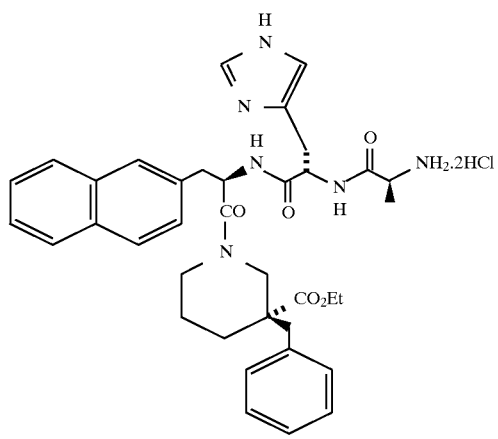

The titled compound was prepared from the intermediate obtained in Example 35, Step B using the procedure described in Example PKC/JM 1, Step B. FAB-MS: m/e calculated for $C_{37}H_{44}N_6O_5$: 652; found: 653 (M+H).

EXAMPLE 37

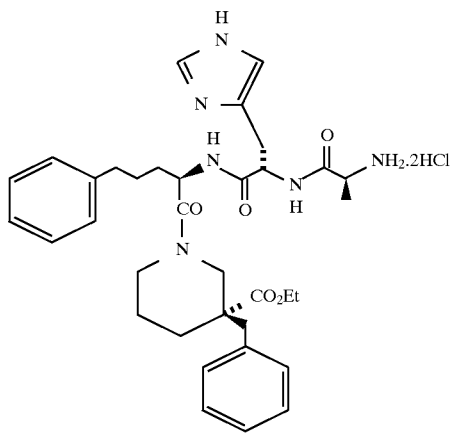

The titled compound was prepared by the procedure described in Example 35, using (D)-N-t-Boc-2-amino-5-phenyl pentanoic acid instead of Boc-D-β-Nal in Step A. FAB-MS: m/e calculated for $C_{35}H_{46}N_6O_5$: 630; found: 631 (M+H).

EXAMPLE 38

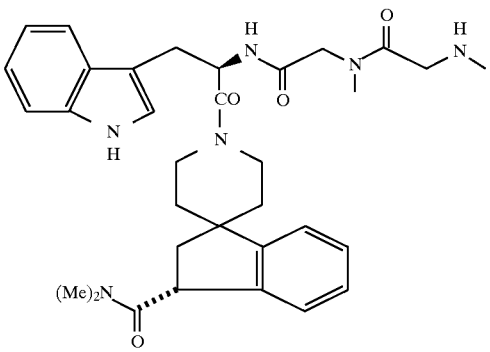

Step A:

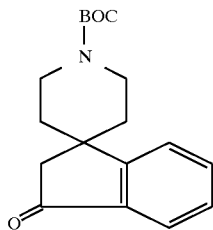

To a solution of 51.0 g (0.177 mol) of 1'-(t-butyloxy-carbonyl) spiro[1H-indene-1,4'-piperidine] [prepared by the method of Chambers, et al, J. Med. Chem., 1992, 35, 2036] in 200 ml of THF was added 430 ml (0.5M in THF, 0.213 mol) of 9-BBN. The reaction mixture was heated at 70° C. until TLC analysis indicated that the starting material was consumed (18 hrs). The solution was concentrated to ~300 ml and then cooled to 0° C. and quenched with methanol (10 ml). 4N Sodium hydroxide (213 ml) and 30% hydrogen peroxide (108 ml) were added via an addition funnel over 45 minutes. The reaction mixture was stirred for 3.5 hours and then solid sodium sulfite was added until starch paper indicated that no more peroxides were present. The reaction mixture was extracted with ethyl acetate (4×1 vol). The ethyl acetate layer was dried over magnesium sulfate filtered and concentrated. The crude material was dissolved in dichloromethane (300 ml) and the solution was cooled to 0° C. then celite (25 g) and PCC (57 g) were added in five portions over 20 minutes. The reaction mixture was warmed to room temperature and stirred overnight. The solution was then diluted with ether and filtered through a pad of a mixture of celite and florisil. Purification by flash chromatography (silica gel, hexane/ethyl acetate, 5:1 to 3:1) gave 58.6 g of the title compound. $^1$H NMR (200 MHz, CDCl$_3$): 7.75–7.60 (m, 2H), 7.50–7.44 (m, 2H), 4.30–4.15 (m, 2H), 2.85 (dt, 2H), 2.63 (s, 2H), 1.98 (dt, 2H), 1.53–1.40 (m, 2H), 1.49 (s, 9H).

Step B:

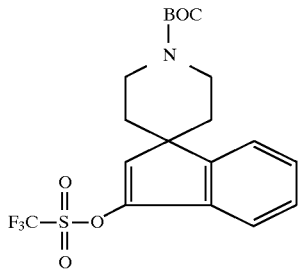

Potasium bis(trimethylsilyl)amide (127.5 ml, 0.5M ) was added to the ketone (16.0 g, 53 mmol) in THF (200 mL) at 0° C. The reaction mixture was stirred for one hour and then N-phenyltrifluro-methanesulfonamide was added. The ice bath was allowed to melt and the reaction mixture was stirred overnight at room temperature. Water was added and the aqueous layer was extracted with ethyl acetate (3×1 vol). The organic layer was washed with brine and then dried over magnesium sulfate, filtered and then concentrated. The crude product was purified by flash chromatography (hexane/ethyl acetate 8:1) to give the title compound (17.8 g) as a waxy solid. $^1$HNMR (200 MHz, CDCl$_3$): 7.65–7.14 (m, 4 H), 6.66 (s, 1 H), 4.30–4.15 (m, 2 H), 3.24–2.96 (m, 2H), 2.06 (dt, 2 H), 1.50 (s, 9 H), 1.49–1.38 (m, 2 H).

Step C:

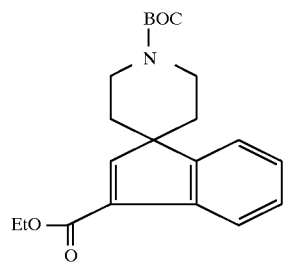

A solution of 17.4 g of the intermediate from Step B, 11.0 ml of triethylamine, 634 mg of triphenylphosphine, and 240 mg of palladium acetate in 72 ml of ethanol and 158.0 ml of DMF was purged for 10 minutes with carbon monoxide and then stirred under a carbon monoxide atmosphere for 24 hours. The ethanol was removed in vacuum and the reaction mixture was diluted with water and extracted repeatedly with ethyl acetate. The ethyl acetate layer was washed with 1N HCl, water, and brine and then dried over magnesium sulfate, filtered and concentrated. Purification by flash chromatography (hexane/ethyl acetate 8:1) provided 27.6 g of the title compound as a colorless oil. $^1$HNMR (200 MHz, CDCl$_3$): 8.0–7.94 (m,1H), 7.7 (s, 1 H), 7.4–7.25 (m, 3H), 4.4 (q,2H), 4.25–4.15 (m, 2H), 3.13 (dt, 2H), 2.03 (dt, 2H), 1.5 (s, 9H), 1.55–1.35 (m, 2H), 1.4 (t, 3H).

Step D:

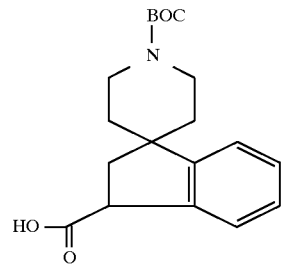

To a suspension of Pd/C (1.7 g) in ethanol (300 ml) was added the title compound (27 g) from Step C. The reaction mixture was purged with hydrogen and then shaken under a hydrogen atmosphere for 3 hours. The mixture was purged with nitrogen and filtered through celite and concentrated to give the title compound (27 g). The crude product was dissolved in ethanol ( 200 ml ) and 2N sodium hydroxide (76 ml) was added. The reaction mixture was heated to 50° C. for three hours then cooled and the ethanol was removed under vacuum and the residue was dissolved in ethyl acetate. 1N HCl was added and the layers were separated and the aqueous layer was extracted with ethyl acetate (3×1 vol). The combined organic layers were washed with saturated aqueous NaCl, dried over anhydrous sodium sulfate, filtered and concentrated to provide the title compound (23.8 g) as a white solid. $^1$HNMR (200 MHz, CDCl$_3$): 7.50–7.42 (m, 1 H), 7.34–7.12 (m, 3 H), 4.22–4.04 (m, 3 H), 3.06–2.84 (m, 2 H), 2.40 (d, 2 H), 1.88–1.6 (m, 4 H), 1.50 (s, 9 H).

Step E:

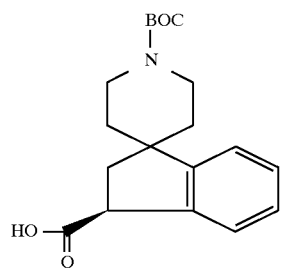

The acid from Step D (23.5 g, 0.07 mol) was dissolved in toluene (150 ml) and R-methylbenzylamine (9.02 ml) was added. The toluene solution was heated on a steam bath until everything was in solution. The solution was then seeded with crystals grown in the same way on a much smaller scale. The solution was allowed to sit overnight and then the mixture was filtered to give 15.8 g of crystals. The crystals were recrystalized from toluene two more times. The crystals (12 g) were dissolved in ethyl acetate/1N HCl and the organic layer was washed with 1N HCL (2×1 vol) and brine. The organic layer was dried over magnesium sulfate, filtered and concentrated to give 8.9 g of the title compound. $[\alpha]^D=-16.9$ (c=0.84, methanol).

Step F:

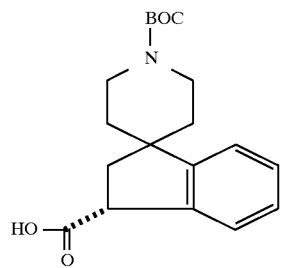

The mother liqueurs from Step E were washed with 1N HCl (2×1 vol) and brine dried over magnesium sulfate filtered and concentrated to give recovered acid (15.4 g). To this acid in toluene (100 mL) was added S-methylbenzylamine (5.95 mL). The crystals were recrystallized four times from toluene as above to give 12.3 g of salt. The salt was dissolved in ethyl acetate/1N HCl and washed with 1N HCl (2×1 vol) and brine. The organic layer was dried over magnesium sulfate and filtered and concentrated to give the title compound (9.0 g). $[\alpha]^D=17.1$ (c=1.06, methanol).

Step G:

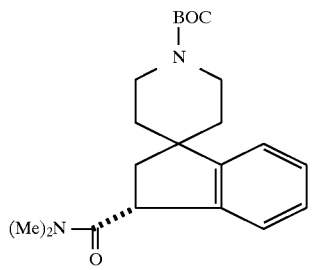

A solution of the title compound from Step F (14.0 g, 42 mMol) in dichloromethane was cooled to 0° and dimethylamine (25.4 mL, 2M in THF) was added. The mixture was stirred for ten minutes at 0° C. and then EDC and DMAP were added. The reaction mixture was stirred for four hours at 0° C. and then quenched with 1N HCl. The aqueous layers were extracted with dichloromethane and the combined organic layers were then washed with water and brine and dried over sodium sulfate. The crude product was purified by flash chromatography (dichloromethane/acetone 9:1) to give the title compound (12.2 g). HPLC analysis (chiralcel OD-R, 50% 0.5N $NaClO_4$/50% acetonitrile, 0.5 ml/min. $E_1$ retention time 20.8 min ($E_1$ prepared from the intermediate in Example 38 Step E as in Example 38 Step G; $E_2$ retention time 24.7 min) showed it to be approximately a 1: 200 mixture of enantiomers. $^1$HNMR (400 MHz, $CDCl_3$): 7.25–7.05(m, 4 H), 4.35 (t,1 H), 4.20–4.10 (m, 2 H), 3.25 (s, 3 H), 3.05 (s, 3 H), 2.90–2.85 (m, 2H), 2.42–2.28 (m, 2H), 1.95 (dt, 1H), 1.75–1.60 (m, 2 H), 1.52–1.50 (m, 1 H), 1.49 (s, 9H).

Step H:

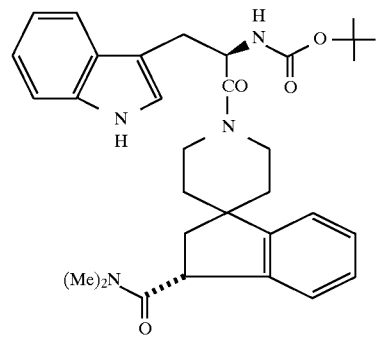

The title compound from Step G (6.4 g, 18.4 mmol) was stirred in ethyl acetate saturated with HCl for two hours and then concentrated and azeotroped from dichloromethane (2×) and toluene (1×). The residue was dissolved in dichloromethane, cooled to 0° C. and Boc-D-tryptophan (6.2 g,20.2 mMol), NMM (2.0 mL, 18.4 mMol), HOBT (3.7 g, 27.6 mMol) and finally EDC (5.27 g, 27.6 mMol) were added. The reaction mixture was stirred at room temperature overnight and then poured into ethyl acetate. The organic layer was washed with saturated bicarb, 1N HCl, water and finally brine. The organic layers were dried over magnesium sulfate, filtered and concentrated. Purification by flash chromatography (ethyl acetate) gave the title compound (4.6 g).

Step I:

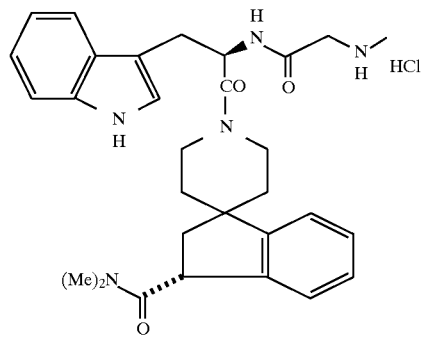

The title compound from Step H (111 mg, 0.230 mMol) was deprotected with ethyl acetate/HCl as above. The residue was coupled to Boc-sarcosine using the procedure for Step H. The reaction mixture was loaded directly onto a flash column and eluted with dichloromethane/acetone (1:1) to give the Boc protected product (122 mg). This material was deprotected as above with ethyl acetate/HCl to give the title compound (120 mg).

Step J:

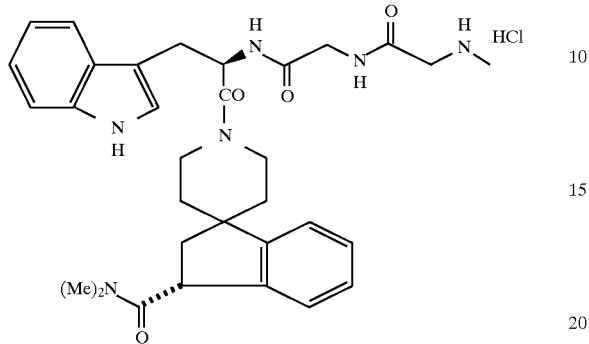

The title compound from Step J (40 mg 0.074 mMol) was coupled to Boc-sarcosine as in Step I. Purification of the crude product by flash chromatography (dichloromethane/acetone 1:1) gave the Boc protected title compound (43 mg). Removal of the Boc group with ethyl acetate/HCl followed by purification by MPLC (LH$_{20}$, methanol) gave the title compound (34 mg). ESI-MS: 587.3 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula:

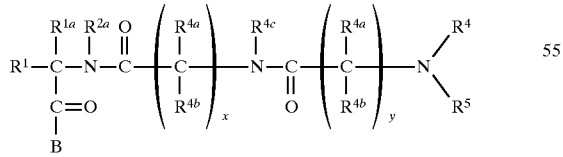

wherein:
R$^1$ is selected from the group consisting of:
C$_1$–C$_{10}$ alkyl, -aryl-, aryl (C$_1$–C$_6$ alkyl)-, heteroaryl-, heteroaryl(C$_1$–C$_6$ alkyl)-, (C$_3$–C$_7$ cycloalkyl)-(C$_1$–C$_6$ alkyl)-, (C$_1$–C$_5$ alkyl)-K-(C$_1$–C$_5$ alkyl)-, aryl-(C$_0$–C$_5$ alkyl)-K-(C$_1$–C$_5$ alkyl)-,
heteroaryl-(C$_0$–C$_5$ alkyl)-K-(C$_1$–C$_5$ alkyl)-, and (C$_3$–C$_7$ cycloalkyl)-(C$_0$–C$_5$ alkyl)-K-(C$_1$–C$_5$ alkyl)-,
wherein K is —O—, —S(O)$_m$—, —N(R$^2$)C(O)—, —C(O)N(R$^2$)—, —OC(O)—, —C(O)O—, —CR$^2$=CR$^2$— or —C≡C—,
wherein R$^2$ and the alkyl groups may be further substituted with 1 to 9 halo, —S(O)$_m$R$^{2a}$, 1 to 3 of —OR$^{2a}$, or —C(O)OR$^{2a}$, and wherein aryl is phenyl or naphthyl, and heteroaryl is selected from indolyl, thiophenyl, benzofuranyl, benzothipheneyl, azaindolyl, pyridinyl, quinolinyl, and benzimidazolyl, wherein aryl and heteroaryl are unsubstituted or substituted with phenyl, phenoxy, halophenyl, 1 to 3 of —C$_1$–C$_6$ alkyl, 1 to 3 of halo, 1 to 2 of —OR$^2$, methylenedioxy, —S(O)$_m$R$^2$, 1 to 2 of —CF$_3$, —OCF$_3$, nitro, —N(R$^2$)(R$^2$), —N(R$^2$)C(O)(R$^2$), —C(O)OR$^2$, —C(O)N(R$^2$)(R$^2$), —SO$_2$N(R$^2$)(R$^2$), —N(R$^2$)SO$_2$-aryl, or —N(R$^2$)SO$_2$R$^2$;
R$^{1a}$ is hydrogen or C$_1$–C$_4$ alkyl;
R$^2$ is selected from the group consisting of:
hydrogen, —C$_1$–C$_6$ alkyl, —C$_3$–C$_7$ cycloalkyl, and —CH$_2$-phenyl, wherein the alkyl or the cyloalkyl is unsubstituted or substituted with hydroxyl, C$_1$–C$_3$ alkoxy, thioalkyl, C(O)OR$^{2a}$, and where, if two —C$_1$–C$_6$ alkyl groups are present on one atom, they may be joined to form a C$_3$–C$_8$ cyclic ring being selected from the group consisting of pyrrolidine, piperidine, piperazine, morpholine, thiomorpholine, optionally substituted by hydroxyl;
R$^{2a}$ is hydrogen or C$_1$–C$_6$ alkyl;
B is selected from:

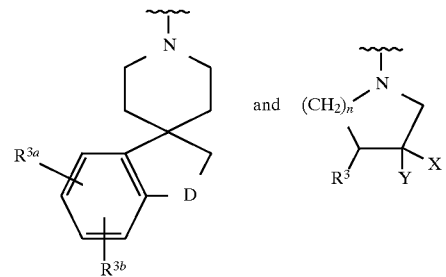

R$^3$ is selected from: hydrogen, —(CH$_2$)$_r$phenyl, —(CH$_2$)$_r$thienyl, —(CH$_2$)$_r$benzimidazolyl, —(CH$_2$)$_r$quinolinyl, —(CH$_2$)$_r$naphthyl, —(CH$_2$)$_r$indolyl, —C$_1$–C$_{10}$ alkyl, —C$_3$–C$_7$ cycloalkyl, where the phenyl, naphthyl, indolyl, thienyl, benzimidazolyl, quinolinyl, and C$_3$–C$_7$ cycloalkyl rings may be substituted by 1 to 3 substituents selected from the group consisting of: C$_1$–C$_6$ alkyl, halogen, —OR$^2$, —NHSO$_2$CF$_3$, —(CH$_2$)$_r$OR$^6$, —(CH$_2$)$_r$N(R$^2$)(R$^6$), —(CH$_2$)$_r$(R$^6$), —(CH$_2$)$_r$C(O)OR$^2$, —(CH$_2$)$_r$C(O)OR$^6$, —(CH$_2$)$_r$OC(O)R$^2$, —(CH$_2$)$_r$OC(O)R$^6$, —(CH$_2$)$_r$C(O)R$^2$, —(CH$_2$)$_r$C(O)R$^6$, —(CH$_2$)$_r$C(O)N(R$^2$)(R$^2$), —(CH$_2$)$_r$C(O)N(R$^2$)(R$^6$), —(CH$_2$)$_r$N(R$^2$)C(O)(R$^2$), —(CH$_2$)$_r$N(R$^2$)C(O)R$^6$ —(CH$^2$)$_r$N(R$^6$)C(O)R$^2$, —(CH$_2$)$_r$N(R$^6$)C(O)R$^6$, —(CH$_2$)$_r$N(R$^2$)C(O)OR$^2$, —(CH$_2$)$_r$N(R$^2$)C(O)OR$^6$, —(CH$_2$)$_r$N(R$^6$)C(O)OR$^2$, —(CH$_2$)$_r$N(R$^6$)C(O)OR$^6$, —(CH$_2$)$_r$N(R$^2$)C(O)N(R$^2$)(R$^6$), —(CH$_2$)$_r$N(R$^2$)C(O)N(R$^2$)(R$^2$), —(CH$_2$)$_r$N(R$^6$)C(O)N(R$^2$)(R$^6$), —(CH$_2$)$_r$N(R$^2$)SO$_2$R$^2$, —(CH$_2$)$_r$N(R$^6$)SO$_2$R$^2$, —(CH$_2$)$_r$N(R$^6$)SO$_2$R$^6$, —(CH$_2$)$_r$OC(O)N(R$^2$)(R$^6$), —(CH$_2$)$_r$OC(O)N(R$^2$)(R$^2$), —(CH$_2$)$_r$SO$_2$N(R$^2$)(R$^6$), —(CH$_2$)$_r$OC(O)N(R$^2$)(R$^2$), —(CH$_2$)$_r$SO$_2$N(R$^2$)(R$^6$), —(CH$_2$)$_r$SO$_2$N(R$^2$)(R$^2$), —(CH$_2$)$_r$N(R$^2$)SO$_2$N(R$^2$)(R$^6$), —(CH$_2$)$_r$N(R$^6$)SO$_2$N(R$^2$)(R$^6$), —(CH$_2$)$_r$S(O)$_m$R$^6$, and —(CH$_2$)$_r$S(O)$_m$R$^2$;

R$^{3a}$ and R$^{3b}$ are independently selected from: hydrogen, phenyl, phenoxy, halophenyl, —C$_1$–C$_6$ alkyl, halogen, —OR$^2$, methylenedioxy, —S(O)$_m$R$^2$, —CF$_3$, —OCF$_3$, nitro, —N(R$^2$)(R$^2$), —N(R$^2$)C(O)(R$^2$), —C(O)OR$^2$, —C(O)N(R$^2$)(R$^2$), —SO$_2$N(R$^2$)(R$^2$), —N(R$^2$)SO$_2$-aryl, and —N(R$^2$)SO$^2$R$^2$;

R$^4$ and R$^5$ are independently selected from hydrogen, C$_1$–C$_6$ alkyl, and substituted C$_1$–C$_6$ alkyl where the substituents are selected from halo, hydroxy, phenyl, and C$_1$–C$_6$ alkoxycarbonyl;

or R$^5$ and R$^4$ may be taken together to form —(CH$_2$)$_d$-L$_a$(CH$_2$)$_e$— where L$_a$ is —C(R$^2$)$_2$—, —O—, —S(O)$_m$ —or —N(R$^2$)—, d and e are independently 1 to 3 and R$^2$ is as defined above;

R$^{4a}$ and R$^{4b}$ are independently selected from: hydrogen, C$_1$–C$_6$ alkyl, trifluoromethyl, phenyl, or substituted C$_1$–C$_6$ alkyl where the substituents are selected from: imidazolyl, naphthyl, phenyl, indolyl, p-hydroxyphenyl, —OR$^2$, —S(O)$_m$R$^2$, —C(O)OR$^2$, C$_3$–C$_7$ cycloalkyl, —N(R$^2$)(R$^2$), —C(O)N(R$^2$)(R$^2$); or R$^{4a}$ and R$^{4b}$ may independently be joined to one or both of R$^4$ or R$^{4c}$ to form an alkylene bridge between the terminal nitrogen and the alkyl portion of the R$^{4a}$ or R$^{4b}$ and the R$^4$ or R$^{4c}$ group, wherein the bridges contain 1 to 8 carbons atoms; or R$^{4a}$ and R$^{4b}$ may be joined to one another to form C$_3$–C$_7$ cycloalkyl;

R$^{4c}$ is selected from hydrogen, C$_1$–C$_6$ alkyl, and substituted C$_1$–C$_6$ alkyl where the substituents are selected from 1 to 5 halo, 1 to 3 hydroxy, phenyl, napthyl, imidazolyl, indolyl, and C$_1$–C$_6$ alkoxycarbonyl;

R$^6$ is selected from: hydrogen, C$_1$–C$_6$ alkyl, and (CH$_2$)$_v$aryl, wherein the (CH$_2$)$_v$ and alkyl groups may be optionally substituted by —O(R$^2$), —S(O)$_m$R$^2$, —C(O)OR$^2$, —C(O)N(R$^2$)(R$^2$), —SO$_2$N(R$^2$)(R$^2$), or —N(R$^2$)C(O)N(R$^2$)(R$^2$), wherein the aryl group is selected from: phenyl, pyridyl, 1H-tetrazolyl, triazolyl, oxadiazolyl, pyrazolyl, thiadiazoyl, and benzimidazol-2-yl, which is optionally substituted with C$_1$–C$_6$ alkyl, C$_3$–C$_6$ cycloalkyl, amino, or hydroxyl;

X is selected from the group consisting of: hydrogen, —C≡N, —(CH$_2$)$_q$N(R$^2$)C(O)R$^2$, —(CH$_2$)$_q$N(R$^2$)C(O)(CH$_2$)$_t$aryl, —(CH$_2$)$_q$N(R$^2$)SO$_2$(CH$_2$)$_t$aryl, —(CH$_2$)$_q$N(R$^2$)SO$_2$R$^2$, —(CH$_2$)$_q$N(R$^2$)C(O)N(R$^2$)(CH$_2$)$_t$aryl, —(CH$_2$)$_q$N(R$^2$)C(O)N(R$^2$)(R$^2$), —(CH$_2$)$_q$C(O)N(R$^2$)(R$^2$), —(CH$_2$)$_q$C(O)N(R$^2$)(CH$_2$)$_t$aryl, —(CH$_2$)$_q$C(O)OR$^2$, —(CH$_2$)$_q$C(O)O(CH$_2$)$_t$aryl, —(CH$_2$)$_q$OR$^2$, —(CH$_2$)$_q$OC(O)R$^2$, —(CH$_2$)$_q$OC(O)(CH$^2$)$_t$aryl, —(CH$_2$)$_q$OC(O)N(R$^2$)(R$^2$), —(CH$_2$)$_q$C(O)R$^2$, —(CH$_2$)$_q$C(O)(CH$_2$)$_t$aryl, —(CH$_2$)$_q$N(R$^2$)C(O)OR$^2$, —(CH$_2$)$_q$N(R$^2$)SO$_2$N(R$^2$)(R$^2$), —(CH$_2$)$_q$S(O)$_m$R$^2$, and —(CH$_2$)$_q$S(O)$_m$(CH$_2$)$_t$aryl, where R$^2$, (CH$_2$)$_q$ and (CH$_2$)$_t$ group may be optionally substituted with C$_1$–C$_4$ alkyl, hydroxyl, C$_1$–C$_4$ lower alkoxy, carboxyl, N(R$^2$)(R$^2$), CONH$_2$, S(O)$_m$CH$_3$, carboxylate C$_1$–C$_4$ alkyl esters, or 1H-tetrazol-5-yl, and aryl is phenyl, naphthyl, pyridyl, thiazolyl, or 1H-tetrazol-5-yl groups which may be optionally substituted with halogen, —OR$^2$, —CON(R$^2$)(R$^2$), —C(O)OR$^2$, C$_1$–C$_4$ alkyl, -S(O)$_m$R$^2$, or 1H-tetrazol-5-yl;

Y is selected from the group consisting of: hydrogen, C$_1$–C$_{10}$ alkyl, —(CH$_2$)$_t$aryl, —(CH$_2$)$_q$(C$_3$–C$_7$ cycloalkyl), —(CH$_2$)$_q$-K-(C$_1$–C$_6$ alkyl), —(CH$_2$)$_q$-K-(CH$_2$)$_t$aryl, —(CH$_2$)$_q$-K-(CH$_2$)$_t$(C$_3$–C$_7$ cycloalkyl containing O, NR$_2$S) and —(CH$_2$)$_q$-K-(CH$_2$)$_t$(C$_3$–C$_7$ cycloalkyl), where K is O, S(O)$_m$, C(O)NR$^2$, CH=CH, C≡C, N(R$^2$)C(O), C(O)NR$^2$, C(O)O, or OC(O), and where the alkyl, R$^2$, (CH$_2$)$_q$ and (CH$_2$)$_t$ groups are optionally substituted by C$_1$–C$_4$ alkyl, hydroxyl, C$_1$–C$_4$ lower alkoxy, carboxyl, —CONH$_2$ or a carboxylate C$_1$–C$_4$ alkyl ester, and aryl is phenyl, naphthyl, pyridyl, 1-H-tetrazol-5-yl, thiazolyl, imidazoly, indolyl, oxadiazoyl, pyrimidinyl, thiadiazolyl, pyrazolyl, oxazolyl, isoxazolyl, thiopheneyl, quinolinyl, pyrrazinyl, or isothiazolyl which is optionally substituted with halogen, —OR$^2$, —C(O)OR$^2$, N(R$^2$)(R$^2$), —C(O)N(R$^2$)(R$^2$), nitro, cyano, benzyl, C$_1$–C$_4$ alkyl, —S(O)$_m$R$^2$, or 1H-tetrazol-5-yl;

D is selected from: —N(R$^7$)—, —S(O)$_m$—, —C(O)— and —C(H)(R$^7$)—, wherein R$^7$ is selected from: —R$^2$, —OR$^2$, —(CH$_2$)$_q$aryl, —C(O)R$^2$, —C(O)(CH$_2$)$_q$aryl, —SO$_2$R$^2$, —SO$_2$(CH$_2$)$_q$aryl, —C(O)N(R$^2$)(R$^2$), —C(O)N(R$^2$)(CH$_2$)$_q$aryl, —C(O)oR$^2$, 1-H-tetrazol-5-yl, -SO$_2$N(R$^2$)aryl, —SO$_2$N(R$^2$)(R$^2$) and the (CH$_2$)$_q$ may be optionally substituted by C$_1$–C$_4$ alkyl, and the R$^2$ and aryl may be optionally further substituted with a substituent selected from: —OR$^{2a}$, —O(CH$_2$)$_q$ aryl, —C(O)OR$^{2a}$, —C(O)(CH$_2$)$_q$ aryl, —C(O)N(R$^{2a}$)(R$^{2a}$), —C(O)N(R$^{2a}$)(CH$_2$)$_1$ aryl, halogen, —N(R$^{2a}$)(R$^{2a}$), —C$_1$–C$_4$ alkyl, 1,2,4—triazolyl, 1-H-tetrazol-5-yl, —C(O)NHSO$_2$R$^{2a}$, —S(O)$_m$R$^{2a}$, —C(O)NHSO$_2$(CH$_2$)$_q$aryl, —N(R$^2$)C(O)N(R$^{2a}$)(R$^{2a}$), —N(R$^{2a}$)C(O)N(R$^{2a}$)(CH$_2$)$_q$aryl, —N(R$^{2a}$)(R$^{2a}$), N(R$^{2a}$)C(O)R$^{2a}$, —N(R$^{2a}$)C(O)(CH$_2$)$_q$ aryl, —OC(O)N(R$^{2a}$)(R$^{2a}$), —OC(O)N(R$^{2a}$)(CH$_2$)$_q$ aryl;

1 is 0, 1 or 2;

m is 0, 1, or 2;

n is 2;

q is 0, 1, 2, 3, or 4;

r is 0, 1, 2, or 3;

t is 0, 1, 2, or 3;

v is 0, 1, or 2;

x is 1; y is 1;

and pharmaceutically acceptable salts and individual diastereomers thereof.

2. The compound of claim 1 of the formula:

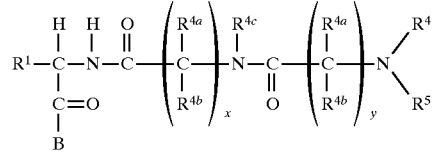

wherein:

R$^1$ is selected from the group consisting of:
C$_1$–C$_{10}$ alkyl, -aryl-, aryl (C$_1$–C$_6$ alkyl)-,
heteroaryl-, heteroaryl(C$_1$–C$_6$ alkyl)-,
(C$_3$–C$_7$ cycloalkyl)—(C$_1$–C$_6$ alkyl)-,
(C$_1$–C$_5$ alkyl)-K-(C$_1$–C$_5$ alkyl)-,
aryl—(C$_0$–C$_5$ alkyl)-K-(C$_1$–C$_5$ alkyl)-,
heteroaryl—(C$_0$–C$_5$ alkyl)-K-(C$_1$–C$_5$ alkyl)-, and
(C$_3$–C$_7$ cycloalkyl)-(C$_0$–C$_5$ alkyl)-K-(C$_1$–C$_5$ alkyl)-,
wherein K is —O—, —S(O)$_m$—, —N(R$^2$)C(O)—, —C(O)N(R$^2$)—, —OC(O)—, —C(O)O—, —CR$^2$=CR$^2$— or —C≡C—, wherein $R^2$ and the alkyl groups may be further substituted with 1 to 9 halo, —S(O)$_m$R$^{2a}$, 1 to 3 of —OR$^{2a}$, or —C(O)OR$^{2a}$, and wherein aryl is phenyl or naphthyl, and heteroaryl is selected from indolyl, thiophenyl, benzofuranyl, benzothiopheneyl, aza-indolyl, pyridinyl, quinolinyl, and benzimidazolyl, wherein aryl and heteroaryl are unsubstituted or substituted with phenyl, phenoxy, halophenyl, 1 to 3 of —C$_1$–C$_6$ alkyl, 1 to 3 of halo, 1 to 2 of —OR$^2$, methylenedioxy, —S(O)$_m$R$^2$, 1 to 2 of —CF$_3$, —OCF$_3$, nitro, —N(R$^2$)(R$^2$), —N(R$^2$)C(O)(R$^2$), —C(O)OR$^2$, —C(O)N(R$^2$)(R$^2$), —SO$_2$N(R$^2$)(R$^2$), —N(R$^2$)SO$_2$-aryl, or —N(R$^2$)SO$_2$R$^2$;

$R^2$ is selected from the group consisting of: hydrogen, —C$_1$–C$_6$ alkyl, —C$_3$–C$_7$ cycloalkyl, and —CH$_2$-phenyl, wherein the alkyl or the cyloalkyl is unsubstituted or substituted with hydroxyl, C$_1$–C$_3$ alkoxy, thioalkyl, —C(O)OR$^{2a}$, and wherein, if two —C$_1$–C$_6$ alkyl groups are present on one atom, the groups may be optionally joined to form a C$_3$–C$_8$ cyclic ring being selected from the group consisting of pyrrolidine, piperidine, piperazine, morpholine, thiomorpholine;

B is selected from:

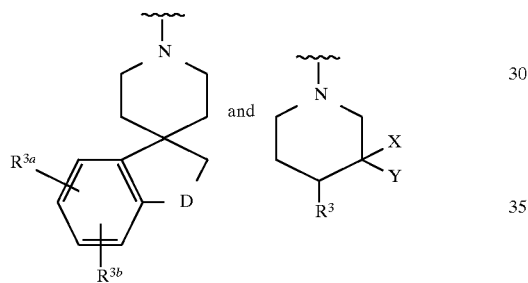

$R^3$ is selected from: hydrogen, phenyl, naphthyl, indolyl, benzimidazolyl, thienyl, quinolinyl, where the phenyl, naphthyl, benzimidazolyl, thienyl, quinolinyl, and indolyl may be substituted by 1 to 3 substituents selected from the group consisting of: C$_1$–C$_6$ alkyl, halogen, —OR$^2$, —(CH$_2$)$_r$OR$^6$, —(CH$_2$)$_r$N(R$^2$)(R$^6$), —(CH$_2$)$_r$(R$^6$), —(CH$_2$)$_r$C(O)OR$^2$, —(CH$_2$)$_r$C(O)OR$^6$, —(CH$_2$)$_r$C(O)R$^2$, —(CH$_2$)$_r$C(O)R$^6$, —(CH$_2$)$_r$C(O)N(R$^2$)(R$^2$), —(CH$_2$)$_r$C(O)N(R$^2$)(R$^6$), —(CH$_2$)$_r$N(R$^2$)C(O)(R$^2$), —(CH$_2$)$_r$N(R$^2$)C(O)R$^6$ —(CH$_2$)$_r$N(R$^6$)C(O)R$^2$, —(CH$_2$)$_r$N(R$^6$)C(O)R$^6$, —(CH$_2$)$_r$N(R$^2$)C(O)OR$^2$, —(CH$_2$)$_r$N(R$^2$)C(O)OR$^6$, —(CH$_2$)$_r$N(R$^6$)C(O)OR$^2$, —(CH$_2$)$_r$N(R$^6$)C(O)OR$^6$, —(CH$_2$)$_r$N(R$^2$)C(O)N(R$^2$)(R$^6$), —(CH$_2$)$_r$N(R$^2$)C(O)N(R$^2$)(R$^2$), —(CH$_2$)$_r$N(R$^6$)C(O)N(R$^2$)(R$^6$), —(CH$_2$)$_r$N(R$^2$)SO$_2$R$^2$, —(CH$_2$)rN(R$^6$)SO$_2$R$^2$, —(CH$_2$)$_r$N(R$^6$)SO$_2$R$^6$, —(CH$_2$)$_r$OC(O)N(R$^2$)(R$^6$), —(CH$_2$)$_r$SO$_2$N(R$^2$)(R$^6$), —(CH$_2$)$_r$SO$_2$N(R$^2$)(R$^6$), —(CH$_2$)$_r$SO$_2$N(R$^2$)(R$^2$), —(CH$_2$)$_r$S(O)$_m$R$^6$, and —(CH$_2$)$_r$S(O)$_m$R$^2$;

$R^{3a}$ and $R^{3b}$ are independently selected from: hydrogen, phenyl, phenoxy, halophenyl, —C$_1$–C$_6$ alkyl, halogen, —OR$^2$, methylenedioxy, —S(O)$_m$R$^2$, —CF$_3$, —OCF$_3$, nitro, —N(R$^2$)(R$^2$), —N(R$^2$)C(O)(R$^2$), —C(O)OR$^2$, —C(O)N(R$^2$)(R$^2$), —SO$_2$N(R$^2$)(R$^2$), —N(R$^2$)SO$_2$-aryl, and —N(R$^2$)SO$^2$R$^2$;

$R^4$ and $R^5$ are independently selected from hydrogen, C$_1$–C$_6$ alkyl, and substituted C$_1$–C$_6$ alkyl where the substituents are selected from halo, hydroxy, phenyl, and C$_1$–C$_6$ alkoxycarbonyl;

or $R^5$ and $R^4$ may be taken together to form —(CH$_2$)$_d$—L$_a$(CH$_2$)e— where L$_a$ is —C(R$^2$)$_2$—, —O—, —S(O)$_m$— or —N(R$^2$)—, d and e are independently 1 to 3 and $R^2$ is as defined above;

$R^{4a}$ and $R^{4b}$ are independently selected from: hydrogen, C$_1$–C$_6$ alkyl, trifluoromethyl, phenyl, or substituted C$_1$–C$_6$ alkyl where the substituents are selected from: imidazolyl, naphthyl, phenyl, indolyl, p-hydroxyphenyl, —OR$^2$, —S(O)$_m$R$^2$, —C(O)OR$^2$, C$_3$–C$_7$ cycloalkyl, —N(R$^2$)(R$^2$), —C(O)N(R$^2$)(R$^2$); or $R^{4a}$ and $R^{4b}$ may independently be joined to one or both of $R^4$ or $R^{4c}$ to form an alkylene bridge between the terminal nitrogen and the alkyl portion of the $R^{4a}$ or $R^{4b}$ and the $R^4$ or $R^{4c}$ group, wherein the bridges contain 1 to 5 carbons atoms; or $R^{4a}$ and $R^{4b}$ may be joined to one another to form C$_3$–C$_7$ cycloalkyl;

$R^{4c}$ is selected from hydrogen, C$_1$–C$_6$ alkyl, and substituted C$_1$–C$_6$ alkyl where the substituents are selected from 1 to 5 halo, 1 to 3 hydroxy, phenyl, C$_1$–C$_6$ alkoxycarbonyl;

$R^6$ is selected from: hydrogen, C$_1$–C$_6$ alkyl, and (CH$_2$)$_v$aryl, wherein the (CH$_2$)$_v$ and alkyl groups may be optionally substituted by —O(R$^2$), —S(O)$_m$R$^2$, —C(O)OR$^2$, —C(O)N(R$^2$)(R$^2$), —SO$_2$N(R$^2$)(R$^2$), or —N(R$^2$)C(O)N(R$^2$)(R$^2$), wherein the aryl group is selected from: phenyl, pyridyl, 1H-tetrazolyl, triazolyl, oxadiazolyl, pyrazolyl, thiadiazoyl, and benzimidazol-2-yl, which is optionally substituted with C$_1$–C$_6$ alkyl, C$_3$–C$_6$ cycloalkyl, amino, or hydroxyl;

X is selected from the group consisting of: hydrogen, —C≡N, —(CH$_2$)$_q$N(R$^2$)C(O)R$^2$, —(CH$_2$)$_q$N(R$^2$)C(O)(CH$_2$)$_t$aryl, —(CH$_2$)$_q$N(R$^2$)SO$_2$(CH$_2$)$_t$aryl, —(CH$_2$)$_q$N(R$^2$)SO$_2$R$^2$, —(CH$_2$)$_q$N(R$^2$)C(O)N(R$^2$)(CH$_2$)$_t$aryl, —(CH$_2$)$_q$N(R$^2$)C(O)N(R$^2$)(R$^2$), —(CH$_2$)$_q$C(O)N(R$^2$)(R$^2$), —(CH$_2$)$_q$C(O)N(R$^2$)(CH$_2$)$_t$aryl, —(CH$_2$)$_q$C(O)OR$^2$, —(CH$_2$)$_q$C(O)O(CH$_2$)$_t$aryl, —(CH$_2$)$_q$OR$^2$, —(CH$_2$)$_q$OC(O)R$^2$, —(CH$_2$)$_q$OC(O)(CH$^2$)$_t$aryl, —(CH$_2$)$_q$OC(O)N(R$^2$)(R$^2$), —(CH$_2$)$_q$C(O)R$^2$, —(CH$_2$)$_q$C(O)(CH$_2$)$_t$aryl, —(CH$_2$)$_q$N(R$^2$)C(O)OR$^2$, —(CH$_2$)$_q$N(R$^2$)SO$_2$N(R$^2$)(R$^2$), —(CH$_2$)$_q$S(O)$_m$R$^2$, and —(CH$_2$)$_q$S(O)$_m$(CH$_2$)$_t$aryl, where R$^2$, (CH$_2$)$_q$ and (CH$_2$)$_t$ group may be optionally substituted with C$_1$–C$_4$ alkyl, hydroxyl, C$_1$–C$_4$ lower alkoxy, carboxyl, N(R$^2$)(R$^2$), CONH$_2$, S(O)$_m$CH$_3$, carboxylate C$_1$–C$_4$ alkyl esters, or 1H-tetrazol-5-yl, and aryl is phenyl, naphthyl, pyridyl, thiazolyl, or 1H-tetrazol-5-yl groups which may be optionally substituted with halogen, —OR$^2$, —CON(R$^2$)(R$^2$), —C(O)OR$^2$, C$_1$–C$_4$ alkyl, —S(O)$_m$R$^2$, or 1H-tetrazol-5-yl;

Y is selected from the group consisting of: hydrogen, C$_1$–C$_{10}$ alkyl, —(CH$_2$)$_t$aryl, —(CH$_2$)$_q$(C$_3$–C$_7$ cycloalkyl), —(CH$_2$)$_q$-K-(C$_1$–C$_6$ alkyl), —(CH$_2$)$_q$-K-(CH$_2$)$_t$aryl, —(CH$_2$)$_q$-K-(CH$_2$)$_t$(C$_3$–C$_7$ cycloalkyl containing O, NR$^2$ S) and —(CH$_2$)$_q$-K-(CH$_2$)$_t$(C$_3$–C$_7$ cycloalkyl), where K is O, S(O)$_m$, C(O)NR$^2$, CH=CH, C≡C, N(R$^2$)C(O), C(O)NR$^2$, C(O)O, or OC(O), and where the alkyl, R$^2$, (CH$_2$)$_q$ and (CH$_2$)$_t$ groups are optionally substituted by C$_1$–C$_4$ alkyl, hydroxyl, C–C$_4$ lower alkoxy, carboxyl, —CONH$_2$ or a carboxylate C$_1$–C$_4$ alkyl ester, and aryl is phenyl, naphthyl, pyridyl, 1-H-tetrazol-5-yl, thiazolyl, imidazoly, indolyl, oxadiazolyl, pyrimidinyl, thiadiazolyl,pyrazolyl, oxazolyl, isoxazolyl, thiopheneyl, quinolinyl, pyrrazinyl, or isothiazolyl which is optionally substituted with halogen, —$OR^2$, —$C(O)OR^2$, $N(R^2)(R^2)$, —$C(O)N(R^2)(R^2)$, nitro, cyano, benzyl, $C_1$–$C_4$ alkyl, —$S(O)_m R^2$, or 1H-tetrazol-5-yl;

D is selected from: —$N(R^7)$—, —$S(O)_m$—, —$C(O)$— and —$C(H)(R^7)$—, wherein $R^7$ is selected from: —$R^2$, —$(CH_2)_q aryl$, —$C(O)R^2$, —$SO_2 R^2$, —$C(O)N(R^2)(R^2)$, —$C(O)OR^2$, 1-H-tetrazol-5-yl, —$SO_2 N(R^2)aryl$, —$SO_2 N(R^2)(R^2)$ and the $(CH_2)_q$ may be optionally substituted by $C_1$–$C_4$ alkyl, and the $R^2$ and aryl may be optionally further substituted with a substituent selected from: —$OR^{2a}$, —$C(O)OR^{2a}$, —$C(O)N(R^{2a})(R^{2a})$, halogen, —$C_1$–$C_4$ alkyl, and the aryl is selected from of triazolyl, oxadiazolyl, thiadiazolyl, thiazolyl, imidazolyl, and 1H-tetrazolyl;

l is 0, 1 or 2;

m is 0, 1, or 2;

q is 0, 1, 2, 3, or 4;

r is 0, 1, 2, or 3;

t is 0, 1, 2, or 3;

v is 0, 1, or 2;

x is 1; y is 1;

and pharmaceutically acceptable salts and individual diastereomers thereof.

3. The compound of claim 1 of the formula:

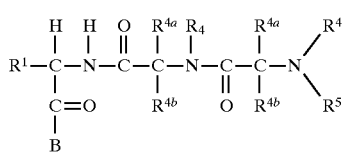

wherein:

$R^1$ is selected from the group consisting of:

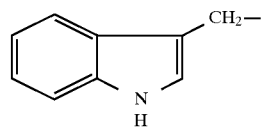

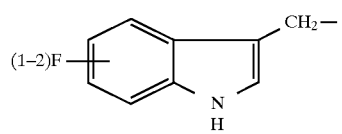

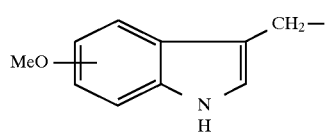

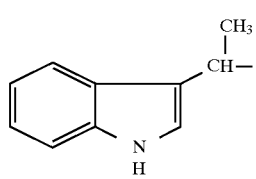

-continued

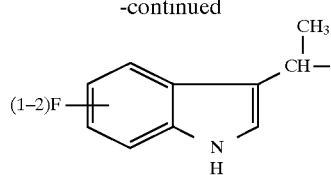

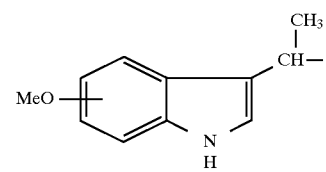

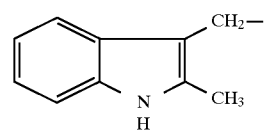

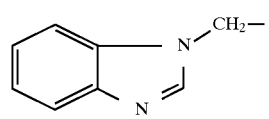

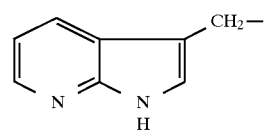

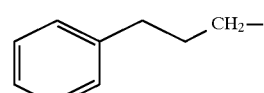

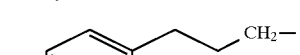

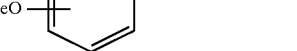

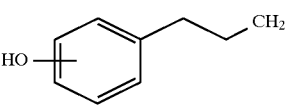

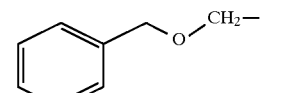

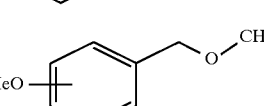

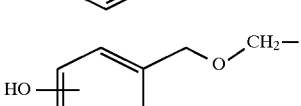

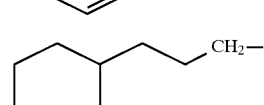

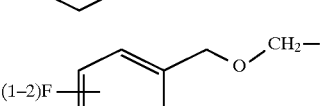

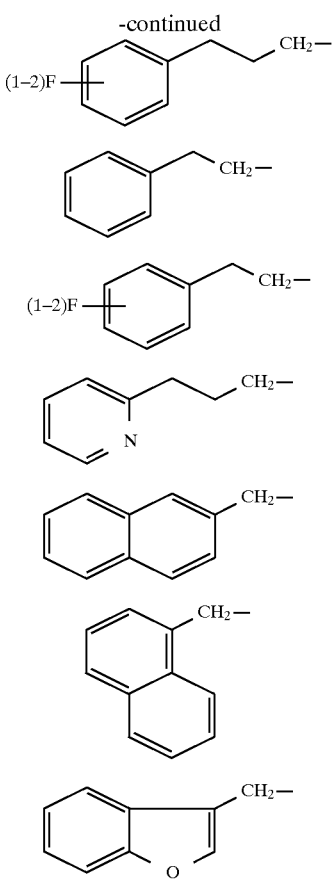

or their regioisomers where not specified;

R² is selected from the group consisting of:
hydrogen, —$C_1$–$C_6$ alkyl, —$C_3$–$C_7$ cycloalkyl, and —$CH_2$—phenyl, wherein the alkyl or the cyloalkyl is unsubstituted or substituted with hydroxyl, $C_1$–$C_3$ alkoxy, thioalkyl, —C(O)OR$^{2a}$, and wherein, if two —$C_1$–$C_6$ alkyl groups are present on one atom, the groups may be optionally joined to form a $C_3$–$C_8$ cyclic ring being selected from the group consisting of pyrrolidine, piperidine, piperazine, morpholine, thiomorpholine;

R$^{2a}$ is hydrogen, or $C_1$–$C_4$ alkyl;

B is selected from:

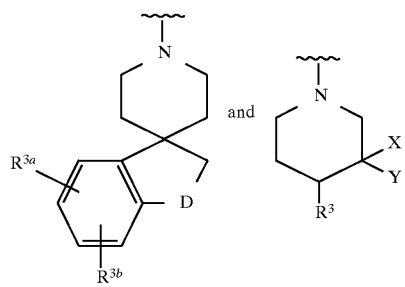

R³ is selected from: hydrogen or phenyl, wherein the phenyl is substituted in the ortho position by a substituent selected from the group consisting of: $C_1$–$C_6$ alkyl, halogen, —OR², —(CH$_2$)$_r$OR⁶, —(CH$_2$)$_r$N(R²)(R⁶), —(CH$_2$)$_r$(R⁶), —(CH$_2$)$_r$R⁶, —(CH$_2$)$_r$C(O)OR², —(CH$_2$)$_r$C(O)OR⁶, —(CH$_2$)$_r$C(O)R², —(CH$_2$)$_r$C(O)R⁶, —(CH$_2$)$_r$C(O)N(R²)(R²), —(CH$_2$)$_r$C(O)N(R²)(R⁶), —(CH$_2$)$_r$SO$_2$N(R²)(R⁶), —(CH$_2$)$_r$SO$_2$N(R²)(R²), —(CH$_2$)$_r$S(O)$_m$R⁶, and —(CH$_2$)$_r$S(O)$_m$R²;

R$^{3a}$ and R$^{3b}$ are independently selected from: hydrogen, —$C_1$–$C_6$ alkyl and halogen;

R⁴ and R⁵ are independently selected from hydrogen, $C_1$–$C_6$ alkyl, and substituted $C_1$–$C_6$ alkyl where the substituents are selected from halo, hydroxy, phenyl, and $C_1$–$C_6$ alkoxycarbonyl; or R⁵ and R⁴ may be taken together to form —(CH$_2$)$_d$–L$_a$(CH$_2$)$_e$— where L$_a$ is —C(R²)$_2$—, —O—, —S(O)$_m$— or —N(R²)—, d and e are independently 1 to 3 and R² is as defined above;

R$^{4a}$ and R$^{4b}$ are independently selected from: hydrogen, $C_1$–$C_6$ alkyl, or substituted $C_1$–$C_6$ alkyl where the substituents are selected from: imidazolyl, naphthyl, phenyl, indolyl, and p-hydroxyphenyl;

R$^{4c}$ is selected from hydrogen, $C_1$–$C_6$ alkyl, and substituted $C_1$–$C_6$ alkyl where the substituents are selected from 1 to 5 halo, 1 to 3 hydroxy, phenyl, $C_1$–$C_6$ alkoxycarbonyl;

R⁶ is selected from: hydrogen, $C_1$–$C_6$ alkyl, and (CH$_2$)$_v$aryl, wherein the (CH$_2$)$_v$ and alkyl groups may be optionally substituted by —O(R²), —S(O)$_m$R², —C(O)OR², —C(O)N(R²)(R²), —SO$_2$N(R²)(R²), or —N(R²)C(O)N(R²)(R²), wherein the aryl group is selected from: phenyl, pyridyl, 1H-tetrazolyl, triazolyl, oxadiazolyl, pyrazolyl, thiadiazoyl, and benzimidazol-2-yl, which is optionally substituted with $C_1$–$C_6$ alkyl, $C_3$–$C_6$ cycloalkyl, amino, or hydroxyl;

X is selected from the group consisting of: hydrogen,

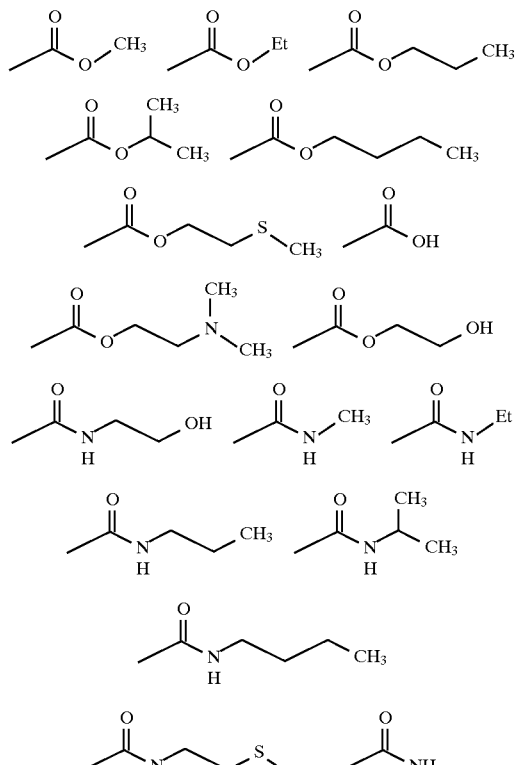

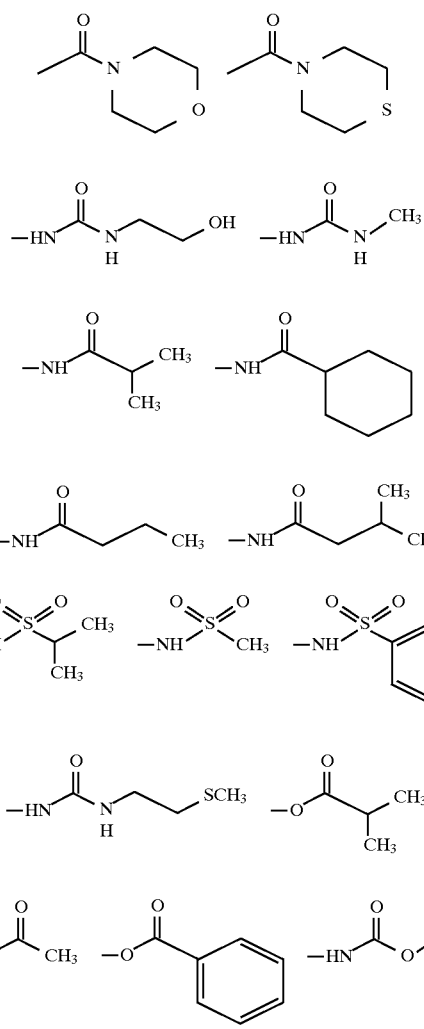
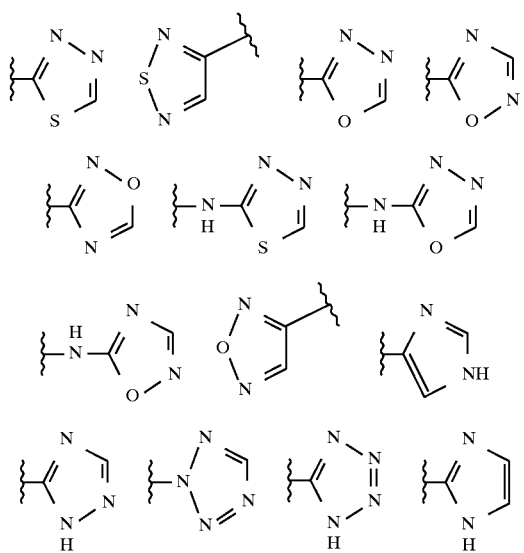
and further selected from the following group of heterocycles
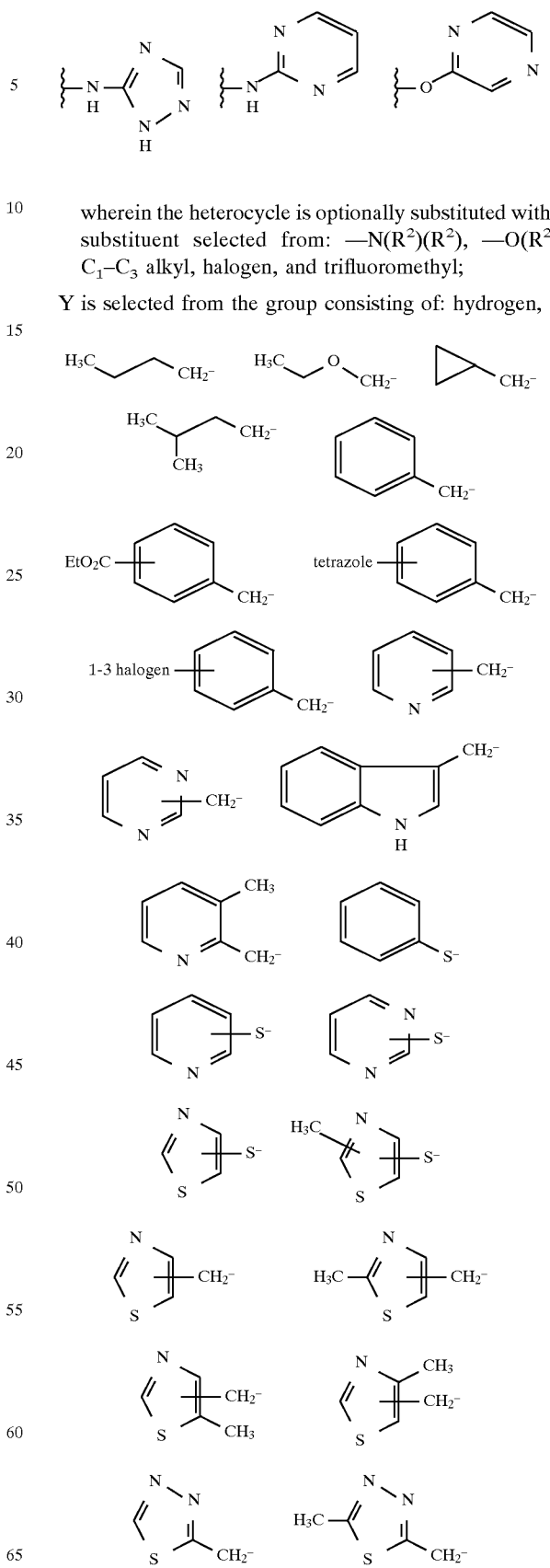
wherein the heterocycle is optionally substituted with a substituent selected from: $-N(R^2)(R^2)$, $-O(R^2)$, $C_1-C_3$ alkyl, halogen, and trifluoromethyl;
Y is selected from the group consisting of: hydrogen,

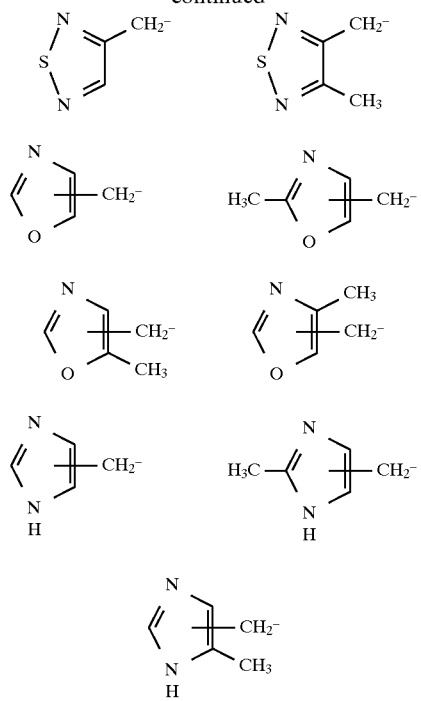

or their regioisomers whereof where not specified;

D is selected from: —N(R⁷)—, —S(O)ₘ—, —C(O)— and —C(H)(R⁷)—, wherein R⁷ is selected from: —R², —(CH₂)_q aryl, —C(O)R², —SO₂R², —C(O)N(R²)(R²), —C(O)OR², 1-H-tetrazol-5-yl, —SO₂N(R²)aryl, —SO₂N(R²)(R²) and the (CH₂)_q may be optionally substituted by C₁–C₄ alkyl, and the R² and aryl may be optionally further substituted with a substituent selected from: —OR²ᵃ, —C(O)OR²ᵃ, —C(O)N(R²ᵃ)(R²ᵃ), halogen, —C₁–C₄ alkyl, and the aryl is selected from of triazolyl, oxadiazolyl, 1H-tetrazolyl, and thiadiazolyl;

1 is 0, 1 or 2;

m is 0, 1, or 2;

q is 0, 1, 2, 3, or 4;

r is 0, 1, 2, or 3;

t is 0, 1, 2, or 3;

v is 0, 1, or 2;

and pharmaceutically acceptable salts and individual diastereomers thereof.

4. The compound of claim 1 of the formula:

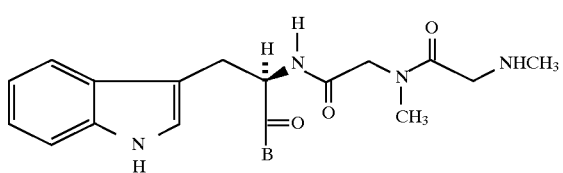

wherein B is selected from the group consisting of:

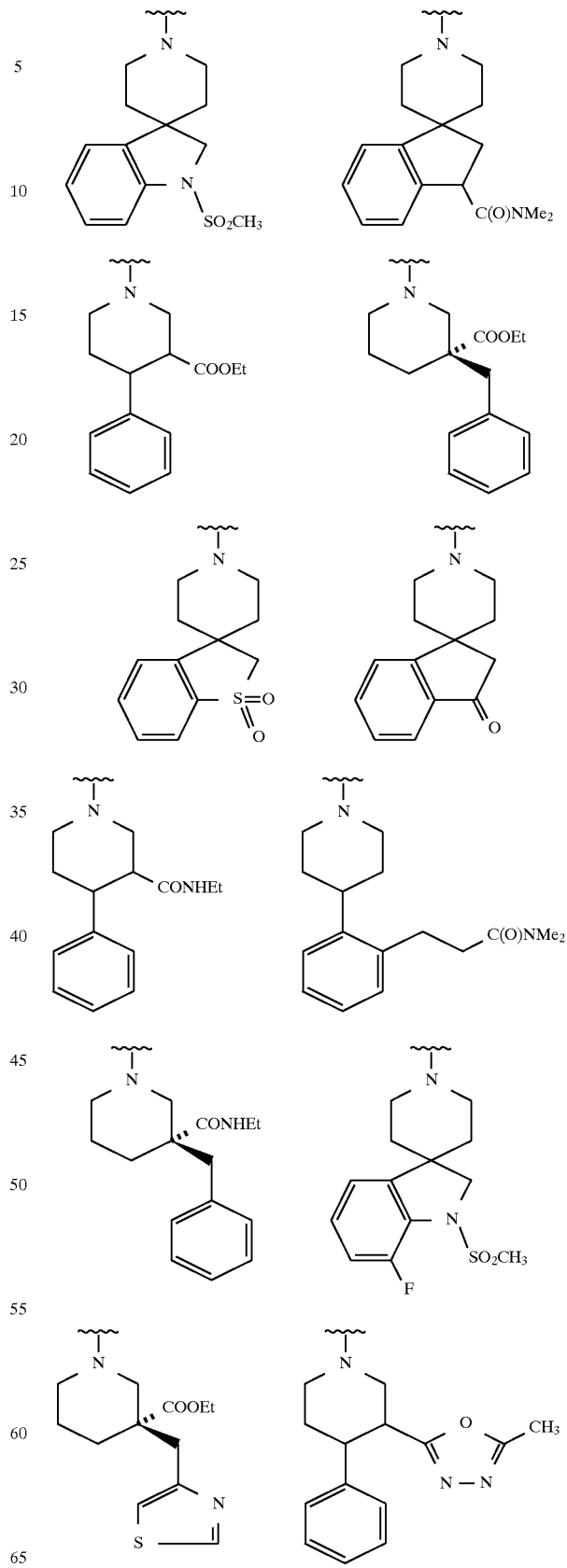

-continued
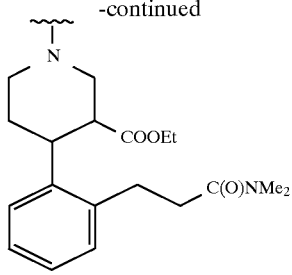
and pharmaceutically acceptable salts and individual diastereomers thereof.
5. The compound of claim 1 of the formula:
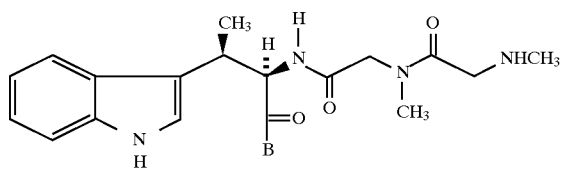
wherein B is selected from the group consisting of:
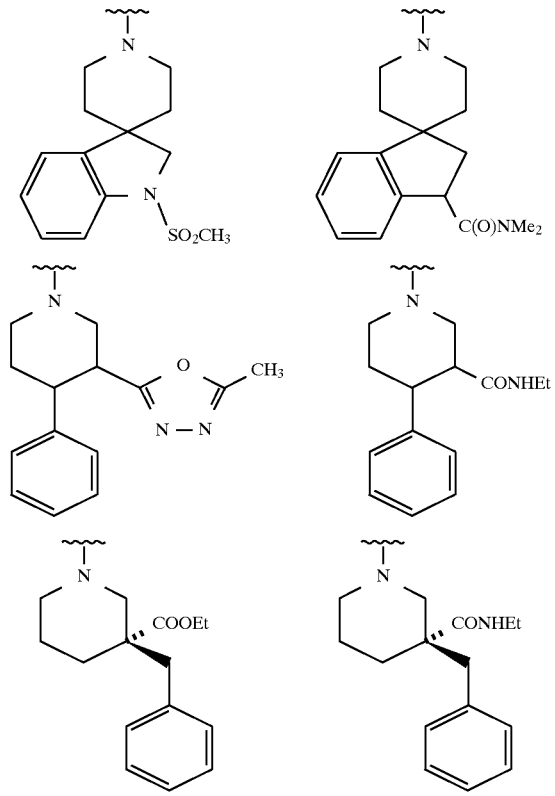
-continued
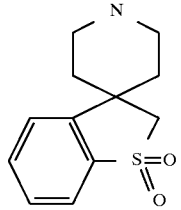
and pharmaceutically acceptable salts and individual diastereomers thereof.
6. The compound of claim 1 of the formula:
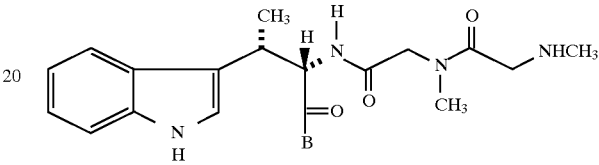
wherein B is selected from the group consisting of:
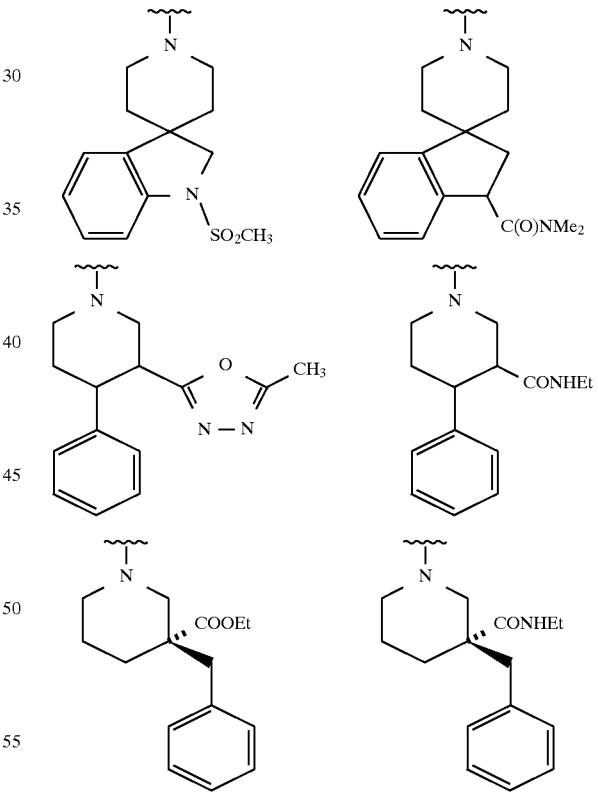

-continued
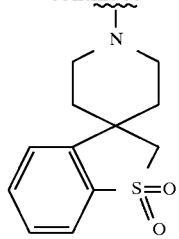
and pharmaceutically acceptable salts and individual diastereomers thereof.
7. The compound of claim 1 of the formula:
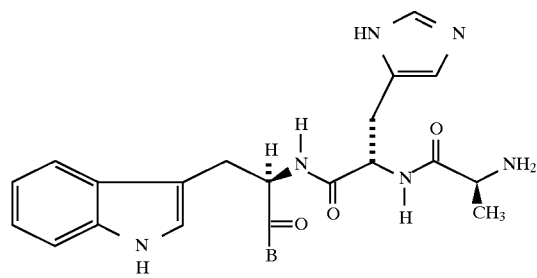
wherein B is selected from the group consisting of:
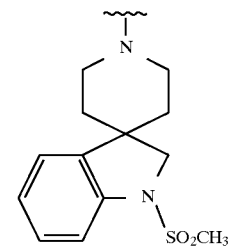 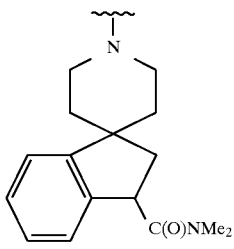
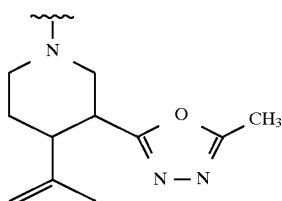 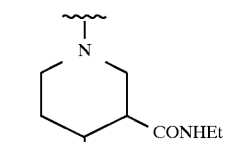
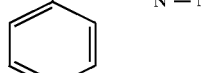 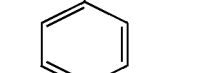
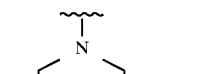 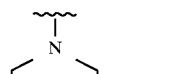
-continued
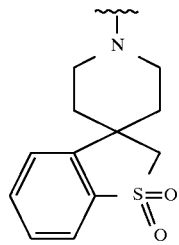
and pharmaceutically acceptable salts and individual diastereomers thereof.
8. A compound which is selected from the group consisting of:
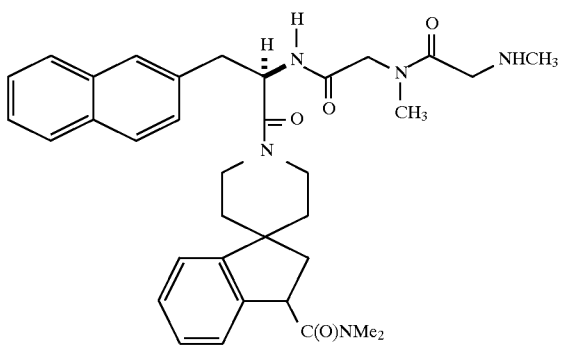
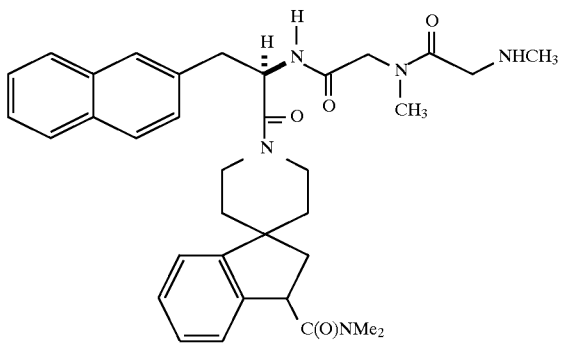
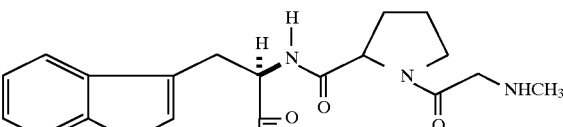
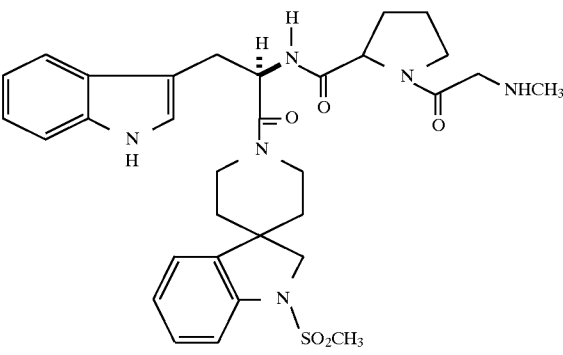

-continued

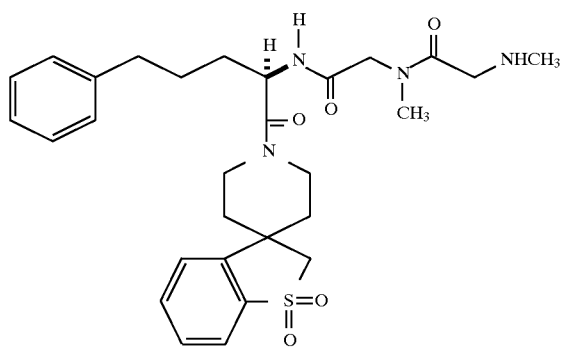

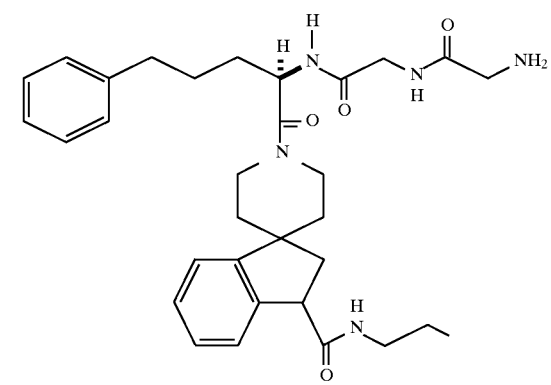

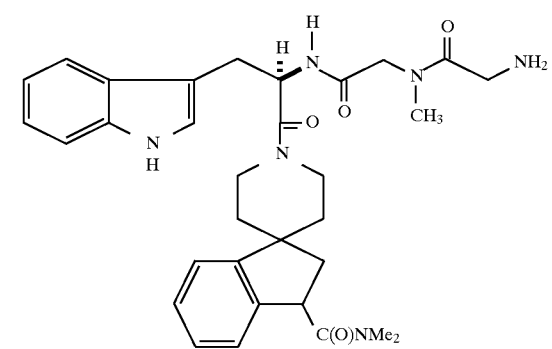

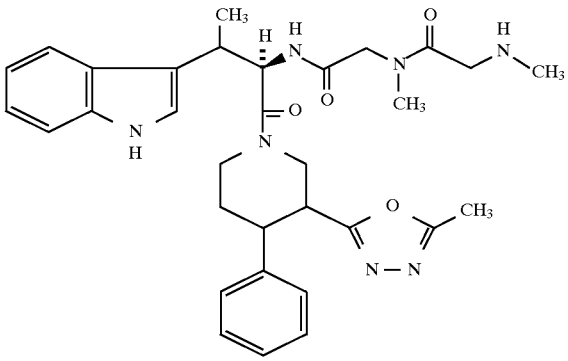

-continued

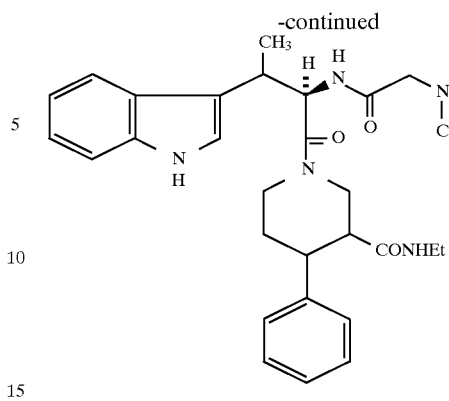

and pharmaceutically acceptable salts and individual diastereomers therefore where not otherwise specified.

9. A pharmaceutical composition which comprises an inert carrier and the compound of claim 1.

10. A pharmaceutical composition useful for increasing the endogenous production or release of growth hormone in a human or an animal which comprises an inert carrier and an effective amount of the compound of claim 1 in combination with an additional growth hormone secretagogue.

11. A pharmaceutical composition useful for the treatment of osteoporosis which comprises a combination of a bisphosphonate compound and the compound of claim 1.

12. The pharmaceutical composition of claim 11 wherein the bisphosphonate compound is alendronate.

13. A method for increasing levels of endogenous growth hormone in a human or an animal which comprises administering to such human or animal an effective amount of the compound of claim 1.

14. A method for increasing levels of endogenous growth hormone in a human or an animal which comprises administering to such human or animal an effective amount of the compound of claim 1 in combination with an additional growth hormone secretagogue.

15. The method of claim 14 wherein the additional growth hormone secretagogue is selected from the group consisting of: growth hormone releasing factor; an analog of growth hormone releasing factor; IGF-1; and IGF-2.

16. A method for increasing feed efficiency, promoting growth, increasing milk production and improving the carcass quality of livestock which comprises administering to such livestock an effective amount of the compound of claim 1.

17. A method for the treatment of a disease or a condition which is benefited by the anabolic effects of enhanced growth hormone levels that comprises administering to a patient in need thereof an effective amount the compound of claim 1.

18. The method of claim 17 wherein the disease or condition is selected from the group consisting of: osteoporosis; catabolic illness; immune deficiency, including that in individuals with a depressed $T_4/T_8$ cell ratio; bone fracture; musculoskeletal impairment in the elderly; growth hormone deficiency in adults or in children; short stature in children; obesity; sleep disorders; cachexia and protein loss due to chronic illness such as AIDS or cancer; and the treatment of patients recovering from major surgery, wounds or burns.

19. A method for the treatment of osteoporosis which comprises administering to a patient with osteoporosis a combination of a bisphosphonate compound and the compound of claim 1.

20. The method of claim 19 wherein the bisphosphonate compound is alendronate.

* * * * *